(12) United States Patent
Argenta et al.

(10) Patent No.: US 7,198,046 B1
(45) Date of Patent: *Apr. 3, 2007

(54) WOUND TREATMENT EMPLOYING REDUCED PRESSURE

(75) Inventors: Louis C. Argenta, Winston-Salem, NC (US); Michael J. Morykwas, Pfafftown, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/026,353

(22) Filed: Feb. 19, 1998

Related U.S. Application Data

(63) Continuation of application No. 08/467,243, filed on Jun. 6, 1995, now abandoned, which is a continuation of application No. 08/028,677, filed on Mar. 9, 1993, now Pat. No. 5,636,643, which is a continuation-in-part of application No. 07/792,061, filed on Nov. 14, 1991, now Pat. No. 5,645,081.

(51) Int. Cl.
*A61B 19/00* (2006.01)

(52) U.S. Cl. .................................. 128/897; 602/42

(58) Field of Classification Search ......... 128/897–898; 602/42–53
See application file for complete search history.

(56) References Cited

U.S. PATENT DOCUMENTS

| 765,746 A | 7/1904 | Miner |
|---|---|---|
| 774,529 A | 11/1904 | Nieschang |

(Continued)

FOREIGN PATENT DOCUMENTS

| DE | 561757 | 10/1932 |
|---|---|---|
| DE | 847475 C | 6/1952 |
| DE | 2809828 | 9/1978 |
| DE | 4111122 | 4/1993 |
| EP | 0688189 | 6/1900 |
| EP | 0620720 | 3/1998 |
| EP | 0688189 | 9/2000 |
| EP | 0688189 B2 | 6/2005 |
| GB | 641061 | 8/1950 |
| GB | 1273342 | 5/1972 |
| GB | 1457164 | 12/1976 |
| GB | 2195255 | 4/1988 |
| GB | 2195855 | 4/1988 |
| WO | 80/01139 | 6/1980 |
| WO | 87/00439 | 1/1987 |
| WO | 9011795 | 10/1990 |
| WO | 9100718 | 1/1991 |
| WO | WO9116030 | 8/1991 |
| WO | WO9219313 | 11/1992 |
| WO | 9220299 | 11/1992 |
| WO | 2003/101385 | 12/2003 |

OTHER PUBLICATIONS

M. Gosta Arturson, *The Pathophysiology of Severe Thermal Injury*, JBCR, 6(2):129–146 (Mar.–Apr. 1985).

R.A.F. Clark et al., The Molecular and Cellular Biology of Wound Repair, Chapter 1 (1988).

(Continued)

*Primary Examiner*—John P. Lacyk
(74) *Attorney, Agent, or Firm*—Niels Haun; Dann, Dorfman, Herrell & Skillman, PC

(57) ABSTRACT

A method of treating tissue damage comprises applying a negative pressure to a wound sufficient in time and magnitude to promote tissue migration and thus facilitate closure of the wound. The method is applicable to wounds, burns, infected wounds, and live tissue attachments. A wound treatment apparatus is provided in which a fluid impermeable wound cover is sealed over a wound site. A screen in the form of an open-cell foam screen or a rigid porous screen is placed beneath the wound cover over the wound. A vacuum pump supplies suction within the wound cover over the treatment site.

45 Claims, 5 Drawing Sheets

U.S. PATENT DOCUMENTS

| | | | |
|---|---|---|---|
| 843,674 | A | 2/1907 | Funk |
| 1,355,679 | A | 10/1920 | McDonnell |
| 1,355,846 | A | 10/1920 | Rannells |
| 1,385,346 | A | 7/1921 | Taylor |
| 1,936,129 | A | 11/1933 | Fisk |
| 2,025,492 | A | 12/1935 | Aird |
| 2,195,771 | A | 4/1940 | Estler |
| 2,232,254 | A | 2/1941 | Morgan |
| 2,280,915 | A | 4/1942 | Johnson |
| 2,338,339 | A | 1/1944 | LaMere |
| 2,547,758 | A | 4/1951 | Keeling |
| 2,969,057 | A | 1/1961 | Simmons |
| 3,026,526 | A | 3/1962 | Montrose |
| 3,026,874 | A | 3/1962 | Stevens |
| 3,042,041 | A | 7/1962 | Jascalevich |
| 3,115,138 | A | 12/1963 | McElvenny |
| 3,115,318 | A | 12/1963 | Caillette |
| 3,324,855 | A | 6/1967 | Heimlich |
| 3,367,332 | A | 2/1968 | Groves |
| 3,382,867 | A | 5/1968 | Reaves |
| 3,478,736 | A | 11/1969 | Roberts et al. |
| 3,481,326 | A | 12/1969 | Schamblin |
| 3,486,504 | A | 12/1969 | Austin, Jr. |
| 3,520,300 | A | 7/1970 | Flower et al. ............ 128/276 |
| 3,568,675 | A | 3/1971 | Harvey |
| 3,572,340 | A | 3/1971 | Lloyd et al. |
| 3,610,238 | A | 10/1971 | Rich, Jr. |
| 3,682,180 | A | 8/1972 | McFarlane |
| 3,713,622 | A | 1/1973 | Dinger |
| 3,753,439 | A | 8/1973 | Brugarolas et al. |
| 3,826,254 | A | 7/1974 | Mellor |
| 3,874,387 | A | 4/1975 | Barbieri |
| 3,896,810 | A | 7/1975 | Akiyama |
| 3,908,664 | A | 9/1975 | Loseff |
| 3,938,540 | A | 2/1976 | Holbrook et al. |
| 3,954,105 | A | 5/1976 | Nordby |
| 3,978,855 | A | 9/1976 | McRae et al. |
| 3,993,080 | A | 11/1976 | Loseff |
| RE29,319 | E | 7/1977 | Nordby |
| 4,080,970 | A | 3/1978 | Miller |
| 4,112,947 | A | 9/1978 | Nehring |
| 4,139,004 | A | 2/1979 | Gonzalez, Jr. |
| 4,149,541 | A | 4/1979 | Gammons et al. |
| 4,169,563 | A | 10/1979 | Leu |
| 4,172,455 | A | 10/1979 | Beaussant |
| 4,224,941 | A | 9/1980 | Stivala |
| 4,224,945 | A | 9/1980 | Cohen |
| 4,250,882 | A | 2/1981 | Adair |
| 4,261,363 | A | 4/1981 | Russo |
| 4,275,721 | A | 6/1981 | Olson |
| 4,297,995 | A | 11/1981 | Golub |
| 4,373,519 | A | 2/1983 | Errede |
| 4,382,441 | A | 5/1983 | Svedman |
| 4,392,853 | A | 7/1983 | Muto |
| 4,419,097 | A | 12/1983 | Rowland |
| 4,452,845 | A | 6/1984 | Lloyd et al. |
| 4,459,139 | A | 7/1984 | vonReis et al. |
| 4,465,062 | A | 8/1984 | Versaggi et al. |
| 4,469,092 | A | 9/1984 | Marshall et al. |
| 4,475,909 | A | 10/1984 | Eisenberg |
| 4,480,638 | A | 11/1984 | Schmid |
| RE31,887 | E | 5/1985 | Hodgson |
| 4,525,166 | A | 6/1985 | Leclerc |
| 4,527,064 | A | 7/1985 | Anderson |
| 4,540,412 | A | 9/1985 | Van Overloop |
| 4,543,100 | A | 9/1985 | Brodsky |
| 4,569,674 | A | 2/1986 | Phillips et al. |
| 4,573,965 | A | 3/1986 | Russo |
| 4,605,399 | A | 8/1986 | Weston |
| 4,608,041 | A | 8/1986 | Nielsen |
| 4,624,656 | A | 11/1986 | Clark et al. |
| 4,627,427 | A | 12/1986 | Arco |
| 4,640,688 | A | 2/1987 | Hauser |
| 4,655,754 | A | 4/1987 | Richmond et al. |
| 4,661,093 | A | 4/1987 | Beck et al. |
| 4,713,052 | A | 12/1987 | Beck |
| 4,717,382 | A | 1/1988 | Clemens et al. |
| 4,743,232 | A | 5/1988 | Kruger |
| 4,753,231 | A | 6/1988 | Lang et al. |
| 4,759,354 | A | 7/1988 | Quarfoot |
| 4,764,167 | A | 8/1988 | Tu |
| 4,765,316 | A | 8/1988 | Marshall |
| 4,773,409 | A | 9/1988 | Cilento et al. |
| 4,778,456 | A | 10/1988 | Lokken |
| 4,820,265 | A | 4/1989 | DeSatnick |
| 4,820,284 | A | 4/1989 | Hauri |
| 4,834,110 | A | 5/1989 | Richard |
| 4,836,192 | A | 6/1989 | Abbate |
| 4,838,883 | A | 6/1989 | Matsuura |
| 4,840,187 | A | 6/1989 | Brazier |
| 4,841,962 | A | 6/1989 | Berg et al. |
| 4,851,545 | A | 7/1989 | Song |
| 4,860,737 | A | 8/1989 | Lang et al. |
| 4,863,449 | A | 9/1989 | Therriault |
| 4,875,473 | A | 10/1989 | Alvarez |
| 4,878,901 | A | 11/1989 | Sachse |
| 4,906,233 | A | 3/1990 | Moriuchi et al. |
| 4,917,112 | A | 4/1990 | Kalt |
| 4,921,492 | A | 5/1990 | Schultz |
| 4,925,447 | A | 5/1990 | Rosenblatt |
| 4,931,519 | A | 6/1990 | Song |
| 4,941,882 | A | 7/1990 | Ward et al. |
| 4,953,565 | A | 9/1990 | Tachibana et al. |
| 4,969,880 | A | 11/1990 | Zamierowski |
| 4,969,881 | A | 11/1990 | Viesturs |
| 5,035,884 | A | 7/1991 | Song |
| 5,071,403 | A | 12/1991 | Larason |
| 5,086,764 | A | 2/1992 | Gilman |
| 5,100,396 | A | 3/1992 | Zamierowski |
| 5,106,362 | A | 4/1992 | Gilman |
| 5,113,871 | A | 5/1992 | Viljanto |
| 5,149,331 | A | 9/1992 | Ferdman |
| 5,228,431 | A | 7/1993 | Giarretto |
| 5,261,893 | A | 11/1993 | Zamierowski |
| 5,636,643 | A | * 6/1997 | Argenta et al. ............ 128/897 |
| 5,645,081 | A | 7/1997 | Argenta et al. |
| 5,720,720 | A | 2/1998 | Laske |
| 6,551,317 | B2 | 4/2003 | Berish et al. |

OTHER PUBLICATIONS

Jeter, K.F. et al. (eds.), "Managing Draining Wounds and Fistulae: New and Established Methods," *Chronic Wound Care: Health Management Publications*, 1990, pp. 240–246.

Aeros, "Moblvac II."

Aeros, Aeros Instruments, Inc. 1111 Lakeside Drive, Gurnee, IL 60031. Aug. 1993. "Care–E–Vac."

Emerson, Series 55. J.H. Emerson Co., 22 Cottage Park Ave., Cambridge, MA 02140, "Emerson Post–Operative Suction Pumps."

Emerson, J.H. Emerson Co., (address: same as above). "Emerson Transport Suction Unit."

Aeros, Aeros Instruments, Inc. 3411 Commerical Ave., Northbrook, IL 60062. Oct. 1988. Part No. 1504–02 7N. "Instavac Aspirator."

"Pleur–evac. Adult–Pediatric, Non–Metered." Code No.: A–4000. Control No.: F7961J.

Instruction Manual, Creative Medical Laboraties, Inc. P.O. Box 6347, Rochester, Minn. 55903. "TUGS" (Transportable Universal Gradient Suction).

Deknatel, Div. of Howmedica, Inc. Queens Village, NY 11429. "Pleur–evac."

Sparta Instrument Corp. 26602 Corporate Ave., Hayward, CA 94545. "Power Source Multi–Purpose Surgical Aspirator."

Wells Johnson Company, 2045 N. Forbes Blvd., Suite 106, Tucson, AZ. "Point 5 Aspirator."

Microtek Heritage, Inc. P.O. Box 2487, Columbus, MS 39704. "Wound–Evac ET."

Fleischmann, W. *Wund Forum Spezial*. IHW '94. "Vakuumversiegelung zur Behandlung von Problemwunden" (with English translation: "Vacuum Sealing for Treament of Problematical Wounds."

Fleischmann, W. *Acta Orthopaedica Belgica*. vol. 58, Suppl. I–1992 "Treatment of Bone and Soft Tissue Defects in Infected Nonunion."

Fleischmann, W. *Unfall Chirurg*. Springer–Verlag 1993. "Vakuumversiegelung zur Behandlung des Weichteilschadens bei offenen Frakturen." (English abstract, no English translation.)

Valenta, A. *American Journal of Nursing*. Apr. 1994. "Using the Vacuum Dressing Alternative for Difficult Wounds."

Junod, "Hypermia by Suction Apparatus" Chapter VIII.

Landis et al, Robinette Foundation of the Hospital of the University of Pennsylvania, "The Effects of Alternate Suction and Pressure on Blood Flow to the Lower Extremeties".

Hargens et al., Space Physiology Laboratory, Life Science Division, NASA Ames Research Center, "Control of Circulatory Functions in Altered Gravitational Fields".

Wolthuis et al, Physiological Reviews, 54: 566–595, Jul. 1974, "Physiological Effects of Locally Applied Reduced Pressure in Man".

Viljanto et al., Br. J. Surg., 63: 427–430, 1976, "Local Hyperalimentation of Open Wounds".

Dillon, Angiology—The Journal of Vascular Diseases, pp. 47–55, Jan. 1986, "Treatment of Resistant Venous Stasis Ulcers and Dermatitis with the End–Diastolid Pneumatic Compression Boot".

Lundvall et al., Acta Physiol Scand, 136: 403–409, accepted Jan. 28, 1989, "Transmission of externally applied negative pressure to the underlying tissue. A study on the upper arm of man".

Klemp et al., The Journal of Investigative Dermatology, pp. 725–726 (1989), "Subcutaneous Blood Flow in Early Male Pattern Baldness".

A. Harle, Z. Orthop., 127: 513–517 (1989), "Schwachstellen herkommlicher Drainagen".

Dunlop et al., Br. J. Surg., 77: 462–563 (1990), "Vacuum drainage of groin wounds after vascular surgery: a controlled trail".

Maddin et al., International Journal of Dermatology, 29: 446–450 (1990), "The Biological Effects of a Pulsed Electrostatic Field with Specific Reference to Hair: Electrorichogenesis".

Nakayama et al., Ann. Plast. Surg., 26: 499–502 (1991), "A New Dressing Method for Free Skin Grafting in Hands".

Hargens et al., Aviation, Space and Environmental Medicine, pp. 934–937, Oct. 1991, "Lower Body Negative Pressure to Provide Load Bearing in Space".

Author unknown, Science, Sep. 1992, p. 42, "The Not–So–Bald–Truth".

Techno Takatsuki Co., Ltd., 8–16 Natchonishimachi, Takatsuki City, Osaka, Japan, "HiBlow Air Pump".

Wells Johnson Company, 2045 N. Forbes Blvd., Suite 106, Tucson, AZ, "Suction Tips".

Industrial Equipment News, P.O. Box 1158, Skokie, IL 60076–9786, "Miscellaneous Equipment".

Letsou et al. "Stimulation of Adenylate Cyclase Activity in Cultured Endothelial Cells Subjected to Cyclic Stretch." Cardiovascular Surgery 3. Toronto. Sep. 1989. 634–639.

Bucalo et al. "Inhibition of Cell Proliferation by Chronic wound Fluid." Wound Repair and Regeneration. Miami. 1991. 181–186.

Falanga, Vincent. "Growth Factors and Chronic Wounds: The Need to Understand the Microenvironmet." Journal of Dermatology, Bol. 19: 667–672. 1992.

Urschel et al. "The Effect of Mechanical Stress on Soft and Hard Tissue Repair; a Review." British Journal of Plastic Surgery. 41, 182–186. 1988.

Gogia, Prem P. "The Biology of Wound Healing." Ostomy/Wound Management. Nov.–Dec. 1992. pp. 12–20.

Wysocki et al. "Wound Fluid from Chronic Leg Ulcers Contains Elevated Levels of Metalloproteinases MMP–2 and MMP–9," The Society for Investigative Dermatology, Inc. Jul. 1993. 64–68.

Olenius et al. "Mitotic Activity in Expanded Human Skin." Plastic and Reconstructive Surgery. Feb. 1993. 213–215.

Mulder, G.D. et al. (eds), *Clinician's Pocket Guide to Chronic Wound Repair,* (Spartanburg, SC: Wound Healing Publications), 1991, pp. 54–55.

Chariker, M.E. et al. (eds.), "Effective Management of Incisional and Cutaneous Fistulae with Closed Suction Wound Drainage," Contemporary Surgery, vol. 34, Jun. 1989, pp. 59–63.

Rastgeldi, S.: I. Pressure Treatment of Peripheral Vascular Diseases. II. Intermittent Pressure Treatment of Peripheral Vascular Diseases. Opuscula Media, Suppl. XXVII, 1972.

OP–Journal Nr. 3, Jahr. 6, Dec. 1990, pp. 31–35 W. Fleischmann, M. Mentzel, L. Kinzl "BWS, Gefahren und Komplikationen der Therapie".

Zumtobel et al., (1991) "Wunddrainage in der Elekiveund Notfallchirurgie" Wolfgang Pabst Verlag, relevant p. 12, left column. English Translation attached.

Saechtling, Kunststoff–Taschenbuch, 24. Ausgabe 1989, S. 439, 477. English Translation attached.

Mutschler, W. Bakker D.J., "Temporarer Hautersatz", ZFA 1989, Heft, 24, S. 714–720 als Sonderdruck. English Translation attached.

W. Fleischmann, U. Becker, M. Bischoff, H. Hoekstra, "Vacuum sealing: indication, technique, and results", Eur. J. Orthop & Traumato (1995)5:37–40.

Argenta LC. Morykwas MJ. Vacuum–assisted closure: a new method for wound control and treatment: clinical experience. Ann Plast Surg 1997;38:563–576.

Morykwas MJ. Argenta LC. Shelton–Brown EI. McGuirt W. Vacuum–assisted closure: a new method for wound control and treatment: animal studies and basic foundation. Ann Plast Surg 1997;38:553–62.

Davydov IA. Larichev AB. Smirnov AP. Flegontov VB. Vakuum–terapiia v lechenii ostrykh gnoinykh zabolevanii miagkikh tkanei i gnoinykh ran. [Vacuum therapy of acute suppurative diseases of soft tissues and suppurative wounds]. Russian Vestnik Khirurgii Imeni i—i—Grekkova 1988; 141:43–6.

Davydov IA. Abramov AI. Larichev AB. Vakuum–terapiia v preduprezhdenii posleoperatsionnoi ranevoi infektsii. [Vacuum therapy in the prevention of postoperative wound infection]. Russian Vestnik Khirurgi Imen i—i—Grekova 1991;147:91–5.

Iankov NI. Stimuliatsiia konsolidatsii perelomov nizhnei cheliusti vaktuumnoi terapiei. [Stimulation of consoldiation of mandibular fractures by means of vacuum therapy]. Russian. Stomatologiia 1971:50:86.

Inoiatov IM, Aleksandrov VB. Lechenie promezhnostnoi rany posle amputatsii priamoi kishki vakuum–aspiratsiei. [Vacuum–aspiration in the treatment of the perineal wound following extirpation of the rectum]. Russian. Khirurgiia 1971:47:74–8.

Kochnev VA. Primenenie vakuum–drenazhnoi sistemy dlia profilaktiki posleoperatsionnykh ranevykh oslozhnenii u bol'nykh opukholiami. [The use of a vacuum drainage system in the prevention of postoperative wound complications in tumor patients]. Russian Voprosy Onkologii 1967:13:102–5.

Mirazimov BM. Svobodnaia kozhnaia plastika stopy s podgotovkoi ranevoi poverkhnosti vakumirovaniem [Free skin graft of the foot with vacuum preparation of the wound surface]. Russian. Ortopediia Travmatologiia i Protezirovanie 1966:27:19–22.

Mirazimov BM. Vasina TA. Mezhericher MI. Mikroflora dlitel'no nekazhivaiushchikh ran i effektivnost' metoda vakuumirovaniia. [Microflora of prolonged non–healing wounds and the effectiveness of the vacuum evaporative method]. Russian. Khirurgiia 1967:43:40–3.

Mirazimow BM. Vorbereitung von Wunden und Geschwuren zur Hautplastik unter Anwendung der Vakuumierung [Preparation of wounds and abcesses for dermatoplasty by means of a vacuum device]. German. Beitrage zur Orthopadie und Traumatologie 1967:14:224–30.

Netudykhatka O. Vliianie nizkogo dozirovannogo vakuuma na techenie reparativnogo protsessa v kostnoi tkani [Effect of low vacuum on the course of the reparative process in bone tissue]. Russian. Voprosy Kurortologii. Fizioterapii i Lechebnoi Fizicheskoi Kultury 1972:37:411–5.

Volkov LA. Ispol'zovanie vakuum–drenazhnoi sistemy v khirurgicheskoi praktike. [Use of vacuum–drainage system in surgical practice]. Russian. Klinicheskaia Khirurgiia. 1973:7:54–5.

Teder H Sanden G Svedman P. Continuous Wound Irrigation in the Pig. J Invest Surg 1990:3:339–407.

Nakayama Y. Tomotari I. Soeda. S. A New Method for the Dressing of Free Skin Grafts. Plast Reconstr Surg 1990:86:1216–1219.

Nakayama Y. Soeda. A New Method for Free Skin Grafting in Hands. Ann Plast Surg 1991:26:499–502.

Fleischmann W. Strecker W. Bombelli M. Kinzl L. [Vacuum sealing as treatment of soft tissue damage in open fractures]. [German] Unfallchirug 1993:96:488–92.

Brock WB. Barker DE. Burns RP. Temporary Closure of Open abdominal wounds: the vacuum pack. Amer Surg 1995:61:30–5.

Shein M, Saadia R. Jameson JR, Decker GAG. The "sandwich technique" in the Management of the Open Abdomen. Br J Surg 1986:73:369–70.

Broome A. Hansson L. Lundgren F. Smedberg S. Open Treatment of Abdominal Septic Catastrophies. World J. Surg 1983:7:792–6.

Valenta AL. Using the vacuum dressing alternative for difficult wounds. American Journal of Nursing 1994:94:44–5.

Vatanasapt V. Areemit S. Jeeravipoolvarn P. et al. Red rubber bulb, cheap and effective vacuum drainage. Journal of the Medical Association of Thailand 1989:72:193–7.

Brummelkamp WH. Taat CW. Slors JF. High–vacuum drainage and primary perineal wound closure in abdominoperineal excision of the rectum. Netherlands Journal of Surgery 1991:43:236–9.

Morykwas J. Argenta LC. Nonsurgical modalities to enhance healing and care of soft tissue wounds. Journal of the Southern Orthopaedic Association 1997:6:279–88.

Sames CP. Sealing of wounds with vacuum drainage [letter] Br Med J 1977:2:1123.

Greer SE. Longaker MT. Margiotta M. Preliminary Results from a Multicenter Randomized, Controlled, Study of the Use of Subatmospheric Pressure Dressing for Pressure Ulcer Healing. Wound Repair and Regeneration 1999:7:255.

Greer SE. Longaker MT. Margiotta M. Mathews AJ. Kasabian A. The Use of Subatmospheric Pressure Dressing for the Coverage of Radial Forearm Free Flap Donor–Site Exposed Tendon Complications. Ann Plast Surg 1999;43:551–554.

Greer SE. Duthie E. Cartolano B. Koehler KM. Maydick–Youngberg D. Longaker MT. Techniques for Applying Subatmospheric Pressure Dressing to Wounds in Difficult Regions of Anatomy. JWOCN 1999;26:250–3.

Greer SE. Kasabian A. Thorne C. Borund L. Sims CD. Hsu M. The Use of Subatmospheric Pressure Dressing to Salvage a Gustilo Grade IIIB Open Tibia Fracture with Concomitant Osteomyelitis and Avert a Free Flap. Ann Plast Surg 1998;41:687.

Genecov DG. Schneider AM. Morykwas MJ. et al. A Controlled subatmospheric pressure dressing increases the rate of skin graft donor site reepithelialization. Ann Plast Surg 1998;40:219–25.

Mendez–Eastman S. Negative pressure wound therapy. Plastic Surgical Nursing 1998;18:27–9.

Banwell P. Withey S. Holten I. The use of negative pressure to promote healing [letter: comment]. Brit J Plast Surg 1998;51:79.

Blackburn J H Boemi L, Hall WW, et al. Negative–pressure dressings as a bolster for skin grafts. Ann Plast Surg 1998;40:453–7.

Smith LA. Barker DE. Chase CW. et al. Vacuum Pack Technique of Tempoaray Abdominal Closure: A Four–Year Experience. Amer Surg 1997;63:1102–8.

McCulloch JM. Kemper CC. Vacuum–Compression Therapy for the Treatment of an Ischemic Ulcer. Physical Therapy 1998;73:165–9.

Mullner T. Mrkonjic L. Kwasny O. Vecsei V. The use of negative pressure to promote the healing of tissue defects: a clinical trial using the vacuum sealing techniques [see comments]. Brit J Plast Surg 1997;50:194–9.

Mirazimov, B.M.: Free Skin Grafting of Wounds and Ulcers using the "Vacuum Treatment" Method. Citation data not given, pp. 54–58.

Davydov, Iu.A. (Prof.), et al. "Wound Healing Under the Conditions of Vacuum Draining" [citation data unavailable, pp. 21–26]. English Translation is enclosed.

Marie Knight, "A Second Skin for Patients with Large Drainage Wounds," Nursing 6(1) p. 37, 1976.

Oscar Ramirez, "Optimal Wound Healing under Op–Site Dressing", Plas. & Recon. Surg., 73(3): 474; 1984.

Helen Bibleheiner, "Dealing with a Wound that Drains 1.5 Liters per Day," RN Aug. 1986.

Peter Schwab, "Primary Closure of the Perineal Wound After Proctectomy" Mayo Clin. Proc., Mar. 1974, vol. 49.

Garcia–Rinaldi, et al. *Improving the Efficiency of Wound Drainage Catheters,* source not known, 1975, pp. 372–373.

Raffl, et al., *The Five Year Survival Rate for Gastric Cancer: Statistical Study from Syracuse Medical Center,* Cancer, 6:756–759, Jul. 1953.

Raffl, et al. *The Use of Negative Pressure Under Skin Flaps After Radical Mastectomy,* Ann. Surg. 136: 1048, Dec. 1952.

Bier A. "Hyperemia by suction apparatus", Hyperemia as a Therapeutic Agent, Chicago, IL, Roberts Publishing; 1905: 74–85.

Defranzo, Anthony J., et al., "Vacuum–Assisted Closure for the Treatment of Degloving Injuries." Plastic and Reconstructive Surgery 104(7) 2145–48: (1999).

Hartnett, Jacqueline M., "Use of Vacuum–Assisted Wound Closure in Three Chronic Wounds", JWOCN 25 (6) 281–290 (1998).

Hidden Interest—A Special report; When Physicians Double as Entrepreneurs. The New York times. p. 1. Nov. 30, 1999.

M.J. Morykwas and L.C. Agrenta, "Techniques in Use of V.A.C. Treatment (in English)", Acta Chir. Austriaca Supplement Nr. 150, 1998, p. 3–4.

Meara, John G. et al., "Vacuum–Assisted Closure in the Treatment of Degloving Injuries". Annals of Plastic Surgery 42(6) 589–594 (1999).

Mendez–Eastman, Susan., "Use of Hyperbaric Oxygen and Negative Pressure Therapy in the Multidisciplinary Care of a Patient with Nonhealing Wounds". JWOCN 26(2) 67–79 (1999).

Mendez–Eastman, Susan., "When wounds won't heal", RN 20–24 (1998).

Molnar, Joseph A., et al., "Single–Stage Approach to Skin Grafting the Exposed Skull", Plastic and Reconstructive Surgery 105(1): 174–177 (2000).

Morykwas J. Argenta LC. Nonsurgical modalities to enhance healing and care of soft tissue wounds. Journal of the Southern Orthopaedic Association 1997; 6: 279–88.

Morykwas, Michael J., et al., "Use of Subatmospheric Pressure to Prevent Progression of Partial–thikness Burns in a Swine Model". Journal of Burn Care & Rehabilitation 20 (1 Part 1): 15–21 (1999).

Morykwas, Michael J., et al., "Use of Subatmospheric Pressure to Prevent Doxorubicin Extravasation Ulcers in a Swine Model". Journal of Surgical Onccology 72: 14–17 (1999).

Obdeijn, Miryam C., et al., "Vacuum–Assisted Closure in the Treatment of Poststemotomy Mediastinitis". Ann Thorac Surgery 68 2358–60 (1999).

Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41–50 (1999).

Registration No. 1982349. Owner, KCI Inc., 3440 E. Houston Street San Antonio Texas 78219. Source: United States Patent and Trademark Office official website. Filing date May 1, 1995 Registration Date Jun. 25, 1996.

Rosser, Charles J., et al., "A New Technique to Manage Perineal Wounds". Infections in Urology 13(2) 45–47 (2000).

Schneider, Andrew M., et al., "A New and Reliable Method of Securing Skin Grafts to the Difficult Recipient Bed". Plastic and reconstructive Surgery 102(4) 1195–98 (1998).

Volkov LA. Ispol'zovanie vakuum–drenazhnoi sistemy v khirurgicheskoi praktike. [Use of vacuum–drainage system in surgical practice]. Russian. Klinicheskaia Khirurgila. 1973;7: 54–55, with English Translation.

Smith LA, Barker DE, Chase CW, et al. Vacuum Pack Technique of Temporary Abdominal Closure: A Four–Year Experience. Amer Surg 1997; 63: 1102–8.

Webster, J.G., "Prevention of Pressure Sores", © IOP Publishing Ltd 1991, The Adam Hilger Series on Biomedical Engineering, pp. 199–223.

Garcia–Velasco, M., et al., "Compression Treatment of Hypertrophic Scars in Burned Children", The Canadian Journal of Surgery, V.21, No. 5, Sep. 1978, pp. 450–452.

Rose, M.P., et al., "The Clinical Use Of A Tubular Compression Bandage, Tubigrip, for Burn–Scar Therapy: A Critical Anaylis", Burns (1985) 12, 58–64.

Murray, Y., "Tradition Rather Than Cure", Wound Care, Nursing Times, Sep. 21, vol. 94, No. 38, 1988 with German translation.

Spurlock, Gareth, "The Management of Open Joint Injuries", Wound Management, Veterinary Clinics of North American Equina Practice, vol. 5, No. 3, Dec. 1989.

Tittel, K., et al., "VariDyne—new standards in postoperative wound drainge", Jahrgang 14 (1988), Nr. 2, Apr., vol. 14 (1988), No. 2, pp. 104–107.

Queen, D., et al., "The preclinical evaluation of the Water Vapour Transmission Rate Through Burn Wound Dressings", Biomaterials 1987 vol. 8, Sep., pp. 367–371.

Wood, R.A.B., et al., "Foam Elastomer Dressing in the Management of Open Granulating Wounds: Experience with 250 Patients", Br. J. Surg., vol. 64 (1977), pp. 554–557.

Waymack, J.P., et al., "An Evaulation of Aquaphor Gauze Dressing in Burned Children", Burns (1986) 12, 443–448.

Winter, George D., "Epidermal Wound Healing Under a New Polyurethane Foam Dressing (Lyofoam)", Plastic & Reconstructive Surgery, Nov. 1975, Vo. 56, No. 5, pp. 531–537.

Thomas, S., et al., "Comparative Review of the Properties of Six Semipermeable Film Dressings", The Pharmaceutical Journal, Jun. 18, 1988, pp. 785–789.

Baker, B., "Abundance of Web Sites on Wound Care Management", Family Practice News, Mar. 1, 2000, pp. 52.

Cosker, T., et al., "Choice of Dressing Has a Major Impact on Blistering and Healing Outcomes in Orthopaedic Patients", Journal of Wound Care, Vo. 14, No. 1, Jan. 2005, pp. 27–29.

Barillo, D., et al., "Management of Burns to the Hand", Wounds 15,(1):4–9, 2003 Health Management Publications, Inc., Posted Feb. 12, 2003.

Medical Technology & Innovation, "Medical Technology is Extending Life, Reducing Costs", vol. 1, Issue 46, Dec. 4, 2000.

Chariker–Jeter Status Link from the website www.trademark.com/cbi–bin/tmlist, Oct. 14, 2005, 1 page.

Bluesky Medical Support, printout of webpages www.woundvacuum.com/Standard%20Pages/support.htm. Oct. 11, 2005, pp. 1–3.

Davies, J.W.L, "Synthetic materials for covering burn wounds: Progress towards perfection. Part I. Short term dressing materials", Burns, Nov.1983;10(2), 94–103.*

Lamke, L.O., et al., "The evaporative water loss from burns and the water–vapour permeability of grafts and artificial membranes used in the treatment of burns", Burns, 3, 159–165, 1977.*

Barnett, A., et al., "Comparison of Synthetic Adhesive Moisture Vapor Permeable and Fine Mesh Gauze Dressing for Split–Thickness Graft Donor Sites", The American Journal of Surgery, vol. 145, Mar. 1983, pp. 379–381.*

Alper, J., et al., "Moist wound healing under a vapor permeable membrane", Journal of the American Academy of Dermatology, vol. 8, No. 3, Mar. 1983, 347–353.*

James, J.H., et al., "The use of Opsite, A Vapour Permeable Dressing, on Skin Donor Sites", British Journal of Plastic Surgery (1975), 28, 107–110.*

Nahas, L.F., et al., "Use of Semipermeable Polyurethane Membrane for Skin Graft Dressings", Plastic and Reconstructive Surgery, Jun. 1981, pp. 791–792.*

Edlich, R.F., et al., "Surgical Devices in Wound Healing Management", Wound Healing Biochemical & Clinical Aspects, W.B. Saunders Company, © 1992, pp. 581–599.*

Orr, RK, et al., "Early Discharge After Mastectomy. A Safe Way of Diminishing Hospital Cost", Am Surg. Mar. 1987; 53(3) Abstract.

Otolaryngology, Head and Neck Surgery, The C.V. Mosby Company, © 1986, pp. 1716, 1724 and 2521.

Otolaryngology, vol. III, Head and Neck, W.B. Saunders Company, © 1980, pp. 2963.

Lore, Jr., J.M., "An Atlas of Head and Neck Surgery", Second Edition, vol. II, W.B. Saunders Company, © 1973.

Swearingen, Pamela L., The Addison Wesley Photo–Atlas of Nursing Procedures—Administering Medications and Monitoring Fluids—Managing Gastrointestinal Procedures—Managing Gastric Tubes, Copyright 1984.

Dewan, P.A., et al., "An Alternative Approach To Skin Graft Donor Site Dressing", Aust. N.Z. J. Surg. 1986, 56, 509–510.

Banwell, P, et al., "Topical Negative Pressure TNP Focus Group Meeting", Proceedings, London, UK 2003, 232 pages.*

Proceedings from the 2003 National V.A.C.® Education Conference, supplement to the Apr. 2004 WOUNDS, 38 pages.*

Dieu, T., et al., "Too Much Vacuum–Assisted Closure", ANZ J. Surg. 2003; 73: 1057–1060.*

Chester, D., et al., "Adverse Alteration of Wound Flora with Topical Negative–Pressure Therapy: A Case Report", British Journal of Plastic Surgery, 2002, pp. 510–511.*

Alvarez, A., et al., "Vacuum–Assisted Closure for Cutaneous Gastrointestinal Fistula Management", Gynecologic Oncology, 80, 413–416 (2001).*

Nienhuijs, S.W., et al., "Can Topical Negative Pressure Be Used To Control Complex Enterocutaneous Fistulae?", Journal of Wound Care, V. 12, No. 9, Oct. 2003, pp. 343–345.*

Maddin, W. Stuart, et al., "The Biological Effects of a Pulsed Electrostatic Field with Specific Reference to Hair", Pharmacology and Therapeutics, Jul.–Aug. 1990, V. 29, No. 6, pp. 446–500.*

Peacock, Erle, Third Edition Would Repair, "Repair of Skin Wounds", W.B. Saunders Company 1984, 172–175.*

Morykwas, M. and Argenta, L., "Use of Negative Pressure to Increase the Rate of Granulation Tissue Formation in Chronic Open Wounds", The FASEB Journal, Experimental Biology '93, New Orleans, Louisiana, Mar. 28–Apr. 1, 1993, 800.*

Orringer, Jay, et al., "Management of Wounds in Patients with Complex Enterocutaneous Fistulas", Surgery, Gynecology & Obstetrics, Jul. 1987, V. 165, pp. 79–80.*

Lohman, R., et al., "DISCUSSION: Vacuum Assisted Closure: Microdeformations of Wounds and Cell Proliferation", Plastic and Reconstructive Surgery, Oct. 2004, pp. 1097–1098.*

Defranzo, A.J., et al., "109: Use of Sub–Atmospheric Pressure for Treatment of Gunshot Injuries", Plastic Surgical Forum, V. XXIII, Los Angeles, CA, Oct. 14–18, 2000, pp. 180–181.*

Marks, M., et al., "Management of Complex Soft Tissue Defects in Pediatric Patients Using the V.A.C. Wound Closure", Plastic Surgical Forum, V. XXI, Boston, MA, Oct. 3–7, 1998, pp. 215–216.

Morykwas, M. and Argenta, L., "Use of Negative Pressure to Prevent Progession of Partial Thickness Burns", American Burn Association, V. 26, 26$^{th}$ Annual Meeting, Apr. 20–23, 1994, Orlando, Florida, pp. 157.

Morykwas, M. and Argenta, L., "Vacuum Assisted Closure (VAC Therapy) for Secondary Closure of Dehisced and Infected Wounds", Wound Repair and Regeneration, Jul.–Sep. 1995, pp. 361.

Morykwas, M. and Argenta, L., "Treatment of Burned Extremities Using Vacuum Therapy (The V.A.C.)", Wound Repair and Regeneration, V. 3, N. 3, Jul.–Sep. 1995, pp. 367.

Webb, L. and Morykwas, M., et al., "The Use of Vacuum–Assisted Closure in Composite Wound Management", The Third Riva Congress, Current Perspectives in Fracture Management and Orthopaedic Reconstruction, May 10–14, 2000, Italy, pp. 137.

Morykwas, M. and Webb, L., "Sub–Atomspheric Pressure for the Treatment of Lower Extremity Wounds", The Third Riva Congress, Current Perspectives in Fracture Management and Orthopaedic Reconstruction, May 10–14, 2000, Italy, pp. 135–136.

Argenta, L., et al., "Use of V.A.C. for Treatment of Dehisced Sternal Incisions", Plastic Surgical Forum, V. XXIII, Los Angeles, CA, Oct. 14–18, 2000, pp. 172–174.

Morykwas, M., et al., "Isolated Muscle Flap Survival with Complete Venous Occlusion: Varying Delay in External Application of Sub–atmospheric Pressure", Plastic Surgical Forum, V. XXI, Boston, MA, Oct. 3–7, 1998, pp. 237.

Morykwas, M., et al., "Vacuum–Assisted Closure: A New Method for Wound Control and Treatment: Animal Studies and Basic Foundation", Annals of Plastic Surgery, V. 39, N. 6, Jun. 1997, pp. 553–562.

Argenta, L. and Morykwas, M., "Vacuum–Assisted Closure: A New Method for Wound Control and Treatment: Clinical Experience", Annals of Plastic Surgery, V. 38, N.6, Jun. 1997, pp. 563–576.

Morykwas, M. and Argenta, L., "V.A.C. Experience and Difficult Wounds", des Journes Regionales des Plaies et Cicatrisations, Sep. 22–23, 1997, pp. 76–90.

Genecov, D., et al., "A Controlled Subatmospheric Pressure Dressing Increases the Rate of Skin Graft Donor Site Reepithelialization", Annals of Plastic Surgery, V. 40. N. 3, Mar. 1998, 219–225.

Morykwas, M. and Argenta, L., "Techniques in Use of V.A.C.™ Treatment", ACA–Acta Chir. Austriaca, Supplement Nr. 150, 1998, pp. 3–4.

Morykwas, M. and Argenta, L., "Use of the V.A.C.™ For Treatment of a Traumatic Left Hip Disarticulation", ACA–Acta Chir. Austriaca, Supplement Nr. 150, 1998, pp. 24–25.

Morykwas, M., et al., "Use of Subatmospheric Pressure to Prevent Progression of PartialpThickness Burns in a Swine Model", Journal of Burn Care & Rehabilitation, Jan./Feb. 1999, pp. 15–21.

Banwell, P., et al., "Application of Topical Sub–Atmospheric Pressure Modulates Inflammatory Cell Extravasation in Experimental Partial Thickness Burns", Wound Repair and Regeneration, Jul./Aug. 1999, V. 7, N. 4, pp. A286–287.

Morykwas, M., et al., "Use of Subatomospheric Pressure to Prevent Doxorubicin Extravasation Ulcers in a Swine Model", Journal of Surgical Oncology, 1999; 72:14–17.

Banwell, P., et al., "Dermal Perfusion in Experimental Partial Thickness Burns: The Effect of Topical Subatmospheric Pressure", Jan./Feb. 2000, V. 21, N. 1, Part 2, Burn Care & Rehabilitation.

Mooney, J., et al., "Treatment of Soft Tissue Defects in Pediatric Patients Using the V.A.C.™ System", Clinical Orthopaedics and Related Research, No. 376, Jul. 2000, pp. 26–31.

Morykwas, M., et al., "The Effect of Externally Applied Subatmospheric Pressure on Serum Myoglobin Levels After a Prolonged Crused/Ischemia Injury", The Journal of TRAUMA Injury, Infection and Critical Care, Sep. 2002, V. 53, N.3, pp. 537–540.

Molnar, J., et al., "Acceleration of Integra Incorporation in Complex Tissue Defects with Subatmospheric Pressure", Plastic and Reconstructive Surger, Apr. 15, 2004, pp. 1339–1346.

Morykwas, M. and Argenta, L., "Nonsurgical Modalities to Enhance Healing and Care of Soft Tissue Wounds", Journal of the Southern Orthopaedic Association, V. 6, N. 4, 1997, pp. 279–288.

Schneider, A., et al., "A New and Reliable Method of Securing Skin Grafts to the Difficult Recipient Bed", Plastic and Reconstructive Surgery, Sep. 1998, pp. 1195–1198.

Rosser, C., et al., "A New Technique to Manage Perineal Wounds", Infections in Urology, Mar./Apr. 2000, V. 13, N.2, pp. 45–47 & 56.

Defranzo, A.J., et al., "The Use of Vacuum–Assisted Closure Therapy for the Treatment of Lower–Extremity Wounds with Exposed Bone", Plastic and Reconstructive Surgery, Oct. 2001, V. 108, N. 5, pp. 1184–1191.

Morykwas, M., "The Use of The V.A.C. Wound Treatment System for Acute and Subacute Wounds", Plaies & Cicatrices, Would Closure Healing, Apr. 21, 22 and 23, 1999.

Webb, L., et al., "Negative Pressure Wound Therapy in the Management of Orthopedic Wounds", Ostomy Wound Management, Apr. 2004, V. 50, Issue 4A (Suppl), pp. 26–27.

Webb, L., et al., "Wound Management With Vacuum Therapy", English abstract from website printout and German article, http://www.ncbi.nlm.nih.gov/entrez/query.fcgi?cmd=Retrieve &db=pubmed&dot=Abstra..., Dec. 2, 2004, 2 pages website printout, German article, Oct. 2001, pp. 918–926.

Webb, "New Techniques in Wound Management: Vacuum–Assisted Wound Closure", Journal of the American Academy of Orthopaedic Surgeons, V. 10, N. 5, Sep./Oct. 2002, pp. 303–311.

Morykwas, M. and Argenta, L., "Sub–Atmospheric Pressure Wound Treatment and Cultured Keratinocyte Allografts", Cultured Human Keratinocytes and Tissue Engineered Skin Substitutes, © 2001 Georg Thieme Verlag, pp. 343–346.

Molnar, J., et al., "Single–Stage Approach to Skin Grafting the Exposed Skull", Plastic and Reconstructive Surgery, Jan. 2000, V. 105, N. 1, 174–177.

Scherer, L, et al., "The Vacuum Assisted Closure Device: A Method of Securing Skin Grafts and Improving Graft Surival", Arch. Surg., V. 137, Aug. 2002, pp. 930–934.

Defranzo, A., et al., "Vacuum–Assisted Closure for the Treatment of Degloving Injuries", Plastic and Reconstructive Surgery, Dec. 1999, V. 104, N. 7, pp. 2145–2148.

Miller, P., et al., "Late Fascial Closure in Lieu of Ventral Hernia: The Next Step in Open Abdomen Management", the Journal of TRAUMA Injury, Infection and Critical Care, Nov. 2002, V. 53, N. 5, pp. 843–849.

Betancourt, S., "A Method of Collecting the Effluent From Complicated Fistula of the Small Intestine", 1986, p. 375.

DORLAND'S Illustrated Medical Dictionary, Twenty–Fifth Edition, 1974, pp. 1112.

Hopf, H., et al., "Adjuncts to preparing wounds for closure Hyperbaric oxygen, growth factors, skin substitutes, negative pressure wound therapy (vacuum–assisted closure)", Foot Ankle Clin N Am 6, 2001, pp. 661–682.

Montgomery, B., "Easy Dressing of Large, Draining Abdominal Wounds Using Moisture Vapor–Permeable Film", pp. 417–418, Techniques for Surgeons, Wiley Medical Publication, © 1985.

Davydov, Y., et al., "Pathogenic Mechanism of the Effect of Vacuum Therapy on the Course of the Wound Process", Jun. 1990, 15 pages of English Translation.

Borzov, M., et al., "Vacuum Therapy of Some Skin Disease", Vestnik dermatologii venerologii, n. 8, Aug. 1965, pp. 50–56,(10 pages of English translation by R. McElroy.

Herrmann, L., et al., "The Pavaex (Passive Vascular Exercise) Treatment of Obliterative Arterial Diseases of the Extremeties", The Journal of Medicine, Dec. 1933, pp. 524–529.

Herrmann, L., et al., "Passive Vascular Exercises: Treatment of Peripheral Obliterative Arterial Diseases by Rhythmic Alternation of Environmental Pressure", Archives of Surgery, v. 29, n. 5, Nov. 1934, pp. 697–704.

Sturr, R., Evaluation of Treatment of Peripheral Vascular Disease by Alternating Positive and Negative Pressure, Philadelphia, Archives of Physical Therapy, Sep. 1938, pp. 539–543.

Balin, A., et al., "Oxygen Modulates Growth of Human Cells at Physiologic Partial Pressures", Laboratory for Investigate Dermatology, J. Exp. Med.©, the Rockefeller University Press, v. 160, Jul. 1984, pp. 152–166.

Saran Resins and Films, "Fresh Thinking". website printout, 6 pages, Jan. 20, 2004.

Bluesky Medical, "A Leader in Suction Technology—Wound Drainage Experts", printout of website, 55 pages, Apr. 8, 2003, www.blueskymedical.com.

Garcia–Rinaldi, R., et al., "Improving the Efficiency of Wound Drainage Catheters", v. 130, Sep. 1975, pp. 372–373.

Davydov, et al., "Would Healing Under the Conditions of Vacuum Draining", Khirurgiia (Mosk). 1992, (7–8): 21–6 (with English translation by Scientific Translation Services).

Davydov, et al., "Vacuum therapy in the treatment of acute suppurative diseases of soft tissue and suppurative wounds", Vestn. Khir, Sep. 1988 (with English translation by Ralph McElroy Co.).

Baker, B., "Negative–Pressure Therapy Looks Promising", Skin & Allergy News, Feb. 2000, p. 14.

McCallon, S., et al., "Vacuum–Assisted Closure versus Saline–Moistened Gauze in the Healing of Postoperative Diabetic Foot Wounds", Ostomy Wound Management, Aug. 2000, v.46, Issue 8. pp. 28–34.

Clinicians' Pocket Guide To Chronic Wound Repair, Wound Healing Publications, Second Edition, © 1992, 106 pages.

Biblehimer, H., "Dealing with A Wound That Drains 1.5 Liters A Day", RN, Aug. 1986, pp. 21–22.

Morykwas, M.J., et al., "Use of Negative Pressure to Increase the Rate of Granulation Tissue Formation in Chronic Open Wounds", The FASEB Journal, Apoptosis and Necrosis (799–800), Feb. 19, 1993.

Orringer, J.S., et al., "Management of Wounds in Patients with Complex Enterocutaneous Fistulas", Surgery, Gynecology & Obstetrics, Jul. 1987, vol. 165.

Swearingen, P.L., "The Addison–Wesley Photo–Atlas of Nursing Procedures", 9 pages, © 1984.

Mulder, G.D, et al., Clinicans' Pocket Guide to Chronic Wound Repair, Wound Healing Publications Second Edition, 1992, pp. 1–107.

Peacock, E.E., Jr., Wound Repair:, Repair of Skin Wounds, 1984, pp. 172–175.

Jeter, Katherine F., et al., "Managing Draining Wounds and Fistulae: New and Established Methods", Chronic Wound Care, 1990, pp. 240–246.

Kohlman, P., et al., "Pouching Procedure To Collect Drainage From Around A Biliary Drainage Catheter", Ostomy/Wound Management, Nov./Dec. 1991, pp. 47–50, V. 37.

Alper, J., "Recent Advances in Moist Wound Healing", Southern Medical Journal, Nov. 1986, pp. 1398–1404, V. 79, N.11.

Untitled Article, The Lancet, Jun. 14, 1952, pp. 1175–1176.

Putney, F., "The Use of Continuous Negative Pressure After Laryngectomy and Radical Neck Dissection", Surgery, Gynecology & Obstetrics, Aug. 1956, pp. 244–246.

Pleupump MK II, printouts from websites, www.xenamedical.se and www.landstinget.sormland.se, Aug. 14, 2001 (12 pages).

Brummelkamp, W., et al., "High–vacuum Drainage and Primary Perineal Wound Closure in Abdominoperineal Excision of the Rectum", The Netherland Journal of Surgery, 1991, pp. 236–239, V. 43, No. 6.

Engdahl, O., et al., "Quantification of Aspirated Air Volume Reduces Treatment Time in Pneumothorax", Eur Respir J., 1990, 3, pp. 649–652.

Spengler, M., et al., "Performance of Filtered Sump Wound Drainage Tubes", Surgery, Gynecology & Obstetricsq, Mar. 1982, pp. 333–336, vol. 154.

Hallstrom, B., et al., "Postoperative Course After Total Hip Arthroplasty: Wound Drainage Versus No Drainage", Orthopaedic Review, Jul. 1992, pp. 847–851.

Miles, W., et al., "A Method of Performing Abdominoperineal Excision for Carcinoma of the Rectum and of the Terminal Portion of the Pelvic Colon", The Lancet, Dec. 19, 1908, pp. 1812–1813.

Benjamin, P., "Faeculent Peritonitis: A Complication of Vacuum Drainage", Br. J. Surg., 1980, pp. 453–454, vol. 67.

Sagi, A., et al., "Burn Hazard From Cupping—An Ancient Universal Medication Still in Practice", Burns, 1988, pp. 323–325, vol. 14, No. 4.

Agrama, H., et al., "Functional Longevity of Intraperitoneal Drains", The American Journal of Surgery, Sep. 1976, pp. 418–421, vol. 132.

Magee, C., et al., "Potentiation of Wound Infection by Surgical Drains", The American Journal of Surgery, May 1976, pp. 547–549, vol. 131.

Birdsell, D., et al., "The Theoretically Ideal Donor Site Dressing",Annals of Plastic Surgery, Jun. 1979, pp. 535–537, vol. 2, No. 6.

Cruse, P., et al., "A Five–Year Prospective Study of 23,649 Surgical Wounds", Surgical Wounds/Cruse and Foord, Aug. 1973, pp. 206–210, vol. 107.

Aubrey, D., et al., "Treatment of the Perineal Wound After Proctectomy by Intermittent Irrigation", Arch. Surg., Oct. 1984, pp. 1141–1144, vol. 119.

Mayo, C., "The One–Stage Combined Abdominoperineal Resection for Carcinoma of the Rectum, Rectosigmoid and Sigmoid", Surgical Clinics of North America, Aug. 1939, pp. 1011–1019.

Draper, J., "Make the dressing fit the wound", Nursing Times, Oct. 9, 1985, pp. 32–35.

Schumann, D., et al., "Preoperative Measures to Promote Wound Healing", Nursing Clinics of North America, Dec. 1979, pp. 683–699, vol. 14, No. 4.

Besst, J., et al., "Wound Healing—Intraoperative Factors", Nursing Clinics of North America, Dec. 1979, pp. 701–711, vol. 14, No. 4.

Cooper, D., et al., "Postsurgical Nursing Intervention as an Adjunct to Wound Healing", Nursing Clinics of North America, Dec. 1979, pp. 713–725, Nursing Clinics of North America, vol. 14, No. 4.

O'Byrne, C., "Clinical Detection and Management of Postoperative Wound Sepsis", Nursing Clinics of North America, Dec. 1979, pp. 727–741, vol. 14, No. 4.

Keith, C., "Would Management Following Head and Neck Surgery", Nursing Clinics of North America, Dec. 1979, pp. 761–778, vol. 14, No. 4.

Tenta, L., et al., "Suction Drainage of Wounds of the Head and Neck", Surgery, Gynecology. & Obstetrics, Dec. 1989, p. 558, vol. 169.

Firlit, C., et al., "Surgical Wound Drainage: A Simple Device for Collection", journal of Urology, Aug. 1972, pp. 327, vol. 108.

Worth, M., et al., "The Effectiveness of Bacterial Filtration in Vented Wound Drains", Journal of Surgical Research, 1979, pp. 405–407, 27.

Flynn, M., et al., "Promoting Wound Healing: Wound Healing Mechanisms", American Journal of Nursing, Oct. 1992, pp. 1544–1558.

Hilton, P., "Surgical Wound Drainage: A Surgery of Practices Among Gynaecologists in the British Isles", British Journal of Obstetrics and Gynaecology, Oct. 1988, pp. 1063–1069, vol. 95.

Milsom, I., et al., "An Evaluation of a Post–Operative Vacuum Drainage System", Current Medical Research and Opinion, 1979, pp. 160–164, vol. 6, No. 2.

Fox, J., et al., "The Use of Drains in Subcutaneous Surgical Procedures", The American Journal of Surgery, Nov. 1976, pp. 673–674, vol. 132.

Hilten, L., et al., "Primary Closure of Perineal Wound After Protocolectomy or Rectal Excision", Acta Chir Scand 137, 1971, pp. 467–469.

Laners, R., "An Improved Suction Device for Draining Wounds", Arch. Surg., May 1972, pp. 707, vol. 104.

Hugh, T., "Abdominal Wound Drainage", The Medical Journal of Australia, May 4, 1987, pp. 505.

Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley–Liss, Inc., pp. 257–265.

Bruno, P., "The Nature of Wound Healing", Nursing Clinics of North America, Dec. 1979, pp. 667–681, vol. 14, No. 4.

Bar–El, Y., et al., "Potentially Dangerous Negative Intrapleural Pressures Generated by Ordinary Pleural Drainage Systems", Chest, Feb. 2001, pp. 511–514, vol. 119, No. 2.

Agarwala, S., et al., "Use of Mini–Vacuum Drains in Small Surgical Wounds", Plastic and Reconstructive Surgery, Apr. 1998, pp. 1421–1422, vol. 101, n. 5.

Nasser, A., "The Use of the Mini–Flap Wound Suction Drain in Maxillofacial Surgery", Annals of the Royal College of Surgeons of England, 1986, pp. 151–153, vol. 68.

Lumley, J., et al., "The Physical and bacteriological Properties of Disposable and Non–Disposable Suction Drainage Units in the Laboratory", Br. J. Surg, 1974, pp. 832–837, vol. 61.

Britton, B., et al., "A Comparison Between Disposable and Non–disposable Suction Drainage Units: A Report of a Controlled Trial", Br. J. Surg., 1979, pp. 279–280, vol. 66.

Fay, M., "Drainage Systems: Their Role in Wound Healing", AORN Journal, Sep. 1987, pp. 442–451, vol. 46, No. 3.

Orgill, D., "Curent Concepts and Approaches to Would Healing", Critical Care Medicine, Sep. 1988, pp. 899–908, vol. 16, No. 9.

"Making Sense of Wound Drainage", Nursing Times, Jul. 5, 1989, pp. 40–42, vol. 85, No. 27.

Harkiss, K., "Leg Ulcers Cheaper in the Long Run", Community Outlook, Aug. 1985, pp. 19, 21, 22, 24 & 26.

Westaby, S. (Editor), "Wound Care No. 43: Which Dressing and Why", Nursing Times Jul. 21, 1982, pp. 41–44.

Cobb, J., "Why Use Drains", The Journal of Bone and Joint Surgery, Nov. 1990, pp. 993–995, vol. 72–B, No. 6.

Garcia–Rinaldi, R., "Improving the Efficiency of Wound Drainage Catheters", the Journal of Surgery, Sep. 1975, pp. 372–373, vol. 130.

Silvis, R., et al., "The Use of Continuous Suction Negative Pressure Instead of Pressure Dressing", Annals of Surgery, Aug. 1955, pp. 252–256, vol. 1142, No. 2.

Van Way, C., "Prevention of Suction–Induced Gastric Mucosal Damage in Dogs", Gastric Suction, 1987, pp. 774–777, vol. 15, No. 8.

Curtin, L., "Wound Management: Care and Cost—An Overview", Nursing Management, Feb. 1984, pp. 22–25, vol. 15.

Royle, G., et al., "Disposable Drains", Annals of the Royal College of Surgery of England, 1984, 1 page, vol. 66.

Meehan, P., "Open Abdominal Wounds: A Creative Approach to a Challenging Problem", Pregressions, 1992, pp. 3–11, vol. 4, No. 2.

Stansby, G., et al., "Vacuum Drainage of Groin Wounds After Vascular Surgery", Br. J. Surg., Oct. 1990, pp. 1194–1195, vol. 77, No. 10.

Edlich, R., et al., "Evaluation of a New, Improved Surgical Drainage System", The American Journal of Surgery, Feb. 1985, pp. 295–298, vol. 149.

Broader, J., et al., "Management of the Pelvic Space After Proctectomy", Br. J. Surg., 1974, pp. 94–97, vol. 61.

Ayoub, M., et al., "A study of cutaneous and intracompartmental limb pressures associated with the combined use of tourniquets and plaster casts", May 1986, pp. 497, vol. 68–B, No. 3.

Cooper, D., "Optimizing Wound Healing: A Practice Within Nursing's Domain", Nursing Clinics of North America, Mar. 1990, pp. 165–179, vol. 25, No. 1.

Hollis, H., et al., "A Practical Approach to Wound Care in Patients With Complex Enterocutaneous Fistulas", Surgery, Gynecology & Obstetrics, Aug. 1985, pp. 179–181, vol. 161.

Fingerhut, A., "Passive vs. Closed Suction Drainage After Perineal Would Closure Following Abdominoperineal Rectal Excision for Carcinoma", Dis Colon Rectum, Sep. 1995, pp. 926–932, vol. 38, No. 9.

Alper, Joseph C., et al., "The In Vitro Response of Fibroblasts to the Fluid that Accumulates Under a Vapor–Permeable Membrane". Journal of Investigative Dermatology, 84:513–515, 1985.

Alper, Joseph C., et al, "Use of the Vapor Permeable Membrane for Cutaneous Ulcers: Details of application and side effects", Journal of the American Academy of Dermatology, vol. 11, No. 5, Part I, Nov. 1984, pp. 858–866.

Angermeier, Marla C., et al., "Vapor–Permeable Membrane Therapy for Ulcers of Osteomyelitis", J. Dermatol. Surg. Oncol,, 10:5, May 1984, pp. 384–388.

Bourke, et al., "Comparison Between Suction and Corrugated Drainage After Simple Mastectomy: A Report on Controlled Trial", Br. J. Surg., vol. 63, 1976, pp. 67–69.

Eaglstein, William H., "Experinces with Biosynthetic Dressings", Journal of the American Academy of Dermatology, vol. 12, No. 2, Part 2, Feb. 1985, pp. 434–440.

Falanga, Vincent, et al., "A Therapeutic Approach to Venous Ulcers", Journal of the American Academy of Dermatology, vol. 14, No. 5, Part 1, May 1986, pp. 777–784.

Friedman, S., et al., "Treatment of Dermabrasion Wounds with a Hydrocolloid Occlusive Dressing", Arch Dermatol, vol. 121, Dec. 1985, pp. 1486–1487.

Friedman, Stephen J., et al., "Management of Leg Ulcers with Hydrocolloid Occlusive Dressing", Arch. Dermatol., vol. 120, Oct. 1984, pp. 1329–1336.

Holland, K.T., et al., "A Comparison of the In Vivo Antibacterial Effects of OpSite, Tegaderm and Ensure dressings", Journal of Hospital Infection, 1985, 6, pp. 299–303.

Jeter, Katherine F., et al., "Wound Dressings of the Nineties: Indications and Contraindications", Clinics in Podiatric Medicine and Surgery, vol. 8, No. 4, Oct. 1991, pp. 799–816.

Katz, Stuart, et al., "Semipermeable Occlusive Dressings", Arch Dermatol., vol. 122, Jan. 1986, pp. 58–62.

Lewis, R.T., "Knitted Polypropylene (Marlex) Mesh in the Repair of Incisional Hernias", The Canadian Journal of Surgery, vol. 27, No. 2, Mar. 1984, pp. 155–157.

Satas, Donatas, "Handbook of Pressure–Sensitive Adhesive Technology", Silicone Release Coatings, Van Nostand Reinhold Company, 1982, pp. 384–402.

Turner, T.D., "A Look at Wound Dressings", Health and Social Service Journal, May 4, 1979, pp. 529–531.

Turner, T.D., et al., "Wound Management Product Selection", Journal of Sterile Services Management, Apr. 1985, pp. 3–6.

Varghese, Mathew C., et al., "Local Environment of Chronic Wounds Under Synthetic Dressings", Arch. Dermatol, vol. 122, Jan. 1986, pp. 52–57.

Viljanto, J., "Cellstic: A Device for Wound Healing Studies in Man. Description of the Method", Journal of Surgical Research, 20, 1976, pp. 115–199.

Wagner, S.A., et al., "An individualized Plastic Intraoral Device for the Collection of Human Parotid Saliva", International Journal of Clinical Pharmacology, Therapy and Toxilogy, Vo. 22, No. 5, 1984, pp. 236–239.

Wilson, John L., et al., "Loss of Blood Volume in Spinal Surgery with Use of Closed Wound Suction: An Experimental Study", Southern Medical Journal, Jul. 1968, pp. 761–763.

Avery, C., et al., "Negative pressure wound dressing of the radial forearm donor site", International Journal of Oral Maxillofacial Surgery, 2000; 29, pp. 198–200.

Armstrong, David G., et al., "Outcomes of Subatmospheric Pressure Dressing Therapy on Wounds of the Diabetic Foot", Ostomy/Wound Management 2002; 48(4): 64–68.

Brown, Karen M., et al., "Vacuum–Assisted Closure in the Treatment of a 9–Year–Old Child with Severe and Multiple Dog Bite Injuries of the Thorax", Society of Thoracic Surgeons, 2001; 72:1409–1410.

Catarino, Pedro A., et al., "High–Pressure Suction Drainage via a Polyurethane Foam in the Management of Poststernotomy Mediastinitis", Ann Thorac Surg 2000; 70:1819–5.

Clinical Management Extra, Negative Pressure Therapy, Advances in Skin & Wound Care, Nov./Dec. 2001, vol. 14, No. 6, p. 321–322.

Cooper, Susan Mary, "Topical negative pressure in the treatment of pressure ulcers", Letters posted in the Journal of the American Acad of Dermatology, Aug., Part 1, 1999, p. 280.

Davydov, I.A., et al., "Concept of clinio–biological control of the wound", Vestnik khirurgii imeni I.I. Grekova, v. 146, issue 2, 1991, (with English translation).

de la Torre, Jorge I., MD, et al., "Healing a Wound with an Exposed Herrington Road: A Case Study", Ostomy Wound Management, pp. 18–19, May 2002, vol. 48, Issue 5.

de Lange, M.Y., et al., "Vacuum–assisted closure: indications and clinical experience", Eur J Plast Surg (2000) 23:178–182.

Deva, Anand, K., et al., "Topical negative pressure in wound management", MJA, Vo. 173, pp. 128–131, Aug. 7, 2000.

Elwood, Eric T., et al., "Negative–Pressure Dressings in the Treatment of Hidradenitis Suppurativa", Ann Plast Surgery Jan. 2001; 46:49–51.

Evans, D. and Land, L., "Topical negative pressure for treating chronic wounds: a systematic review", British Journal of Plastic Surgery (2001), 54, 238–242.

Fabian, Thaddeus S., MD, "The Evaluation of Subatmospheric Pressure and Hyperbaric Oxygen in Ischemic Full–Thickness Wound Healing", The American Surgeon, Dec. 2000, vol. 66, 1136–1143.

Fenn, C.H. and Butler, P.E.M., "Abdominoplasty wound–healing complications: assisted closure using foam suction dressing", British Journal of Plastic Surgery (2001), 54, 348–351.

Giovannini, Uberto M., MD, "Negative Pressure for the Management of an Exposed Vascular Dacron Polyester Patch", Annals of Plastic Surgery, 47(5): 577–578, 2001.

Gustafsson, Ronny, MD, "Vacuum–assisted closure therapy guided by C–reactive protein level in patients with deep sternal wound infection", The Journal of Thoracic and Cardiovascular Surgery, vol. 123, No. 5, pp. 895–900, May 2002.

Gwan–Nulla, Daniel N., MD and Casal, Rolando S., MD, "Toxic Shock Syndrome Associated with the Use of the Vacuum–Assisted Closure Device", Ann Plastic Surgery 2001;47:552–554.

Hersh, Robert E., MD, et al., "The Vacuum–Assisted Closure Device as a Bridge to Sternal Wound Closure", Ann Plast Surg. 2001; 466: 250–254.

Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167–171.

Iusupov, I.N., et al., "Active drainage of a wound", Izdatelstvo Meditsina, St. Petersburg, Apr. 1987; 138(4):42–6 (with English Translation).

Joseph, Emmanuella, MD, et al., "A Prospective Randomized Trial of Vacuum–Assisted Closure Versus Standard Therapy of Chronic Nonhealing Wounds", WOUNDS 2000: 12(3): 60–67.

Josty, I.C., et al., "Vacuum–assisted closure: an altervative strategy in the management of degloving injuries of the foot", British Journal of Plastic Surgery (2001), 54, pp. 363–365.

Kostiucchenok, B.M., et al., "Vacuum Treatment in the Surgical Management of Suppurative Wounds", Izdatelstvo Meditsina, St. Petersburg, Sep. 1986; 137(9): 18–21 (with English Translation).

Kovacs, Laszlo, H., MD, "Necrotizing Fasciitis", Annals of Plastic Surgery, vol. 47, No. 6, Dec. 2001, pp. 680–682.

Kranser, Diane L., "Managing Wound Pain in Patients with Vacuum–Assisted Closure Devices", Ostomy Wound Management 2002; 48(5): 38–43.

Mendez–Eastman, Susan, RN, CPSN, CWCN, "Guidelines for Using Negative Pressure Wound Therapy", Advances in Skin & Wound Care, vol. 14, No. 6, pp. 314–320, Nov./Dec. 2001.

Mendez–Eastman, Susan, RN, CPSN, CWCN, "wound therapy", Nursing2002, vol. 32, No. 5, May, pp. 59–63.

Mooney, James F., III., "Treatment of Soft Tissue Defects in Pediatric Patients Using the V.A.C. TM System", Clinical Orthopedics and Related Research, No. 376, pp. 26–31, Jul. 2000.

Scheufler, O., et al., "Problem–adapted application of vacuum occlusion dressings: case report and clinical experience", Eur J. Plast Surg (2000) 23: 386–390.

Sposato, G., et al., "Ambulant vacuum–assisted closure of skin–graft dressing in the lower limbs using a portable mini–VAC device", British Journal of Plastic Surgery (2001), 54, 235–237.

Tang, Augustine T.M., et al., "Novel application of vacuum assisted closure technique to the treatment of sternotomy wound infection", European Journal of Cardio–Thoracic Surgery 17 (2000) 482–484.

Wu, S.H., et al., "Vacuum therapy as an intermediate phase in wound closure: a clinical experience", Eur J Surg (2000) 23:174–177.

Zhivotaev VM. Vacuum therapy of postoperative infected wounds of the urinary bladder, Klinicheskala Khiurgiia. 1970;5:36–39. (in Russian).

The Kremlin Papers . . . perspectives in wound care, "A collection of published studies complementing the research and innovation of wound care", Russian Medical Journal "Vestnik Khirurgii", 5 Russian Articles from 1986–1991, translated by BlueSky Medical Group Inc. © 2004.

Interlocutory decisions in Opposition proceedings (Wake Forest—Argenta, et al.) dated Apr. 19, 2004.

No–Wound is Too Big For Resourceful Nurses; Margaret Wooding–Scott et al., RN, Dec. 1988, 22–25.

Pathenogenic mechanism of the effect of vacuum therapy on the course of the wound process; Davydov, et al, Khirurgiia, Jun. 1990 (with English translation).

Vacuum Therapy in the Treatment of Suppurative Lactation Mastistis; Davydov, et al., Vestn. Khir., Nov. 1986 (with English translation).

Bacteriological and cytological evaluation of the vacuum therapy of suppurative wounds; Davydov, et al. Vestn. Khir., Oct. 1998 (with English translation).

Basis of the use of forced early secondary suture in the treatment of suppurative wounds by the vacuum therapy method; Davydov, et al., Vestn. Khir. Mar. 1990 (with English translation).

Vacuum therapy of some skin diseases; Borzov, et al., Vestn. Dermatol. Venerol., Aug. 1965 (with English translation).

Svedman, P., "A dressing allowing continuous treatment of a biosurface," IRCS Medical Science: Biomedical Technology; Clinical Medicine; Surgery and Transplantation, 7:221 (1979). (Exhibit D–407).

Johnson, F., "An Improved Technique for Skin Graft Placement Using a Suction Drain," Surgery, Gynecology & Obstetrics, p. 585–586, Dec. 1984, (Exhibit D132).

Davydov, Y., et al., "Bacteriological and Cytological Assessment of Vacuum Therapy of Purulent Wounds," Vestn. Khir., 48–52, English Translation by IRC, (Oct. 1988). (Exhibit D–290).

Davydov, Y., et al., "Vacuum Therapy in the Treatment of Purulent Lactation Mastitis," Vestn. Khir. p. 66–70, English translation by IRC, (Sep. 1986), (Exhibit D–292).

Meyer, W., et al., "Bier's Hyperemic Treatment," W.B. Saunders & Co., 1908 (Exhibit D246).

Chariker/Jeter, Spartanburg General Hospital Progress Notes, dated 1986, 25 pages, (Exhibit D–158).

Spahn/Hamaker slide entitled "Poor man's irrigation/vacuum dressing used since 1970's," (Exhibit D–135).

Svedman, "A dressing system allowing continuous treatment of a biosurface," IRCS Medical Science: Biomedical Technology; Clinical Medicine; Surgery and Transplantation, 7:221 (1979), with annotations.

Alexander, J.W., et al., "Clinical evaluation of epigard, a new synthetic substitute for homograft and heterograft skin," J. of Trauma, 13:374–383, (1973).

Anon., "Standard Test Methods for Water Vapor Transmission of Materials," ASTM, Designation: E 96/E 96M –05, Published Jun. 2005, 11 sheets, (Exhibit D–184).

Bertone, A.L., et al., "Management of Exuberant Granulation Tissue," Veterinary Clinic of North America –Equine Practice, vol. 3, pp. 551–562, (1989).

Byers, R.M., "Clinical effects of closed suction drainage on wound healing in patients with head and neck cancer," Arch. Otolaryngol., vol. 108:723–6, (Nov. 1982).

Cesany, P., "Suction in the Treatment of Torpid Ulcerations," Rozhledy v chirurgii, 48–9, MINC022894–MINC022898, cover sheet and pp. 406–409 English abstract on p. 409 (Oct. 31, 1969).

Chinn, S.D., "Closed wound suction drainage," J. Foot Surg., vol. 24: 76–81, (Jan.–Feb. 1985).

Davydov, Y., et al., "Bacteriological and Cytological Assessment of Vacuum Therapy of Purulent Wounds," Vestn. Khir., cover sheet and pp. 48–52, in Russian, English abstract provided on p. 52, (1988), (Exhibit D–172).

Davydov, Y., et al., "Vacuum Therapy in the Treatment of Purulent Lactation Mastitis," Vestn. Khir. Cover sheet and pp. 66–70, in Russian, English abstract provided on p. 70, (1986), (Exhibit D–173).

Davydov, Y.A., et al., "Vacumm Therapy in Treatment of Acute Purulent Diseases of Soft Tissues and Purulent Wounds," Vestnik Khirurgili (Surgeon's Herald), Medicine Publishers 1986, 5 sheets, (Exhibit P–528).

Everette, W.G., "Treatment of purulent wounds and fistulae with an adhesive wound irrigation device," Annals of the Royal College of Surgeons, vol. 64: 4 pages, (1981).

Fox, R., "A rapid screen for drug abuse," The Pharmaceutical Journal, 789, (1988).

Hartz, R.R., et al., "Healing of the Perineal Wound," Arch. Surg., vol. 115, 471–474, (1980), (Exhibit D–395).

Mizuno, K., "Suctioning Sponge," Arch. Opthalmol., vol. 101:294, (Feb. 1983).

Nikilov, A., "Method of treatment of postphlebitic and varicose trophic ulcers on the lower extremities by vacuum [Vacuum treatment method in postphlebitic and varicose trophic ulcers of the lower extremities]," Khirurgiia, pp. 368–374, (1981).

O'Leary, P., ed., et al., "Techniques for Surgeons," John Wiley & Sons, 2 cover sheets and pp. 417–418, article by Barbara Ann Montgomery, "142: Easy Dressing of Large, Draining Abdominal Wounds Using Moisture Vapor–Permeable Film," (1985).

Smith, S.R., "Surgical drainage," Br. J. Hosp. Med., pp. 308–315, (Jun. 1985).

Svedman, "A dressing system providing fluid and suction drainage used for continuous or intermittent irrigation," Ann. Plast. Surg., vol. 17, 9 pages, (Aug. 1986).

Svedman, "Irrigation treatment in split thickness skin grafting of intractable leg ulcers," Scand. J. Plast. Reconstr. Surg., vol. 19:211–213, (1985).

Svedman, "Irrigation treatment in split thickness skin grafting of intractable leg ulcers," Scand. J. Plast. Reconstr. Surg., vol. 19:211–213, (1985), with annotations.

Viljanto, J., "Eine neue Methods zur Behandlung offener Wundflachen," Annales Chirugine et Gynaecologiae Fenniae, 60:94–100, (1972).

Yusupov, Yu. N., et al., 5 sheets of English translation of "Active Drainage of Wounds", Vestnik khirurgii imeni I.I. Grekova 1987, 138(4), 42–46 (1987), also attached are 3 pages of English translation by BlueSky publishing entitled "Active Wound Drainage" by Usupov and Yupifanov, Vestisik Khirugii, Apr. 42–45 (1987).

Herrmann, L.G., et al., "The Conservative Treatment of Arteriosclerotic Peripheral Vascular Diseases: Passive Vascular Exercises (Pavaex Therapy)", Ann. Surg. 100(4): 750–760, (1934).

Hilsabeck, J., "The Presacral Space as a Collector of Fluid Accumulations Following Rectal Anastomosis", American Society of Colon and Rectal Surgeons, Oct., vol. 25, No. 7: 680–684, (1980).

Leaper, D.J., "The Wound Healing Process," Advances in Wound Management, T.D. Turner, et al., eds., pp. 7–16, New York: John Wiley & Sons, (1986).

Moloney, G., "Apposition and Drainage of Large Skin Flaps by Suction," The Australian and New Zealand Journal of Surgery, 26(3):173–179, (1957).

Park, G.B., et al., "The Design and Evaluation of a Burn Wound Covering", Supplied by The British Library –"The Word's Knowledge", pp. 11–15, (1978).

Turner, T.D., "Semipermeable Films as Wound Dressings", Schweiz Rundsch Med. Prax., 73(30–31): 950–952, (1984).

Taylor, V., "Meeting the Challenge of Fistulas & Draining Wounds", Nursing80, 1980, Jun., pp. 45–51.

McFarlane, R., "The use of Continuous Suction Under Skin Flaps", British Journal of Plastic Surgery, vol. 11, 1958, pp. 77–86.

* cited by examiner

WOUND TREATMENT EMPLOYING REDUCED PRESSURE

RELATED APPLICATIONS

This application is a continuation of application Ser. No. 08/467,243, entitled "Wound Treatment Employing Reduced Pressure," filed on Jun. 6, 1995, now ABN; which is a continuation of application Ser. No. 08/028,677, entitled "Wound Treatment Employing Reduced Pressure," filed Mar. 9, 1993, now U.S. Pat. No. 5,636,643, issued Jun. 10, 1997, which is a continuation-in-part of application Ser. No. 07/792,001, entitled "Method of Treating Tissue Damage and Apparatus for Same," Filed on Nov. 14, 1991, now U.S. Pat. No. 5,645,081, issued Jul. 8, 1997, each of such applications being incorporated herein by reference.

FIELD OF THE INVENTION

The present invention relates to an apparatus and method for treating a wound by applying reduced pressure to the wound.

BACKGROUND OF THE INVENTION

The treatment of open wounds that are too large to spontaneously close has long been a troublesome area of medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Poor blood circulation and infection at the wound may also hinder attachment of skin grafts or flaps upon wounded tissue. Skin grafts and flaps will not attach to tissue that is poorly vascularized, infected or necrotic. However, grafts and flaps can be used with much greater success on tissue that, although wounded, is able to form granulation tissue. Accordingly, a technique for promoting blood circulation at the wounded tissue would also promote successful attachment, or "take," of skin grafts or flaps to the wounded tissue as a consequence of increased blood circulation within the grafts or flaps.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper buns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

SUMMARY OF THE INVENTION

In accordance with the present invention a wound treatment apparatus is provided for treating a wound by applying reduced pressure (i.e. pressure that is below ambient atmospheric pressure) to the wound in a controlled manner for a selected time period. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

The wound treatment apparatus in accordance with the present invention includes a reduced pressure application appliance which is applied to a treatment site at which there is a wound and normal tissue surrounding the wound. The reduced pressure application appliance includes a fluid impermeable wound cover for covering and enclosing the wound. The appliance also includes sealing means for sealing the wound cover to the surrounding tissue of the wound in order to maintain reduced pressure in the vicinity of the wound during wound treatment. When the wound cover is sealed in position over the wound site, a generally fluid-tight or gas-tight sealed enclosure is formed over the wound site. The sealing means may be in the form of an adhesive applied to the underside of the wound cover for sealing the wound cover around the periphery of the wound. The sealing means may also include a separate sealing member such as an adhesive strip or a sealing ring in the form of a tubular pad or inflatable cuff secured to the wound cover for positioning around the periphery of the wound. In selected embodiments, the reduced pressure within the sealed enclosure under the wound cover may serve to seal the wound cover in position at the wound site. The reduced pressure appliance also includes a suction port for supplying reduced pressure within the sealed volume enclosed beneath the wound cover. The suction port may be in the form of a nipple on the wound cover. Alternatively, the suction port may be in the form of a tube attached to the wound cover or provided as a feedthrough beneath the wound cover. The appliance may also include a porous wound screen for placement in the wound or in position overlying the wound in order to prevent overgrowth of wound tissue during treatment. The wound screen is sufficiently porous to permit gas flow to the wound. The porous wound screen may be in the form of a sponge or open-cell foam material for placement in the wound. The porous screen may also include a rigid or semi-rigid screen for overlying the wound.

A vacuum system is connected with the reduced pressure appliance in order to provide suction or reduced pressure to the appliance. For this purpose, the vacuum system includes a suction pump or suction device for connection with the suction port of the appliance for producing the reduced pressure over the wound site. The vacuum system may include a section of hose or tube, such as a vacuum hose, that interconnects the suction device with the suction port of the appliance to provide the reduced pressure at the wound site. A collection device in the form of a fluid trap may be provided intermediate the vacuum hose of the suction device and the suction port of the appliance to trap any exudate which may be aspirated from the wound by the negative pressure appliance. A stop mechanism may also be provided for the vacuum system to halt production of the reduced pressure at the wound site in the event that an excessive quantity of exudate has been collected. The apparatus may also include a control device for controlling the pump and for providing intermittent or cyclic production of reduced pressure.

In a particular embodiment of the invention, the wound cover for the reduced pressure appliance may be in the form of a gas impermeable covering sheet of flexible polymer material, such as polyethylene, having an adhesive backing that provides the seal for securing the sheet over the wound site to provide an gas-tight or fluid-tight sealed enclosure over the wound site. The vacuum system of the wound treatment apparatus may include a suction pump having a vacuum hose that is connected with a suction tube serving as a suction port for the appliance. The suction tube for the appliance runs beneath the cover sheet that is sealed in position over the wound site and into the fluid-tight enclosure provided under the cover sheet. An adhesive backing on the cover sheet is used to provide a fluid-tight seal around the feedthrough for the suction tube at the wound site. Within the enclosure, the suction tube is connected with a piece of open-cell foam for placement in the wound. The open-cell foam functions to more uniformly apply reduced pressure or suction over the wound site while holding the cover sheet substantially out of the wound during the application of reduced pressure at the enclosed wound site.

In operation, a method of treating tissue damage is provided which comprises applying a negative or reduced pressure to a wound over an area sufficient to promote the migration of epithelial and subcutaneous tissue toward the wound and for a time period sufficient to facilitate closure of the wound. The method is useful for treating pressure sores.

A method of treating a burn wound is also provided which comprises applying a negative or reduced pressure to the burn over an area and for a time sufficient to inhibit progression in the depth of the burn. The method is useful on a partial thickness burn soon after its infliction.

A method of treating tissue damage is also provided which comprises applying a negative or reduced pressure to a wound for a time sufficient to reduce bacterial density in the wound. One use of this method is its application to a wound for a selected time period such as at least three days to reduce the bacterial density of an infected wound to the point at which surgical closure can be attempted.

Another aspect of the invention is a method of enhancing the attachment of adjacent tissue to a wound which comprises applying negative or reduced pressure to a joined complex of the adjacent living tissue and the wound at a sufficient magnitude of reduced pressure and for a sufficient time duration to promote the migration of epithelial and subcutaneous tissue toward the complex. This method enhances attachment of adjacent tissue to tissues of the wound edges. Another use of this method is to enhance attachment of an open skin graft to the wound tissue.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENTS

Figure 10:
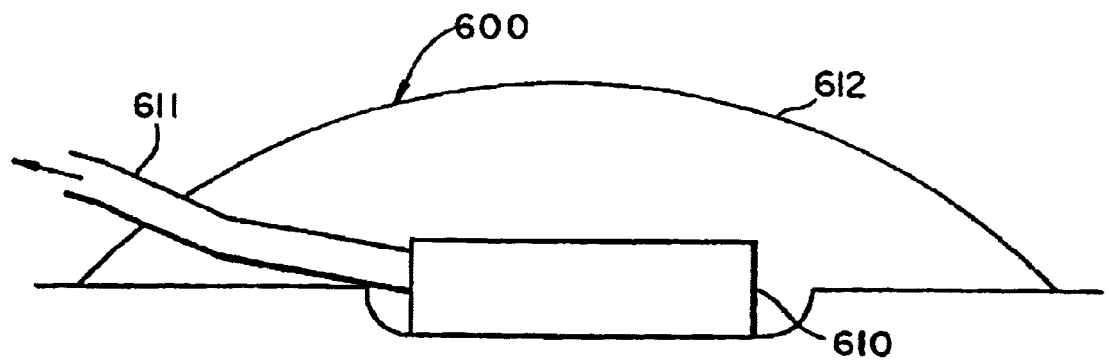
FIG. 10 is a schematic cross-sectional view of a reduced or negative pressure appliance comprising an open-cell polymer foam screen, a flexible hose for connecting the foam screen with a vacuum system, and an adhesive-backed flexible polymer sheet overlying the foam-hose assembly to provide a seal over a wound.

In accordance with the present invention, a wound treatment apparatus is provided for treating a wound by application of reduced pressure (i.e., below atmospheric pressure) so that suction may be applied to a wound site in a controlled manner for a selected time period. As schematically shown in FIG. 10, a wound treatment apparatus includes a reduced pressure appliance, generally designated 600, which is applied to a wound site to treat the wound through the application of reduced pressure. The appliance 600 is sealed in position over the wound site to create a generally fluid-tight or gas-tight enclosure over the wound site.

The appliance 600 includes a substantially flat section of open cell polyester foams section 610 (Fischer Scientific, Pittsburgh, Pa. 15219) sufficiently large to cover the wound and thus prevent wound overgrowth, a flexible hollow tube 611 (Fischer Scientific) inserted into the open cell foam section 610 and joined thereto with an adhesive and extending to attach at its opposite end with a Gast Vacuum pump (Fischer Scientific), and an Ioban adhesive sheet 612 (Minnesota Mining and Manufacturing, St. Paul, Minn. 55144) overlying the foam section 610 and tubing 611 and adhered to the skin surrounding the wound, thus forming a seal that allows creation of a vacuum when the suction pump operates. Such an appliance 600 would most preferably be packaged in a sterile condition to ameliorate the need for sterilization of the apparatus prior to use. The adhesive sheet 612 may be packaged separately from the foam-tube assembly 610 and 611. A particular advantage of this configuration is its use with pressure sores because the device can be placed in the depths of the wound and the patient can lie upon the device without either affecting the utility of the device or further damaging the wound. This becomes critical if the patient cannot be moved from this posture for medical or other reasons.

Figure 11:
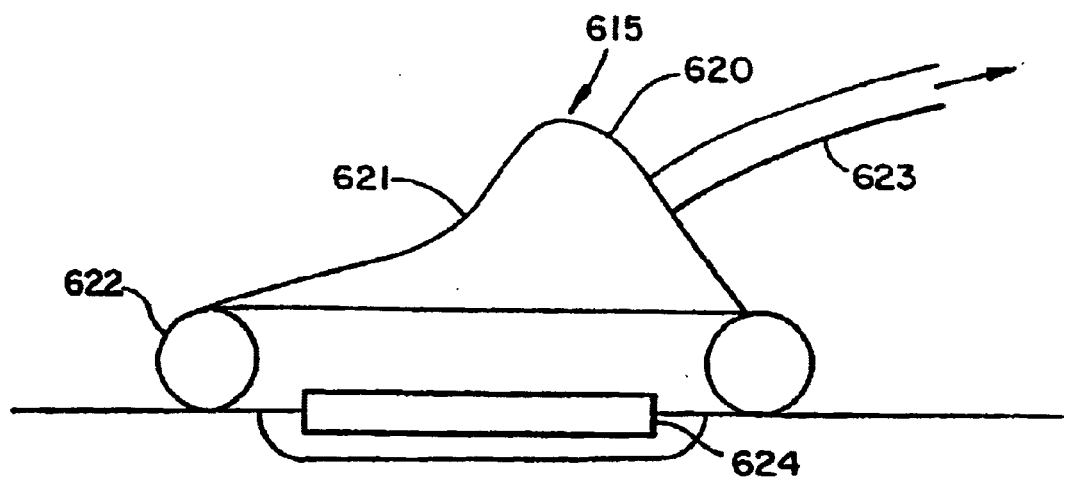
FIG. 11 is a schematic cross-sectional view of a reduced or negative pressure appliance comprising a rigid porous screen for a wound, a rigid or semi-rigid cup for covering the wound having an inflatable cuff attached about the base of the cup, and a flexible hose extending from the cup for connection with a vacuum system.

As shown in FIG. 11, a reduced pressure appliance, generally designated 615, in accordance with another embodiment of the present invention, is schematically depicted. The reduced pressure appliance 615 includes an adult CPR mask 620 (Doug Brown and Associates, Huntington Beach, Calif. 92648) comprising a rigid or semi-rigid fluid impermeable cup 621 having an inflatable cuff 622 mounted around the periphery of the base of the cup 622 for contact with the skin, an open cell polyester screen 624 overlying the wound, and a flexible ¼ inch diameter hose 623 (Fischer Scientific) connected by a Nalgene tubing connector extending through a sealed hole in the cup for connection with a vacuum pump (Fischer Scientific). The hose 623 is connected with the pump 40 of a vacuum system 30 of the type shown in FIG. 1 to provide reduced pressure within the cup 621. The vacuum created within the cup 621 by the vacuum system may be sufficient to seal the cup in position over the wound site. Alternatively, fluid impermeable adhesive covering or strips may also be used to seal the appliance 615 in proper position.

Figure 1:
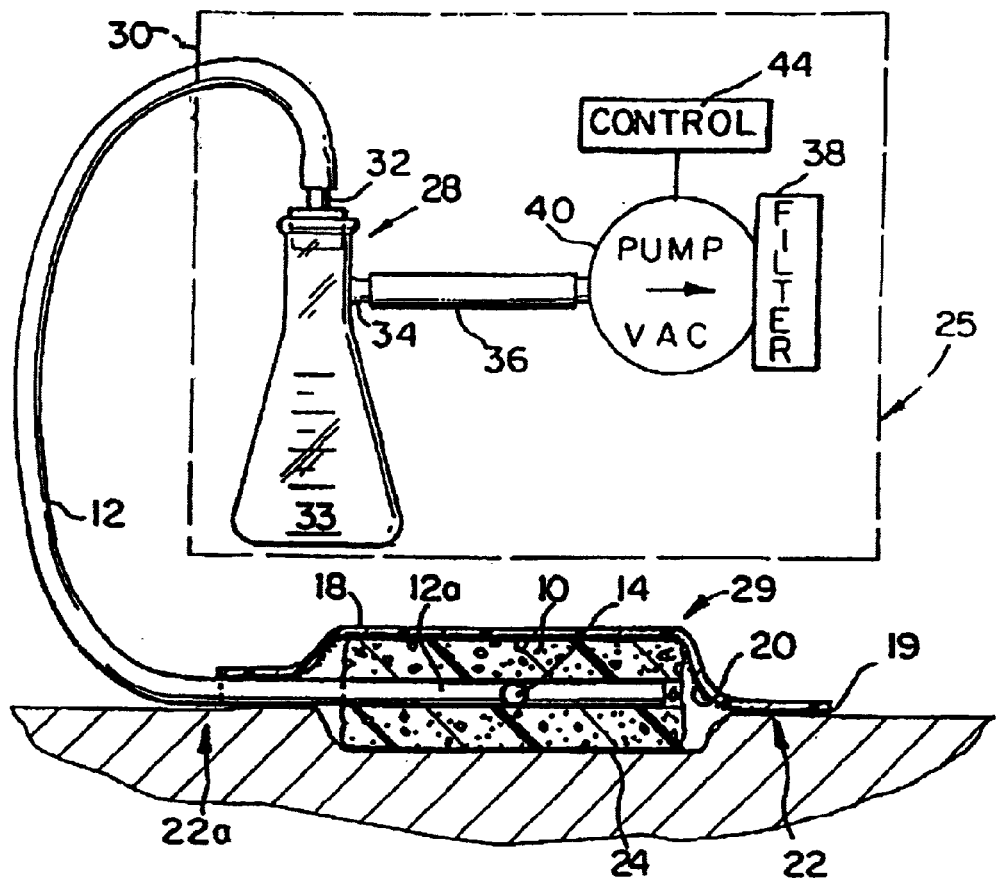
FIG. 1 is a schematic elevational view of a wound treatment apparatus in accordance with the present invention in which a reduced pressure appliance, shown in partial section, includes a flexible, fluid impermeable wound cover sealed over the wound and a foam wound screen positioned in the wound, and in which a vacuum system provides reduced pressure within the wound cover of the appliance.

Referring to FIG. 1, a wound treatment apparatus, generally designated 25, is depicted having a reduced pressure appliance 29 for enclosing a wound site to provide a fluid-tight or gas-tight enclosure over the wound site to effect treatment of a wound 24 with reduced or negative pressure. The wound treatment apparatus 25 includes a reduced pressure appliance, generally designated 29, which is applied to and sealed over a wound site in order to enclose the wound site for treatment with suction or reduced pressure within a sealed generally fluid-tight or gas-tight enclosure. For the purpose of creating suction within the appliance 29, the appliance 29 is connected with a vacuum system, generally designed 30, to provide a source of suction or reduced pressure for the sealed appliance 29 at the wound site. The appliance 29 includes a fluid-impermeable wound cover 18 in the form of a flexible, adhesive, fluid impermeable polymer sheet for covering and enclosing the wound 24 and the surrounding normal skin 22 at the wound site. The wound cover 18 includes an adhesive backing 20 which functions to seal the wound cover to the normal skin 22 around the periphery of wound 24 to provide a generally gas-tight or fluid-tight enclosure over the wound 24. The adhesive cover sheet 18 must have sufficient adhesion to form a fluid-tight or gas-tight seal 19 around the periphery of the wound and to hold the sheet 18 in sealed contact with the skin during the application of suction or reduced or negative pressure.

The appliance 29 also includes a porous wound screen 10 which is placed within the wound 24. The wound screen 10 is placed over substantially the expanse of the wound to prevent its overgrowth. The size and configuration of the wound screen 10 can be adjusted to fit the individual wound. It can be formed from a variety of porous materials. The material should be sufficiently porous to allow oxygen to reach the wound. The wound screen 610 may be in the form of an open-cell polymer foam, such as a polyurethane foam, which is sufficiently porous to allow gas flow to and/or from the wound 24. Foams may be used that vary in thickness and rigidity, although it may be desirable to use a spongy material for the patient's comfort if the patient must lie upon the appliance during treatment. The foam may also be perforated to enhance gas flow and to reduce the weight of the appliance. As shown in FIG. 1, the screen 10 is cut to an appropriate shape and size to fit within the wound 24. Alternatively, the screen may be sufficiently large to overlap the surrounding skin 22.

The appliance 29 also includes a suction port in the form of a hollow suction tube 12 that connects with the vacuum system 30 to provide suction within the sealed enclosure. The suction tubing 12 serves as a suction port for appliance 29. An end segment 12a of the tubing 12 is embedded within the foam screen 10 for providing suction or reduced pressure within the enclosure provided under the wound cover 18. Embedding the open end of segment 12a of tubing 12 within the interior of the foam screen 10 permits the foam screen 10 to function as a shield to help prevent the wound cover 18 from being inadvertently sucked into sealing engagement with the open end of the tube thereby plugging the tube 12 and restricting gas flow. The tube segment 12a embedded within the foam screen 10 preferably has at least one side port 14 for positioning within the interior of the foam screen 10 to promote substantially uniform application of reduced pressure throughout the enclosure. Positioning the side port 14 of the tube segment 12a within the interior of the foam screen 10 permits the foam screen 10 to function as a shield for the side port to thereby prevent the wound cover 18 from being sucked into the side port 14 and thereby restricting gas flow. The open cells of the foam screen 10 facilitate gas flow throughout the enclosure. In addition, the foam screen 10 functions to prevent wound overgrowth and to hold the wound cover 18 generally out of contact with the wound 24 during the application of suction within the enclosure.

Tubing 12 and tube segment 12a are sufficiently flexible to permit movement of the tubing but are sufficiently rigid to resist constriction when reduced pressure is supplied to the appliance 29 or when the location of the wound is such that the patient must sit or lie upon the tubing 12 or upon the reduced pressure appliance 29. The screen-tube assembly comprising the foam screen 10 and the tube 12 may be fabricated by snaking the end of the tube segment 12a through an internal passageway in the foam screen 10 such as by pulling the end of the tube segment 12a through the passageway using forceps. Alternatively, fabrication of the screen-tube assembly may be accomplished by suspending the end of the tube segment 12a into a suitable mold or form and then blowing foam into the mold or form to embed the tube end segment 12a within the blow-molded foam screen. The screen-tube assembly 12 and 10 is preferably prepared prior to use under sterile conditions and then stored in an aseptic package.

In order to use the reduced pressure appliance 29 at the site of the wound 24, the flexible, gas-impermeable, adhesive wound cover sheet 18 is secured in position at the wound site overlying the foam screen 10 disposed within the wound 24. The wound cover sheet 18 is secured and sealed to the surrounding normal skin 22 by an adhesive layer 20 on the under surface of the wound cover 18 to form a gas-tight seal 19 around the periphery of the wound 24. The wound cover 18 also provides a gas-tight seal around the tubing 12 at the feedthrough location 22a where the tubing 12 emerges from beneath the wound cover 18. The wound cover 18 is preferably formed of a fluid impermeable or gas impermeable flexible adhesive sheet such as Ioban, a product of the 3M corporation of Minneapolis, Minn.

The vacuum system 30 includes a suction pump 40 that produces a source of reduced pressure or suction which is supplied to the reduced pressure appliance 29 by suction tubing 12. As shown in FIG. 1, a fluid trap, generally designated 28, is interconnected between the suction pump 40 and the appliance 29 to remove and collect any exudate which may be aspirated from the wound 24 by the reduced pressure appliance. The appliance 29 functions to actively draw fluid or exudate from the wound 24. Collection of exudate in a fluid trap 28 intermediate the pump 40 and the appliance 29 is desirable to prevent clogging of the pump 40. A suitable fluid trap 28 may be assembled from an Erlenmeyer or side-arm flask 31 having a top opening and a side-arm opening. The fluid trap 28 includes a first port 32 at the top opening of the flask for sealed connection to suction tubing 12. The first port 32 enables suction to be applied to the reduced pressure appliance 29 through the tubing 12 and also enables exudate from the wound covered by reduced pressure appliance 29 to be drained into the flask 31. The flask 31 provides a collecting vessel 33 for the fluid trap for containing and temporarily storing the collected exudate. A suction port 34 is provided at the side-arm opening of the flask to enable the application of suction from vacuum pump 40. The suction port 34 of the fluid trap 28 is connected to the vacuum pump 40 by vacuum line 36. The fluid trap 28 is sealed generally gas-tight to enable the suction pump 40 to supply suction to the appliance 29 through the fluid trap 28. A filter 38 such as micropore filter is preferably attached to the exhaust of the pump 40 to prevent potentially pathogenic microbes or aerosols from being vented to atmosphere by the vacuum pump 40.

Predetermined amounts of suction or reduced pressure are produced by the vacuum pump 40. The vacuum pump 40 is preferably controlled by a control device 44 such as a switch or a timer which may be set to provide cyclic on/off operation of the vacuum pump 40 according to user-selected intervals. Alternatively, the vacuum pump 40 may be operated continuously without the use of a cyclical timer.

The vacuum system 30 preferably includes a shut-off mechanism for halting or inhibiting the supply of the reduced pressure to the appliance 29 in the event that the exudate aspirated from the wound 24 exceeds a predetermined quantity. Interrupting the application of suction to the appliance 29 is desirable to prevent exsanguination in the unlikely event a blood vessel ruptures under the wound cover 18 during treatment. If, for example, a blood vessel ruptures in the vicinity of the wound 24, a shut-off mechanism would be useful to prevent the vacuum system 30 from aspirating any significant quantity of blood from the patient. As a safety feature, various mechanical or electrical detection mechanisms may be employed to detect the level of exudate in the fluid trap 28.

Figure 7:
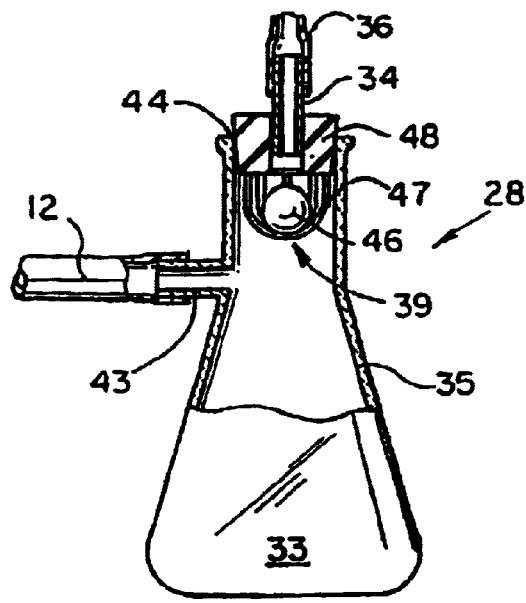
FIG. 7 is a schematic elevational view in partial section of an alternative fluid collection device having a float valve for use in the vacuum system of FIG. 1.

As shown in FIG. 7, a fluid trap 28 employing a collection bottle or flask 35 is provided for connection intermediate the pump 40 and the appliance 29 for collecting exudate from the wound site. The flask 35 has a side-arm port 43 connected to suction tube 12 leading to the reduced pressure appliance 29 and a suction port 34 located at the top 44 of the flask 35 connected to the vacuum hose 36 leading to the vacuum pump 40. For the purpose of detecting liquid level within the flask 35, a float valve assembly, generally designated 39, is provided. The float-valve assembly 39 functions to close and seal off the suction port 34 of the fluid trap 28 when the quantity of exudate in the collecting vessel 33 exceeds a predetermined quantity. The float valve assembly 39 is provided in the form of a ball 46 which is held and suspended within a cage 47 positioned below a valve seat 48 disposed within the opening at the top 44 of the flask 35. The ball 46 has a specific gravity below that of the exudate so that the ball 46 will float upon the exudate and will be lifted against the valve seat 48 as the vessel 33 fills with exudate. When the ball 46 is firmly seated against the valve seat 48, the float valve 39 blocks suction port 34 and thereby shuts off the source of suction from vacuum line 36. The suction within the appliance 29 at the wound site arrests thus halting the aspiration of exudate from the wound.

Figure 8:
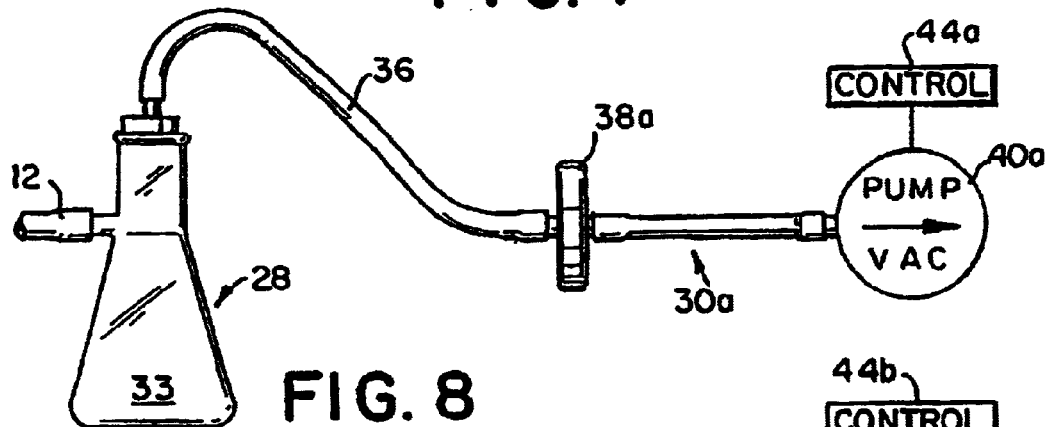
FIG. 8 is a schematic view of an alternative vacuum system.

Other types of mechanisms may be employed to detect the liquid level within the fluid trap 28 in order to arrest operation of the vacuum source. An alternative vacuum system 30a is shown in FIG. 8 in which a filter 38a is employed in vacuum line 36 for filtering the fluid or gas flow through the vacuum line 36 and for detecting the level of liquid in fluid trap 28. Exudate from the wound is collected in vessel 33. When the vessel 33 becomes full, aspiration of further exudate from the wound causes the vacuum line 36 to begin to collect exudate which eventually reaches the in-line filter 38a positioned in the vacuum line 36 intermediate the fluid trap 28 and the pump 40a having operational control 44a. The filter 38a contains a filter element that is selected to clog when exposed to sufficient amounts of moisture to thereby halt the supply of suction through the fluid trap 28 to the appliance 29. The filter 38a is preferably an in-line, disc-shaped submicron filter having a nitrocellulose or PTFE filtration element for filtering particles larger than about 0.1 µm from the vacuum line 36. In addition to preventing excess fluid aspiration, the filter 38a in the vacuum line 36 prevents contamination of the vacuum pump 40 by filtering potentially pathogenic microbes and aerosols.

Figure 9:
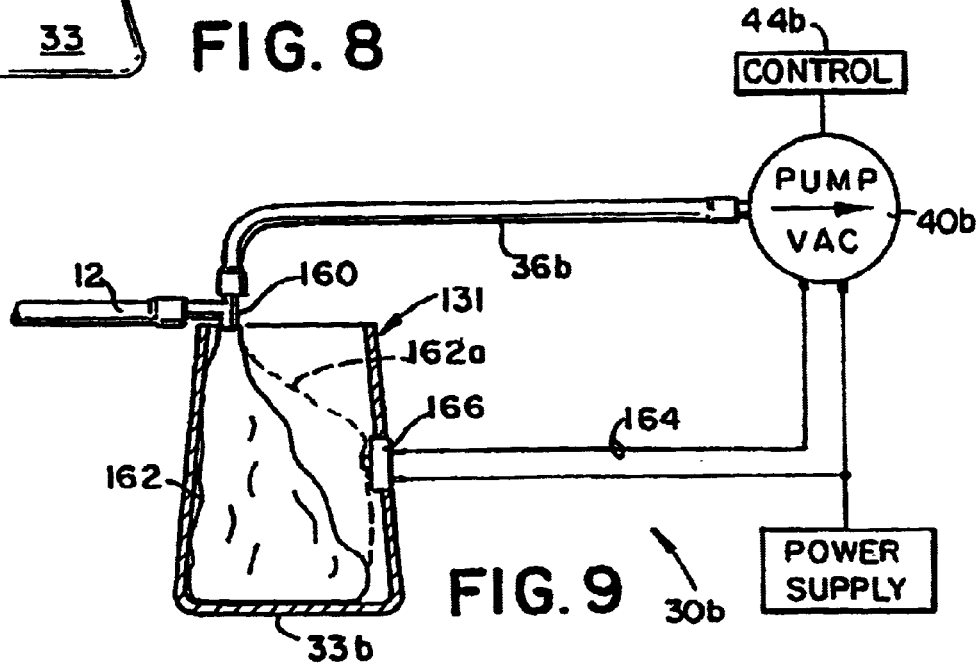
FIG. 9 is a schematic view of an alternative vacuum system incorporating a fluid collection device having an actuator for de-activating the vacuum system upon collection of a predetermined quantity of fluid.

Other types of detection devices may also be employed to detect a predetermined level of liquid collected in collection vessel 33. For example, collection of exudate in excess of a predetermined quantity may enable actuation of an electronic switch which turns off the vacuum pump or otherwise halts the supply of suction to the reduced pressure appliance 29. Referring to FIG. 9, the suction tubing 12 from the reduced pressure appliance 29 is connected to a three-port coupling device 160 that interconnects suction tube 12, vacuum line 36b and fluid collecting apparatus 131. The coupling device 160 permits transmission of suction from the vacuum line 36b of the pump 40b to the suction tubing 12. The coupling device 160 also permits aspirated exudate from tubing 12 to be collected in an expandable container, such as an intravenous fluid bag 162, housed beneath the coupling device 160 in a rigid housing vessel 33b. As exudate is collected, the bag 162 expands to conform to the shape of the interior surface of the surrounding rigid vessel 33b. An actuator 166, such as a spring-loaded actuator switch, is loaded within the side wall of the rigid vessel 33b and functions to shut off the pump 40b upon actuation of the switch 166. When the bag 162 expands sufficiently to contact and actuate switch 166 as shown in dashed lines at 162a in FIG. 9, the switch 166 is opened and the supply of power to the pump 40b along power line 164 is interrupted and the supply of suction to the appliance 29 is stopped. The actuator switch 166 may also cooperate with control 44b for the pump 40b to stop operation of the pump 40b. Other types of devices may also be employed to detect fluid levels in fluid trap 28. For example, weight detectors may be employed to detect a predetermined weight limit as the fluid trap fills with exudate or other liquid. Alternatively, optical sensors or detectors may also be employed.

Figure 2:
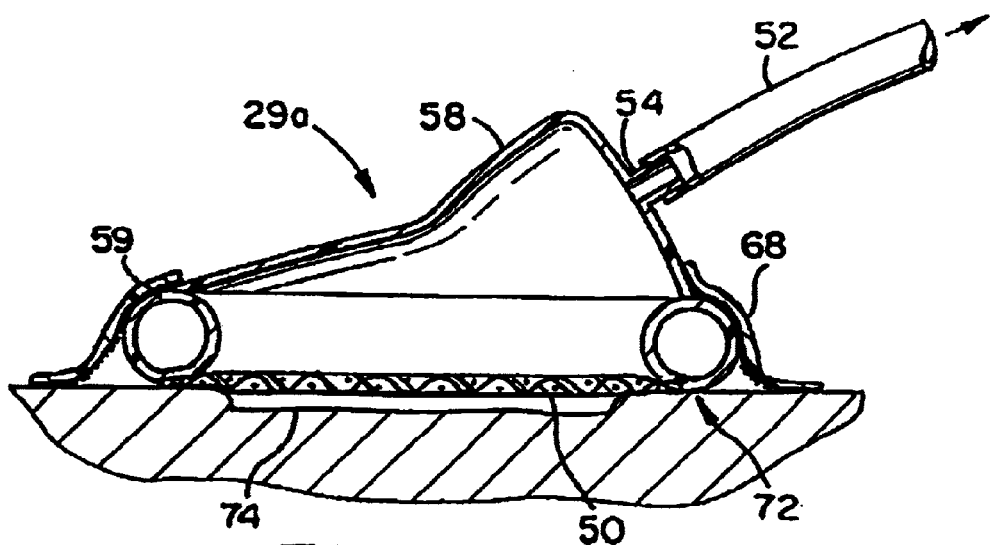
FIG. 2 is a schematic sectional elevational view of a reduced pressure appliance in accordance with another embodiment of the present invention having a rigid, fluid impermeable wound cover sealed over a wound and a rigid or semi-rigid screen overlying the wound.

For the purpose of protecting the site of a wound from impact or abrasion during treatment, a reduced pressure appliance employing a rigid or semi-rigid wound cover may be utilized over the site of the wound. As shown in FIG. 2, a reduced pressure appliance 29a includes a CPR mask 58 that provides a rigid wound cover for enclosing an appropriately-sized wound 74. The mask 59 is impermeable to fluids or gases so that a fluid-tight or gas-tight enclosure is effected over the wound site. The mask 59 is sufficiently rigid to support itself away from the wound during the application of suction or reduced pressure so that the mask 59 does not collapse into the wound 74. The CPR mask 58 is of the type having an inflatable air cuff 59 around the base of the mask. The cuff 59 may be inflated via an external valve for sealing the mask 59 against the normal skin 72 around the periphery of the wound 74. The air cuff 59 also prevents the base of the mask from digging into the skin 72 during application of reduced pressure. An optional screen 50 for preventing overgrowth of the wound 74 may be positioned to overlie the wound 74. The screen 50 may be formed of a rigid or semi-rigid perforated polymer surgical mesh such as Prolene mesh. Alternatively, a section of honeycombed polyethylene sheet may be cut to a suitable size and shape to overlie the wound 74. The screen 50 is held against the surrounding normal skin 72 in position overlying wound 74 by the cuff 59 which overlaps at least a portion of the periphery of the screen 50. The CPR mask 58 also includes a suction port in the form of a hose connector 54 to which one end of a suction tube 52 is attached. The other end of tube 52 is connected with a vacuum system 30 of the type previously described to provide a source of suction or reduced pressure for the appliance 29a. Suction produced within the appliance 29a may be sufficient to seal the cuff 59 to the skin and to thereby seal the appliance 29a in position over the wound site. However, in order to ensure a gas-tight seal between the reduced pressure appliance 29a and the surrounding skin 72, the mask 58 may also be secured to the treatment site with a fluid impermeable adhesive seal 68. The adhesive seal 68 may be formed of a flexible adhesive material such as an adhesive tape or an adhesive sheet that has been cut to surround and at least partially overlie the cuff 59. As shown in FIG. 2, the adhesive seal is secured to the base portion of the rigid mask 58 and to the normal skin 72 around the periphery of the air cuff 59 to seal the mask in position over the wound site.

Figure 3:
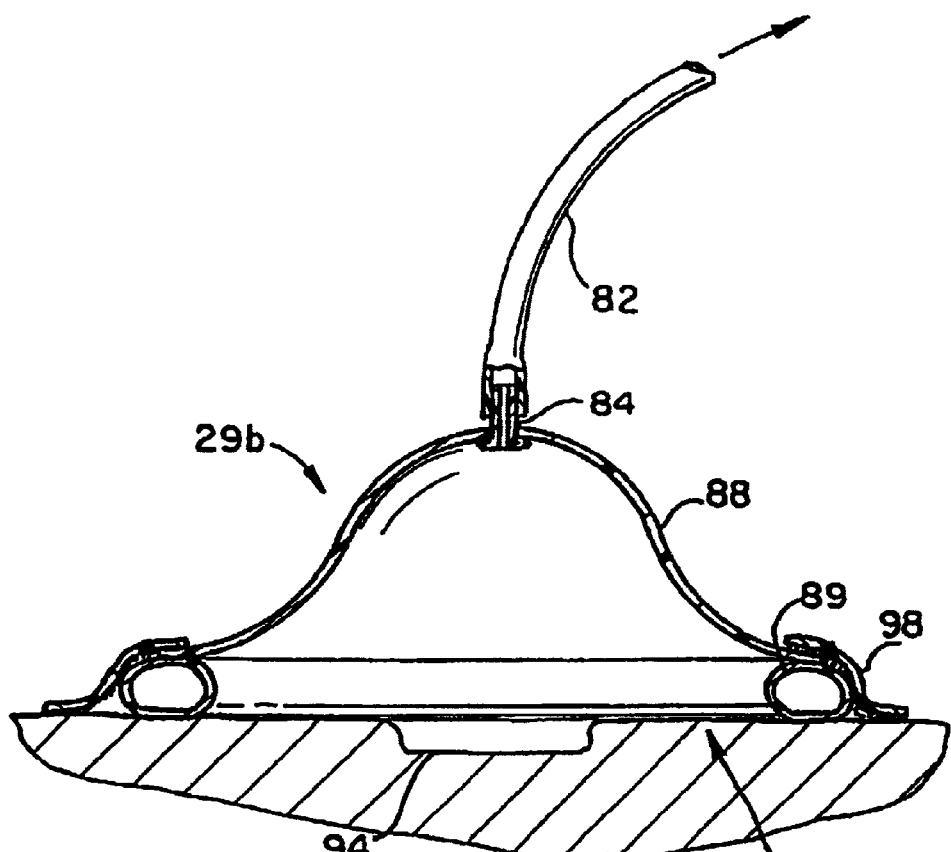
FIG. 3 is a schematic sectional elevational view of a reduced pressure appliance in accordance with another embodiment of the present invention having a rigid, fluid impermeable wound cover sealed over a wound.

As shown in FIG. 3, a reduced pressure appliance 29b is depicted having a rigid, fluid impermeable, cup-shaped wound cover 88 overlying a wound site. The appliance 29b is used to treat a wound 114 without any screen either in the wound or overlying the wound. The cover cup 88 can be formed of a polymer such as polystyrene, HDPE, or other suitably rigid material. The cup 88 must be sufficiently rigid to support itself out of contact with the wound 114 during the application of suction or negative pressure so that the cup 88 does not collapse into the wound. Reduced pressure is supplied to the interior of the cup 88 through the suction tubing 82 connected to suction port 84 in the form of a nipple sealed in position on the cup 88. The tubing 82 is also connected with a suitable vacuum system 30 of the type previously described to provide a source of suction or negative pressure within the appliance 29b. The base of the cup 88 supports an inflatable air cuff 89 to seal the cup 88 to the skin and to prevent the cup 88 from digging into the skin 92 and causing discomfort when reduced pressure is applied. The cuff 89 is positioned upon the normal skin 92 surrounding the wound 94. While the suction created within the cup 88 may be sufficient to hold the appliance in position by causing the air cuff to seal to the skin, more effective attachment of the appliance to the surrounding skin 92 may be obtained by the use of a strip of fluid impermeable, adhesive material secured to the skin 102 and to the base of the cup 88 over the air cuff 89 around the periphery of the base of the cup 88. The layer of adhesive material 98 helps to ensure that a fluid-tight or gas-tight seal is maintained between the cup 88 and the surrounding skin 92 so that a fluid-tight enclosure is formed over the wound site.

Figure 4:
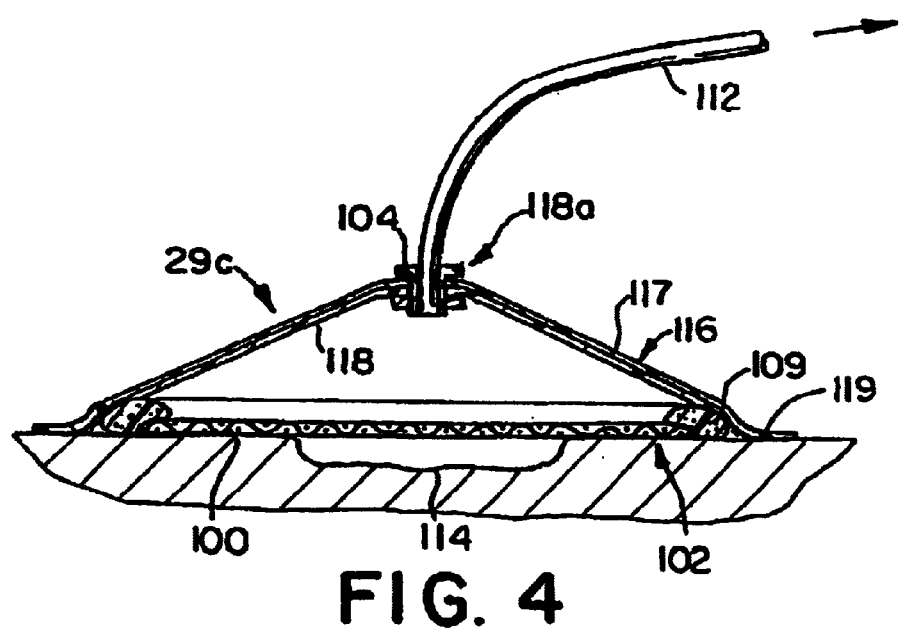
FIG. 4 is a schematic sectional elevational view of a reduced pressure appliance in accordance with another embodiment of the present invention having a semi-rigid, fluid impermeable cover enclosing a wound and a rigid or semi-rigid screen overlying the wound, with an overlying flexible fluid impermeable cover sheet sealing the enclosure over the wound.

Referring to FIG. 4, a reduced pressure appliance 29c is depicted for enclosing a wound site for the treatment of wound 114 with suction or reduced pressure. The reduced pressure appliance 29c includes a fluid-impermeable wound covering, generally designated 116, having an outer flexible, adhesive polymer sheet 117 applied over an inner, generally circular, semi-rigid shield 118, such as a polystyrene shield, for covering and enclosing the wound site. The base of the shield 118 is positioned over a circular pad 109 which may be formed from flexible tubing to prevent the base of the cup from digging into the skin 102 and causing discomfort when suction is applied to the appliance 29c. The pad 109 may also facilitate sealing of the cover shield 118 in position over the wound site to form a fluid-tight or gas-tight enclosure over the wound site. The pad 109 may be positioned directly onto the normal skin 102 surrounding the wound 114 or, as shown in FIG. 4, the pad 109 may overlie an outer peripheral portion of a rigid screen 100 in order to hold the screen 100 in a position overlying the wound to prevent wound overgrowth. A suction port 104 is provided at the top of the shield 118 to permit gas-tight connection to suction tube 112. The suction port 104 may be in the form of a removable connector that is screwed into position at the top of the shield 118. Suction tube 112 functions to connect the appliance 29c to a suitable vacuum system 30 of the type previously described. For the purpose of enhancing the sealing of the appliance 29c in position over the wound site, an over-sized, generally circular, adhesive, fluid impermeable polymer sheet 117 is adhered and secured to the top surface of the shield 118. The oversized adhesive sheet 117 extends beyond the outer periphery of the shield 118 so that the adhesive sheet 117 provides a sealing ring 119 of material around the periphery of the shield. The sealing ring 119 is sealed and adhered to the normal skin 102 around the outer periphery of pad 109. When sealed in position overlying wound 114, the appliance 29c provides a generally fluid-tight or gas-tight enclosure over the wound site.

Figure 5:
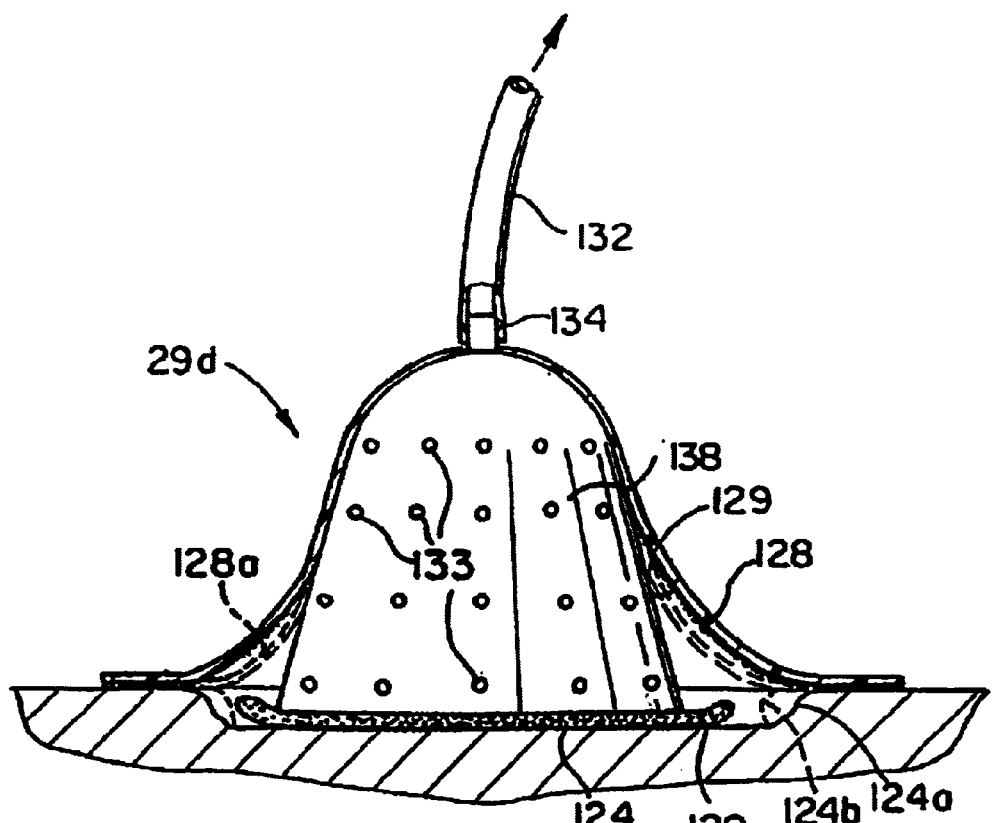
FIG. 5 is a schematic elevational view of a reduced pressure appliance, shown in partial section, in accordance with another embodiment of the present invention having a flexible, fluid impermeable wound cover over an inner rigid porous support cup.

Referring to FIG. 5, a reduced pressure appliance 29d is depicted for enclosing and treating a wound 124 with suction or reduced pressure. A rigid or semirigid porous cup 138 is placed rim side down upon a porous screen or pad 120 located within a wound 124. The cup 138 has perforations 133 for equalizing pressure inside and outside of the cup 138. A flexible, fluid impermeable adhesive polymer cover sheet 128 is draped over the cup 138 to enclose the wound 124. The adhesive cover sheet 128 is adhered and sealed to the top portion of the cup 138 and to the surrounding normal skin 122 by adhesive layer 129 on the underside of the cover sheet 128 to provide a fluid-tight enclosure beneath the sheet 128. The cup 138 provides a generally central support beneath the cover sheet 128 to hold the cover sheet 128 out of contact with the wound 124 during application of suction. The cup 138 has a central suction port 134 sealed in position at the top of the cup 128 to permit connection by suction tube 132 to a vacuum system 30 of the type previously described. When reduced pressure is supplied to the appliance 29d, the cover sheet 128 is deformed downward and inward to position 128a as shown in phantom in FIG. 5. Tension developed within the deformed sheet 128a by virtue of the suction is exerted upon the surrounding skin by the sheet at position 128a. The outer periphery 124a of the wound 124 is pulled inward by virtue of such tension to the position shown in phantom at 124b to promote closure of the wound. The tension within the sheet at position 128a also exerts a downward force upon the cup 138 which more firmly presses the cup 138 onto the wound 124. Such downward force on the cup 138 may be desired in such applications as flap or graft attachment to promote contact between the flap or graft and the underlying tissue. The pad 124 under the cup 138 helps to alleviate discomfort caused by the downward force on the cup 138.

Figure 6:
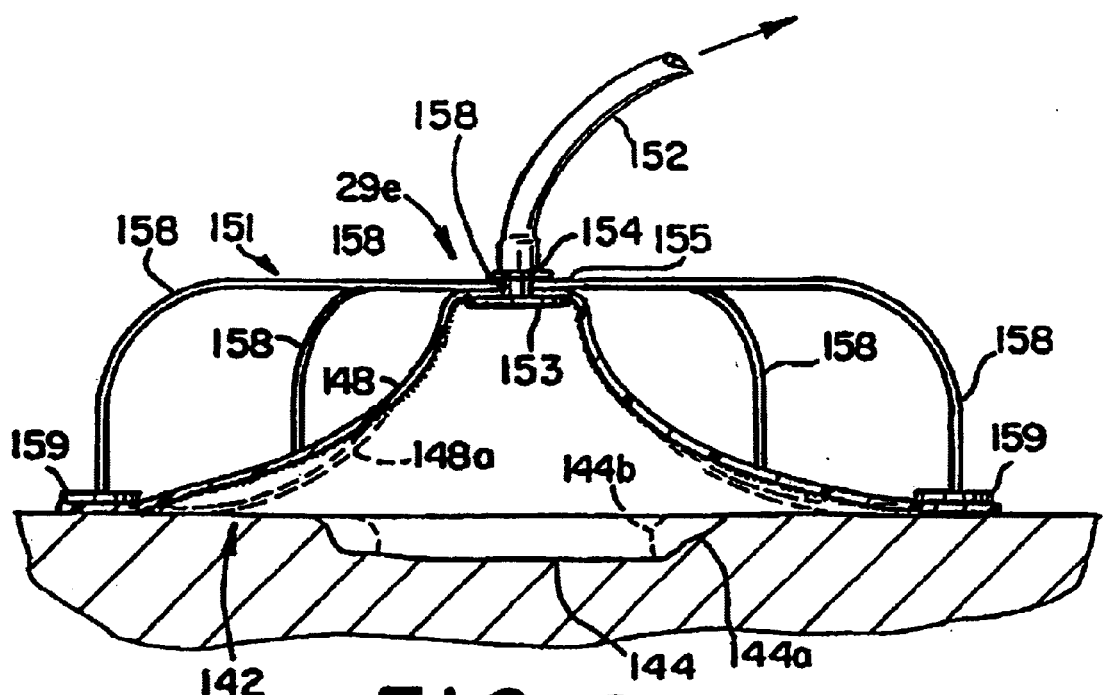
FIG. 6 is a schematic elevational view of a reduced pressure appliance, shown in partial section, having a rigid outer frame with support legs for supporting a flexible, fluid impermeable sealing cover over a wound.

For applications where a downward pressure of the appliance into a wound is not desired, a reduced pressure appliance 29e, as shown in FIG. 6, may be utilized having a support structure, generally designated 151, which is positioned external to a flexible sealing sheet 148 for covering a wound 144. The flexible cover sheet 148 is in the form of a flexible, fluid impermeable, adhesive polymer sheet. The reduced pressure appliance 29e shown in FIG. 6 includes an external support frame 151 in the form of a series of spider-like legs 158 radiating outwardly from a central support hub 155. The legs 158 hold the central hub 159 directly over the wound 144. A connector 153 is removably mounted to the hub 155 to permit a suction tube 152 to be connected with the flexible cover sheet 148. The connector 153 may screw together and apart to permit the connector to be removably mounted relative to the hub 155. The flexible adhesive sheet 148 is adhered to the connector 153 at hub 155 and to the surrounding normal skin 142 so that the sheet is suspended over the wound 144 from the hub 155 in tentlike fashion. The flexible sheet is adhesively sealed to the connector 153 at the hub 155 and is also adhesively sealed to the skin 142 around the periphery of the wound 144 to form a fluid-tight or gas-tight enclosure over the wound site. The legs 158 of the frame 153 extend radially outward from the hub 153 and stand upon feet members 159 which may rest upon the outer periphery of the sheet 148 to help hold the cover sheet 148 in a position from being sucked together during the application of suction. Alternatively, the feet members 159 may extend beyond the cover sheet 148 and may rest upon the surrounding tissue beyond the periphery of the cover sheet 148. The connector 153 supported on the hub 155 provides a suction port 154 through which suction is supplied to the appliance 29e via suction tube 152. Tube 152 is connected to a vacuum system 30 of the type previously described for supplying reduced pressure within the cover sheet 148. When suction or reduced pressure is introduced via port 154, the sheet 148 deforms inwardly and downwardly to the position shown in phantom at 148a thus developing tension which is exerted upon the surrounding skin 142. The deformed sheet in position at 148a pulls the edges of the wound 144 inwardly to the position indicated in phantom at 144b hence promoting closure of the wound 144.

Negative pressure appliances are useful for treating a variety of wounds. Treatment of a wound can be carried out by securing a negative pressure appliance to the treatment site as previously shown and described, and then maintaining a substantially continuous or cyclical reduced pressure within the appliance until the wound has reached a desired improved condition. A selected state of improved condition may include formation of granulation tissue sufficient for the attachment of a flap or graft, reduction of microbial infection in the wound, arrest or reversal of burn penetration, closure of the wound, integration of a flap or graft with the underlying wounded tissue, complete healing of the wound, or other stages of improvement or healing appropriate to a given type of wound or wound complex. It may be preferable to change the appliance periodically, such as at 48 hour intervals, during treatment, particularly when using appliances incorporating a screen on or in the wound. The method is preferably practiced using a negative or reduced pressure ranging from 0.01 to 0.99 atmospheres, and more preferably praticed using a negative or reduced pressure ranging between 0.5 to 0.8 atmospheres. The time period for use of the method on a wound may preferably be at least 12 hours, but can be, for example, extended for one or more days. There is no upper limit beyond which use of the method is no longer beneficial; the method increases the rate of closure up to the time the wound actually closes. Satisfactory treatment of various types of wounds has been obtained via the use of reduced pressures equivalent to about 2 to 7 in. Hg below atmospheric pressure.

Supplying reduced pressure to the appliance in an intermittent or cyclic manner has also been demonstrated to be useful for treating wounds. Intermittent or cyclic supply of reduced pressure to an appliance may be achieved by manual or automatic control of the vacuum system. A cycle ratio, the ratio of "on" time to "off" time, in such an intermittent reduced pressure treatment may be as low as 1:10 or as high as 10:1. The preferred ratio is approximately 1:1 which is usually accomplished in alternating 5 minute intervals of reduced pressure supply and non-supply.

A suitable vacuum system includes any suction pump capable of providing at least 0.1 pounds of suction to the wound, and preferably up to three pounds suction, and most preferably up to fourteen (14) pounds suction. The pump can be any ordinary suction pump suitable for medical purposes that is capable of providing the necessary suction. The dimension of the tubing interconnecting the pump and the reduced pressure appliance is controlled by the pump's ability to provide the suction level needed for operation. A ¼ inch diameter tube may be suitable.

The present invention also includes a method of treating damaged tissue which comprises the steps of applying negative pressure to a wound for a selected time and at a selected magnitude sufficient to reduce bacterial density in the wound. Open wounds are almost always contaminated with harmful bacteria. Generally a bacterial density of $10^5$ bacterial organisms per gram of tissue is regarded as infected. It is generally accepted that at this level of infection, grafted tissue will not adhere to a wound. These bacteria must be killed, either through the wound host's natural immune response or through some external method, before a wound will close. The application of negative pressure to a wound appears to reduce the bacterial density of the wound. It is believed that this effect is due to either the bacteria's incompatibility with a negative pressure environment or the increased blood flow to the wound area, as blood brings with it cells and enzymes to destroy the bacteria. The method can be used to reduce bacterial density in a wound by at least half. More preferably, it can be used to reduce bacterial density by at least 1,000 fold. Most preferably, the method can be used to reduce bacterial density by at least 1,000,000 fold.

The present invention also includes a method of treating a burn which comprises the steps of applying negative pressure to the burn over an area with predetermined reduced pressure and for a time sufficient to inhibit formation of a full thickness burn. A partial thickness burn, one which has a surface layer of dead tissue and an underlying zone of stasis, is often sufficiently infected so that it will transform within 24–48 hours into a full thickness burn, one in which all epidermal structures are destroyed. The application of negative pressure to the wound prevents the infection from becoming sufficiently severe to cause destruction of the underlying epidermal structures. The magnitude, pattern, and duration of pressure application can vary with the individual wound.

The present invention also provides a method for enhancing the attachment of living tissue to a wound which comprises the steps of first joining the living tissue to the wound to form a wound-tissue complex, then applying a negative or reduced pressure of selected magnitude to the wound-tissue complex over an area sufficient to promote migration of epithelia and subcutaneous tissue toward the complex, with the negative pressure being maintained for a selected time period sufficient to facilitate closure of the wound. Attachment of living tissue to a wound is a common procedure that can take many forms. For example, one common technique is the use of a "flap," a technique in which skin tissue from an area adjacent to the wound is detached on three sides but remains attached on the fourth, then is moved onto the wound. Another frequently used technique is an open skin graft in which skin is fully detached from another skin surface and grafted onto the wound. The application of negative pressure to the wound-graft complex reduces bacterial density in the complex and improves blood flow to the wound, thereby improving the attachment of the grafted tissue. Further features of the apparatus and methods for the use thereof shall be made apparent in the following examples.

EXAMPLE 1

Treatment of Open Wounds

In order to demonstrate the use of a negative pressure appliance in the treatment of open wounds, an animal study was conducted using pigs as subjects. Pigs are frequently used as subjects in wound healing studies since they have essentially the same skin and subcutaneous tissue structure as humans.

Five 15 kg Chester pigs were obtained and acclimated for 1 week prior to use. The animals were sedated with an intramuscular injection of ketamine (25 mg/kg):xylazine (2.5 mg/kg):acepromazine (5 mg/kg). The backs and sides of the animals were shaved and scrubbed for surgery. One percent halothane was administered by endotracheal tube for maintenance of anesthesia. Two circular wounds are created on the midline of the animals. The wounds were 2.5 cm in diameter having a depth reaching, but not including, the deep fascia over the spins (approximately 1 cm). Wounds in pigs in this site do not contract during healing. Alginate impressions were made of each wound to determine the volumes of the wounds.

A reduced pressure appliance of the type discussed in connection with FIGS. 2 and 11 was positioned over each wound, and the cups were sealed to the skin with an Ioban sheet. A non-compressible silicone tube was attached to the anterior appliance of each pig and a reduced pressure of 5 in. Hg below atmospheric pressure was supplied to the anterior appliances. No reduced pressure was applied to the posterior wounds. The animals were allowed to recover from anesthesia and given food and water ad libitum. The tubes were suspended from a pulley system over the top of each pen arranged to provide each animal with full, unrestricted access to its pen.

The animals were sedated 48 hours after surgery as described above, and then daily thereafter, so that alginate impressions could be made of each wound. This routine was continued until the wounded areas were filled with granulation tissue until coplanar with the surrounding tissue. The results of this experiment, including time to completer filling of the wound space by granulation tissue and the rate of granulation tissue formation, are presented in Table 1. The data in the third column of Table 1 shows the number of days needed for the treated and non-treated wounds to heal. In order to allow comparisons between the healing rate of variously-sized wounds, the data in the fourth column is expressed as a healing rate in terms of cc granulation tissue per day. As can be seen, the treated wounds exhibited higher rates of healing than did the non-treated wounds. The wounds treated with reduced pressure filled with granulation tissue at an average rate that was 52.3% greater than the rate of granulation of the control wounds. Animals numbered 1 and 2 experienced intermittent loss of reduced pressure throughout the experiment, yet the treated wounds of these animals also healed significantly faster than their control wounds.

TABLE 1

| Animal | Wound | Initial Wound Volume (cm³) | Days to Full Granulation | Fill Rate (cm³/day) | % Rate Increase Due to Treatment |
|---|---|---|---|---|---|
| #1 | Control | 4.9 | 13 | 0.38 | 26.3 |
|  | Treated | 5.3 | 11 | 0.48 |  |
| #2 | Control | 7.2 | 8 | 0.90 | 28.9 |
|  | Treated | 9.3 | 8 | 1.16 |  |
| #3 | Control | 4.0 | 12 | 0.33 | 75.8 |
|  | Treated | 3.5 | 6 | 0.58 |  |
| #4 | Control | 4.7 | 11 | 0.43 | 65.1 |
|  | Treated | 5.0 | 7 | 0.71 |  |
| #5 | Control | 4.7 | 11 | 0.43 | 65.1 |
|  | Treated | 5.1 | 7 | 0.71 |  |
| Average | — | — | — | — | 52.3 |

EXAMPLE 2

Reduction of Infection

During the course of the experiment described as Example 1 above, it was observed that the reduced pressure-treated wounds were much cleaner and bled more spontaneously than non-treated wounds. It was therefore undertaken to determine the relative rates of clearance of a known bacterial inoculum from treated and non-treated wounds.

Five 15 kg pigs were obtained and wounds created as set forth in Example 1. Two 2.5 cm diameter defects were created on the dorsum of each pig using a sterile technique, with a 7.5 cm interval retained between the edges of the defects. Hemostasis was obtained by electrocautery. Prior to placement of the reduced pressure appliances, $10^8$ organisms of *Staphylococcus aureus* in 1 ml saline solution were injected into each wound. The reduced pressure appliances of the type shown in FIGS. 2 and 11 were then attached as in Example 1, and a reduced pressure of 5 in. Hg below atmospheric pressure was applied to one of the wounds upon each animal. Reduced pressure was not applied to the other wound upon each animal. T-shirts were placed over the animals and no antibiotics were given during the course of the study. The animals were sedated as in Example 1 at 24 hour intervals, and a 3 mm diameter full thickness biopsy was taken from each wound site daily. The devices were then reattached and reduced pressure re-applied. This routine was continued for one week.

The biopsy samples were weighed and sterile saline (99× biopsy weight) added. The tissue samples were homogenized in a tissue grinder and serial dilutions were made in triplicate. 100 microliters of each dilution was plated on a blood agar plate and incubated overnight. The number of colonies were counted on each plate and thus the number of organisms per gram of tissue was calculated. The data was recorded as the common logarithm of the number of organisms/gram tissue and is shown in Table 2.

TABLE 2

|  | Average $Log_{10}$(organisms/gm) | | | | | | |
|---|---|---|---|---|---|---|---|
|  | Day 0 | Day 1 | Day 2 | Day 3 | Day 4 | Day 5 | Day 7 |
| Control | 8.44 | 8.04 | 8.17 | 7.13 | 7.13 | 8.82 | 7.08 |
| Treated | 7.69 | 7.36 | 7.37 | 6.79 | 6.43 | 3.98 | 4.32 |

As can be seen in Table 2, the common logarithm of the average number of organisms per gram of tissue present in the treated and non-treated wounds decreased slightly for all five animals over the first 4 days. In the treated wounds, the mean log of organisms/gm decreased dramatically between days 4 and 5. The mean log of organisms/gm within the non-treated wounds increased during the same period. Using the traditional baseline of $10^5$ organisms/gm to define infection, the data of Table 2 shows that the average treated wound was disinfected after four days of treatment while the average non-treated wound was still infected after 7 days.

EXAMPLE 3

Treatment of Burns

Use of reduced pressure appliances upon burns has been found to retard the progression of partial thickness burns into full thickness burns. A partial thickness burn is a burn in which the depth of cell death due to thermal trauma does not extend below the level of the deepest epidermal structures (i.e., the base of hair follicles, sweat glands, sebaceous glands, etc.). A burn that is initially a partial thickness burn will often deepen and progress into a full thickness burn due to insufficient blood circulation to the epidermal cells beneath the partial burn.

EXAMPLE 3A

The backs of five 15 kg pigs were shaved and scrubbed for surgery. A 1.5 inch diameter brass rod was heated to 190° C. in an oil bath. The rod was pressed onto the pig's skin for 15 seconds following a well-known technique of relating depth of burn to time and temperature. Three burns were created over the spine of each pig, separated by 5 cm intervals. Suction apparatus cups of the configuration shown in FIGS. 2 and 11 were placed over two of the burns, with silver sulphadiazine (Silvadine) cream, the standard antibiotic cream applied to human burns prior to excision of burned tissue, applied to the third. Cefaxolin (Kefzol) (500 mg) was administered intramuscularly (antibiotic). Suction (2–6 pounds vacuum) was applied to one of the cups. A small (2 mm) punch biopsy was taken of the wounded area and examined histologically for depth of burn.

Biopsies were analyzed by a dermatopathologist who was not told the nature of the study. It was concluded that the suctioned tissue specimens were healthier and healing more quickly than non-suctioned specimens.

EXAMPLE 3B

A set of 2 cm diameter standardized depth partial thickness burns were created by pressing a heated metal rod to each side of five anesthetized pigs to create 16 burns on each side of each pig. Reduced pressure appliances of the type shown in FIGS. 2 and 11 were secured over each of the burns on the left side of each animal and a continuous pressure of 6 in. Hg was supplied to the reduced pressure appliances. The animals were anesthetized daily, and elliptical full-thickness biopsies extending from non-injured tissue, through the center of each burn, and into non-injured tissue were harvested, fixed in formalin, processed for histological analysis and stained with Hematoxylin/eosin and Gomori's trichrome. The histologic slides were then given to a Dermatopathologist for blind determination of burn depth according to the Breslow Local Scale of maximum depth of cell death below the surface of the skin.

The Breslow Level (maximum total depth) for the burns treated by reduced pressure was 0.095 mm. The maximum depth of the burns which were not treated by reduced pressure was 0.885 mm. The use of reduced pressure appliances thus resulted in a 112% reduction in the maximum depth of burn progression.

EXAMPLE 3C

Treatment of Burn with Negative Pressure

Patient B. is admitted with second and third degree burns over the face and upper extremities, including both hands, as a result of a house fire. A large mitten-shaped reduced pressure appliance of the general type shown in FIGS. 1 and 10 is placed over the patient's right hand, with open cell foam inserts placed between the fingers to apply reduced pressure to the interdigit spaces. Three pounds of vacuum is applied cyclically in a pattern of five minutes on, 5 minutes off. The appliance is changed on a three times per week schedule. Treatment is continued until the necrotic tissue sloughs off or is excised, followed by split thickness skin graft placement.

EXAMPLE 4

Treatment of Flaps

In order to determine the effect of reduced pressure application upon skin flap survival, five 15 kg Chester pigs were obtained and acclimated for 1 week as described previously. Two dorsally-based 3 cm by 12 cm flap outlines were drawn using indelible ink on each side of the pigs, leaving 6 cm between each flap. The flaps were assigned to one of four groups as follows:

(1) Dual-treated flaps are flaps that were exposed to reduced pressure both prior to and following surgery;
(2) Pre-treated flaps are flaps that were exposed to reduced pressure prior to surgery, but were not exposed to reduced pressure after surgery;
(3) Post-treated flaps are flaps that were exposed to reduced pressure following surgery; and
(4) Control flaps are flaps that were not exposed to reduced pressure either pre- or post-surgery.

The pre-treated flaps were initially treated by covering an area surrounding one of the flap outlines on the left side of each animal with a reduced pressure appliance of the type shown in FIGS. 1 and 10 having a large piece of open cell foam into which a tube was inserted. The foam was covered and sealed to the flap area with impermeable adherent sheeting. A reduced pressure of 7 pounds was then continuously applied to the area for 7 days.

On the day of surgery, each pig was sedated as previously described and anesthesia was maintained by 1% halothane. Two 3 cm by 12 cm dorsally based flaps were created on each side of the pig following the flap outlines. The flaps were created at a depth immediately below the *panniculus carnosus* (a subcutaneous muscle layer). The flaps were raised and then sutured back in place with single, interrupted sutures of 3-0 nylon. The reduced pressure appliances were then placed over the anterior flaps on each side of the animal. A reduced pressure of 5–7 pounds was continuously applied to the anterior flaps. Each suction tube ran from the appliances on the animals upward through a pulley suspended over the pens and down to a vacuum trap bottle to collect any liquid exudate. A hose was connected from each vacuum trap bottle to a vacuum pump to supply the reduced pressure to the appliances. The animals had free access to all areas of the pen.

The animals were anesthetized 72 hours after surgery and the appliances were removed. Photographs of each side of the animals were taken, and tracings of the flaps (and encompassing any discolored areas) were made on acetate to allow for planimetric calculation of percent survival. The appliances were then replaced and reduced pressure re-applied. This routine was continued at 48 hour intervals until no further necrosis or healing of the flaps was observed.

The distal portions of all flaps were discolored 72 hours post surgery, with the flaps exposed to reduced pressure being lighter in color. The distal ends of all flaps appeared to necrose and an eschar formed over the distal portion of each flap. Over time the eschar spontaneously desquamated, exposing the outline of the original flap. The eschar over the control and pre-treated flaps consistently desquamated sooner than the post-treated and the dual-treated flaps. The control flaps had contracted to a Y shape which was evident after the eschar had desquamated. The dual-treated flaps had contracted slightly and appeared as long, thin rectangles after dislodgement of the eschar. The pre-treated flaps and post-treated flaps were intermediate between the control and dual-treated flaps in regard to flap contraction.

Dual-treated flaps exhibited the greatest survival in terms of percent retention (72.2%) of the original flap size. The post-treated flaps had the second greatest survival (67.4%). The pretreated flaps had the third most flap survival (64.8%). The control flaps had the least flap survival (51.2%). All treated flaps (dual-treated; pre-treated; and post-treated) exhibited significantly greater surface area survival than the control flaps. The dual-treated flaps had significantly greater surface area survival than either the pre-treated or post-treated flaps. The pre-treated flaps were not significantly different than post-treated flaps in regard to flap survival.

EXAMPLE 5

Treatment of Decubitus Ulcers

Application of reduced pressure was tested upon chronic decubitus ulcers and was found to be effective in the treatment thereof. Necrotic soft tissue was removed from the ulcers prior to placement upon the treatment site of a reduced pressure appliance of the type described in connection with FIGS. 1 and 10. Treatment of decubitus ulcers was tested using both continuous and cyclic application of reduced pressure. It was found that cyclic application of reduced pressure was both more effective and produced less discomfort for the patients than continuous application. Cyclic application of reduced pressure was conducted according to an application schedule of 5 minutes of suction followed by 5 minutes of non-suction. In 15 patients tested, successful treatment required from 2 to 13 weeks. Thirteen of the ulcers healed completely and every ulcer treated demonstrated progressive decrease in size during treatment. The following case histories demonstrate the manner in which various pressure sores were treated:

Case 1—A 39 year-old male T4 paraplegic had suffered from multiple recurrent pressure sores over a period of 8 years. He had been treated for a trochanteric decubitus with a tensor fascia lata flap which had developed a recurrent ulcer in the center of the flap 4 months prior to presentation. The ulcer was debrided of necrotic tissue to non-involved periosteum resulting in a wound measuring 12 cm by 5 cm with a depth of 5 cm. During the course of 4 weeks of cyclic reduced pressure application, the wound progressively closed and spontaneously re-epithelialized. Reduced pressure of 5 in. Hg below atmospheric pressure was applied cyclically with 5 minute intervals of applied pressure followed by 5 minute intervals with no applied pressure. The wound remained healed more than 5 months after treatment.

Case 2—A 45 year old male paraplegic suffered from a recurrent right ischial fossa pressure sore and abscess prior to treatment. Debridement of the wound was carried out with partial ischial resection. A week later, a re-advancement of the V-Y biceps femoris flap and rotation gluteus flap was performed. Six days later, the wound dehisced and the patient developed bilateral pneumonia requiring ventilatory support. The flap became progressively edematous and firm and resisted all efforts at mobilization. At this point, reduced pressure treatment providing continuous, non-cyclic suction or a vacuum at approximately five 5 in. Hg below atmospheric pressure was initiated. A total of 2 liters of fluid was removed by the reduced pressure appliance during the first 72 hours of treatment. Intravenous fluids were administered to replace the fluid removed from the wound. The appliance was replaced and the wound was examined three times each week. Treatment was continued for a total of six weeks during which the flap became progressively less indurated, granulation tissue formation rapidly progressed, the edges of the wound came into approximation, and the wound was healed completely.

Case 3—A 51 year-old T1 paraplegic had multiple previous pressure sores culminating in bilateral asynchronous hip disarticulations and bilateral total thigh flaps. Seven months prior to admission, he developed a 7 cm by 23 cm pressure sore over the remnants of both ischia. Bone was exposed and no tissue was available for wound closure. Dressing changes over a period of three months had failed to improve the wound. A reduced pressure appliance was then secured to the wound. During the first 3 weeks of treatment, reduced pressure of 5 in. Hg below atmospheric pressure was continuously applied. For the following 9 weeks, reduced pressure was applied cyclically in 5 minute intervals. The appliance was replaced every three days during treatment. In the course of the treatment, the wound first granulated to cover the bone completely and then the wound re-epithelialized from the margins. After 12 weeks of the treatment, a 2 cm by 5 cm scrotal flap was used to cover the midline area of the wound. The wound has remained stable beyond 6 months after treatment.

EXAMPLE 6

Treatment of Dehisced Incisions

A 50 year old debilitated white male who had undergone a colostomy through a midline laparotomy was re-admitted to the hospital for wound dehiscence and evisceration following an upper respiratory infection. He was taken immediately to the operating room and the abdominal wall was closed with Prolene mesh. Six weeks after placement of the Prolene mesh, the wound was still open and measured 28 cm by 23 cm. Only sparse granulation tissue had grown through the Prolene mesh during the six weeks. At this time a large reduced pressure appliance of the type shown in FIG. 5 was placed on an underlying porous aquaplast sheet (WFR/Aquaplast Corp., Wycoff, N.J. 07481) over top of the Prolene mesh/wound surface and the space closed with a covering tent of Ioban. A continuous vacuum of 5 in. Hg below atmospheric pressure was applied. The appliance was changed three times per week. After 8 days of treatment, granulation tissue had grown through and totally covered the Prolene mesh. Two days later, the patient was taken to the operating room, where the surrounding tissue was undermined and used to close 75% of the wound. Split thickness skin grafts were used to cover the remainder of the wound, and were placed on the bed of granulation tissue. There was 80% take of the grafts, and the remaining areas healed spontaneously with wet to dry dressing changes. The wound has remained stable 16 months after surgery.

EXAMPLE 7

Treatment of Infected Wound

Infected wounds have been successfully treated via application of reduced pressure as described in the following cases:

Case 1—A 39 year old white male sustained severe avulsive trauma to his left lower extremity in a motor vehicle accident 10 years prior to presentation. He presented with a ten year history of chronic osteomyelitis and a 3 cm diameter open ulcer with exposure of bone of his left lateral malleolus. He had previously undergone 7 local surgical procedures to attempt closure of the wound. An arteriogram demonstrated a one vessel foot with diffuse athereosclerosis and post traumatic changes. The extremity was debrided of necrotic soft tissue and all involved bone saucerized. The patient was placed on a five week course of antibiotics. The day after debridement, a reduced pressure device of the type shown in FIGS. 2 and 11 was applied over the wound and a reduced pressure of 5 in. Hg below atmospheric pressure was applied. The device was changed on a three times per week schedule. After 14 days of treatment, the wound was smaller and filled with granulation tissue which completely covered the previously exposed bone. A split thickness skin graft was placed over the wound and healed primarily. The wound has been stable for 13 months with no recurrence of osteomyelitis or tissue breakdown.

Case 2—A 51 year old white male T8 paraplegic was admitted to the hospital for an infected left trochanteric pressure sore which had been present for one year and measured 4 cm by 6 cm. The patient had previously undergone multiple procedures for treatment of this condition including a V-Y advancement flap 4 months prior to presentation. A scan revealed possible chronic osteomyelitis of the left femur. It was decided to treat the potential osteomyelitis with a five week course of IV antibiotics. The wound was debrided, then treated using a reduced pressure appliance of the type shown in FIGS. 1 and 10 for 6 weeks with cyclical reduced pressure (5 in. Hg below atmospheric pressure; 5 minutes on/5 minutes off). The wound rapidly granulated and decreased in size. After 6 weeks the wound had closed and the patient discharged. The patient was readmitted 1 month later with a draining sinus tract to the bone. The previously scanned head of the left femur was resected and the wound closed primarily over drains. The wound healed without further problems.

EXAMPLE 8

Chronic Open Wound Secondary to Stasis Ulcers

A 45 year old black female patient with a 10 year history of bilateral stasis ulcers of the pretibial area was presented with bilateral 10 cm by 15 cm infected ulcers with exposed fascia. Two previous attempts at skin grafting in the previous year had failed. The patient was treated using a reduced pressure appliance of the type shown in FIGS. 1 and 10 for 14 days with cyclical (5 minutes on/5 minutes off) reduced pressure of approximately 5 in. Hg below atmospheric pressure. After 14 days treatment, quantitative bacterial counts of both ulcers were below 102 bacteria/gram tissue, and both ulcers appeared as healthy granulating beds. Split thickness skin grafts were then applied and exhibited 100% take. The patient is ambulating, and the wounds have remained healed for 2 months, which is the longest the wounds had been healed in the last 10 years.

EXAMPLE 9

Enhancement of Blood Flow

It is believed that the efficacy of reduced pressure appliances in such treatments as have been described is due at least in part to enhancement of blood circulation within the treated wounds. In order to determine the effect of pressure application upon blood flow, a laser doppler needle probe was inserted into tissue adjacent to a pressure sore. A baseline flow level was recorded for thirty minutes. Then, the relative blood flow level was measured while a reduced pressure corresponding to 5 in. Hg below atmospheric pressure was continuously applied to the wound for 30 minutes using a reduced pressure appliance of the type shown in FIGS. 1 and 10. During continuous reduced pressure application, the relative blood flow level was only slightly higher than the baseline level.

Then the supply of reduced pressure to the appliance was cycled on and off at equal 5 minute intervals. During the "off" portions of the cycle, the relative blood flow level was twice as high as the baseline level. It is postulated that the increased blood flow during the off cycle is likely due to a "rebound" phenomenon. During the "on" cycle, blood is drawn toward the wounded tissue from both the venous and arterial branches of the vascular network in the vicinity of the wound. During the "off" cycle, this blood is transported toward the venous branch of the vascular network at a rate that is greater than would have been observed in the absence of the preceding "on" cycle.

The terms and expressions which have been employed are used as terms of description and not of limitation and there is no intention in the use of such terms and expressions of excluding any equivalents of the features shown and described, or portions thereof, but it is recognized that various modifications are possible within the scope of the claimed invention.

What is claimed is:

1. An appliance for administering a reduced pressure treatment to a wound comprising:
    (a) an impermeable cover adapted to cover and enclose the wound and to maintain reduced pressure at the site of the wound;
    (b) a seal operably connected with the cover for sealing said cover to tissue surrounding the wound;
    (c) support means separate from said cover configured for holding said cover out of contact with the wound without said support means contacting the wound; and
    (d) reduced pressure supply means operably connected with the cover for connection to a source of suction, said reduced pressure supply means cooperating with said cover to supply and maintain said reduced pressure beneath the cover.

2. The appliance as recited in claim 1 comprising a screen for preventing overgrowth of wound tissue, said screen being positioned between said wound and said cover.

3. The appliance as recited in claim 2 wherein said screen comprises a porous sheet.

4. The appliance as recited in claim 1 wherein said reduced pressure is from about 2 in. Hg below atmospheric pressure to about 7 in. Hg below atmospheric pressure.

5. An appliance for administering a reduced pressure treatment to a wound comprising:
    (a) an impermeable cover adapted to cover and enclose the wound and to maintain reduced pressure at the site of the wound;
    (b) a seal operably connected with the cover for sealing said cover to tissue surrounding the wound, the seal including a cuff around the periphery of said cover for preventing said cover from digging into the skin during the treatment;
    (c) support means separate from said cover for holding said cover out of contact with the wound; and
    (d) reduced pressure supply means operably connected with the cover for connection to a source of suction, said reduced pressure supply means cooperating with said cover to supply and maintain said reduced pressure beneath the cover.

6. The appliance as recited in claim 1 wherein said seal includes an adhesive material located on the cover for securing said cover to the tissue surrounding the wound.

7. The appliance of claim 1 wherein said cover comprises a flexible sheet.

8. The appliance of claim 7 wherein the support means connects with said sheet for supporting said sheet outward from the wound.

9. The appliance of claim 8 wherein said support means comprises a support member located between said sheet and the wound.

10. An appliance for administering a reduced pressure treatment to a wound comprising:
    (a) an impermeable cover adapted to cover and enclose the wound and to maintain reduced pressure at the site of the wound, the cover comprising a flexible sheet;
    (b) a seal operably connected with the cover for sealing said cover to tissue surrounding the wound;
    (c) support means separate from said cover for holding said cover out of contact with the wound, wherein the support means connects with said sheet for supporting said sheet outward from the wound and wherein the support means comprises a support member located between said sheet and the wound, the support member including a porous cup member having a connection port for connecting with said reduced pressure supply means; and
    (d) reduced pressure supply means operably connected with the cover for connection to a source of suction, said reduced pressure supply means cooperating with said cover to supply and maintain said reduced pressure beneath the cover.

11. An appliance for administering a reduced pressure treatment to a wound comprising:
    (a) an impermeable cover adapted to cover and enclose the wound and to maintain reduced pressure at the site of the wound, the cover comprising a flexible sheet;
    (b) a seal operably connected with the cover for sealing said cover to tissue surrounding the wound;
    (c) support means separate from said cover for holding said cover out of contact with the wound, wherein the support means connects with said sheet for supporting said sheet outward from the wound and wherein the support means comprises a support member located between said sheet and the wound;
(d) reduced pressure supply means operably connected with the cover for connection to a source of suction, said reduced pressure supply means cooperating with said cover to supply and maintain said reduced pressure beneath the cover; and
(e) a pad between the wound and said support member for alleviating discomfort caused in the wound by said support member.

12. An appliance for administering a reduced pressure treatment to a wound comprising:
   (a) an impermeable cover adapted to cover and enclose the wound and to maintain reduced pressure at the site of the wound, the cover comprising a flexible sheet;
   (b) a seal operably connected with the cover for sealing said cover to tissue surrounding the wound;
   (c) support means separate from said cover for holding said cover out of contact with the wound, wherein the support means connects with said sheet for supporting said sheet outward from the wound and wherein the support means comprises a support member extending outwardly over the wound and external to said sheet; and
   (d) reduced pressure supply means operably connected with the cover for connection to a source of suction, said reduced pressure supply means cooperating with said cover to supply and maintain said reduced pressure beneath the cover.

13. The appliance of claim 12 wherein said support means comprises attachment means for attaching said sheet to said support means, said attachment means having a connecting member for connecting with said reduced pressure supply means for providing said reduced pressure beneath said sheet, and said support member comprising a plurality of leg members attached to said attachment means for holding said attachment means and said sheet outward from the wound.

14. The appliance as recited in claim 12 comprising a pad positioned between edges of the sheet and the tissue surrounding the wound.

15. The appliance of claim 13 comprising a screen adapted to prevent overgrowth of the wound for placement at a location between the wound and said cover and which is secured in said location at the periphery of said cover.

16. The appliance of claim 15 wherein said screen comprises a mesh.

17. The appliance of claim 15 wherein said seal includes an adhesive material located on the cover for adhering to tissue surrounding the wound and a seal member at least partially overlying said cover.

18. An appliance for administering a reduced pressure treatment to a wound comprising:
   (a) an impermeable cover adapted to cover and enclose the wound and to maintain reduced pressure at the site of the wound, the cover comprising a flexible sheet;
   (b) a seal operably connected with the cover for sealing said cover to tissue surrounding the wound;
   (c) support means separate from said cover for holding said cover out of contact with the wound, wherein
      the support means connects with said sheet for supporting said sheet outward from the wound, the support means comprises a support member located between said sheet and the wound, and the support means includes a convex shield and wherein the flexible sheet overlies and extends beyond the shield at the periphery of the sheet; and
   (d) reduced pressure supply means operably connected with the cover for connection to a source of suction, said reduced pressure supply means cooperating with said cover to supply and maintain said reduced pressure beneath the cover.

19. The appliance as recited in claim 18 wherein the seal cooperates with a portion of the flexible sheet that extends beyond the shield to seal the cover.

20. The appliance as recited in claim 1 wherein said support means is separate from said cover.

21. The appliance as recited in claim 1 comprising only a single port associated with said cover for connecting said reduced pressure supply means to said cover.

22. An apparatus for treating a wound comprising:
   (a) a vacuum system for producing a reduced pressure; and
   (b) a reduced pressure appliance operably connected with said vacuum system for applying said reduced pressure to the wound, the appliance including:
      (i) an impermeable cover adapted to cover and enclose the wound and to maintain reduced pressure at the site of the wound;
      (ii) support means separate from said cover configured for holding said cover out of contact with the wound without said support means contacting the wound;
      (iii) a seal operably connected with the cover for sealing said cover to tissue surrounding the wound; and
      (iv) reduced pressure supply means operably connected with the cover for connection with the vacuum system for supplying and maintaining said reduced pressure to the wound.

23. The apparatus as recited in claim 22 wherein said vacuum system includes a collection device for collecting fluid aspirated from the wound.

24. An apparatus for treating a wound comprising:
   (a) a vacuum system for producing a reduced pressure, the vacuum system including a collection device for collecting fluid aspirated from the wound, the collection device including means for halting said application of reduced pressure to the wound when said fluid exceeds a predetermined quantity;
   (b) a reduced pressure appliance operably connected with said vacuum system for applying said reduced pressure to the wound, the appliance including:
      (i) an impermeable cover adapted to cover and enclose the wound and to maintain reduced pressure at the site of the wound;
      (ii) support means separate from said cover for holding said cover out of contact with the wound;
      (iii) a seal operably connected with the cover for sealing said cover to tissue surrounding the wound; and
      (iv) reduced pressure supply means operably connected with the cover for connection with the vacuum system for supplying and maintaining said reduced pressure to the wound.

25. The apparatus of claim 24 wherein said reduced pressure supply means comprises a length of tubing, said collection device comprises an aspirating container connected along said length of tubing between said vacuum system and cover, and said halting means comprises a flotation valve within said aspirating container for blocking said tubing when a predetermined amount of fluid is collected within said container.

26. The apparatus of claim 24 wherein said collection device comprises an expandable chamber and said means for halting said application of reduced pressure comprises sensing means for sensing expansion of said expandable chamber, said sensing means operatively connected with said vacuum system so that said reduced pressure is halted when a predetermined expansion of said expandable chamber is sensed by said sensing means.

27. The apparatus of claim 24 wherein said reduced pressure supply means comprises a length of tubing and said halting means comprises a filter along said tubing, said filter having pores that block the supply of reduced pressure via said tubing when said pores are filled with said fluid.

28. The apparatus as recited in claim 22 wherein said reduced pressure is from about 2 in. Hg below atmospheric pressure to about 7 in. Hg below atmospheric pressure.

29. An apparatus for treating a wound comprising:
(a) a vacuum system for producing a reduced pressure comprising
  (i) a vacuum pump connected with said tubing; and
  (ii) a filter for preventing said pump from venting micro-organisms aspirated from the wound; and
(b) a reduced pressure appliance operably connected with said vacuum system for applying said reduced pressure to the wound, the appliance including:
  (i) an impermeable cover adapted to cover and enclose the wound and to maintain reduced pressure at the site of the wound;
  (ii) support means separate from said cover for holding said cover out of contact with the wound;
  (iii) a seal operably connected with the cover for sealing said cover to tissue surrounding the wound; and
  (iv) reduced pressure supply means operably connected with the cover for connection with the vacuum system for supplying and maintaining said reduced pressure to the wound, the reduced pressure supply means comprising a length of tubing connected between said vacuum system and said cover.

30. The apparatus of claim 29 wherein said filter is connected along said tubing between said pump and said cover for preventing contamination of said pump.

31. An apparatus for treating a wound comprising:
(a) a vacuum system for producing a reduced pressure comprising control means for cyclically controlling said production of reduced pressure in alternating periods of production and non-production of reduced pressure; and
(b) a reduced pressure appliance operably connected with said vacuum system for applying said reduced pressure to the wound, the appliance including:
  (i) an impermeable cover adapted to cover and enclose the wound and to maintain reduced pressure at the site of the wound;
  (ii) support means separate from said cover for holding said cover out of contact with the wound;
  (iii) a seal operably connected with the cover for sealing said cover to tissue surrounding the wound; and
  (iv) reduced pressure supply means operably connected with the cover for connection with the vacuum system for supplying and maintaining said reduced pressure to the wound.

32. The apparatus as recited in claim 22 comprising only a single port associated with said cover for connecting said reduced pressure supply means to said cover.

33. A method of treating a wound comprising the steps of:
(a) applying a reduced pressure to the wound, wherein said applying step comprises steps of:
  (i) locating an impermeable cover over the wound, said cover having a suction port;
  (ii) providing a separate support to support said cover out of contact with the wound without said support means contacting the wound;
  (iii) sealing the periphery of said impermeable cover to tissue surrounding the wound; and
  (iv) operably connecting said suction port with a vacuum system for producing said reduced pressure; and
(b) maintaining said reduced pressure until the wound has progressed toward a selected stage of healing.

34. The method as recited in claim 33 further comprising the step of placing a porous screen over the wound prior to said locating step.

35. The method of claim 33 wherein said maintaining step is conducted in alternating periods of application and non-application of the negative pressure.

36. The method of claim 35 wherein each of said alternating periods is about 5 minutes.

37. A method of treating a wound comprising the steps of:
(a) applying a reduced pressure to the wound, wherein said applying step comprises steps of:
  (i) locating an impermeable cover over the wound, said cover having a suction port;
  (ii) providing a separate support to support said cover out of contact with the wound;
  (iii) sealing the periphery of said impermeable cover to tissue surrounding the wound; and
  (iv) operably connecting said suction port with a vacuum system for producing said reduced pressure; and
(b) maintaining said reduced pressure until the wound has progressed toward a selected stage of healing comprising a cessation of partial thickness burn progression.

38. A method of treating a wound comprising the steps of:
(a) applying a reduced pressure to the wound, wherein said applying step comprises steps of:
  (i) locating an impermeable cover over the wound, said cover having a suction port;
  (ii) providing a separate support to support said cover out of contact with the wound;
  (iii) sealing the periphery of said impermeable cover to tissue surrounding the wound; and
  (iv) operably connecting said suction port with a vacuum system for producing said reduced pressure; and
(b) maintaining said reduced pressure until the wound has progressed toward a selected stage of healing comprising a reduction in bacterial density in the wound of at least 50%.

39. The method as recited in claim 33 wherein said reduced pressure is from about 2 in. Hg below atmospheric pressure to about 7 in. Hg below atmospheric pressure.

40. A method of promoting attachment of a skin flap onto a wound comprising steps of:
(a) applying reduced pressure to a region of skin adjacent to the wound,
(b) forming the flap by detaching skin from said region,
(c) attaching the flap to the wound, and
(d) applying and maintaining reduced pressure to the flap to promote blood circulation within the flap.

41. An appliance for administering a reduced pressure treatment to a wound comprising:
  a. an impermeable cover adapted to cover and enclose the wound and to maintain reduced pressure at the site of the wound, wherein said cover is sufficiently rigid to support said cover out of contact with the wound;

b. a seal adapted to seal said cover to tissue surrounding the wound wherein said seal includes a cuff around the periphery of said cover for preventing said cover from digging into the skin during the treatment; and c. reduced pressure supply means adapted to connect to a source of suction, said reduced pressure supply means cooperating with said cover to supply said reduced pressure beneath the cover, and said reduced pressure supply means comprising a suction port on said cover.

42. A method of treating a wound comprising the steps of:

a. applying a reduced pressure to the wound, wherein said reduced pressure is from about 2 in. Hg below atmospheric pressure to about 7 in. below atmospheric pressure; and b. maintaining said reduced pressure until the wound has progressed toward cessation of partial thickness burn progression.

43. The method as recited in claim 42 wherein said applying step comprises the steps of:

a. locating an impermeable cover over the wound, said cover having a suction port;

b. sealing the periphery of said impermeable cover to tissue surrounding the wound; and c. operably connecting said suction port with a vacuum system for producing said reduced pressure.

44. A method of treating a wound comprising the steps of:

a. applying a reduced pressure to the wound, wherein said reduced pressure is from about 2 in. Hg below atmospheric pressure to about 7 in. Hg below atmospheric pressure; and b. maintaining said reduced pressure until the wound has progressed toward at least a 50% reduction in bacterial density in the wound.

45. The method as recited in claim 44 wherein said applying step comprises the steps of:

a. locating an impermeable cover over the wound, said cover having a suction port;

b. sealing the periphery of said impermeable cover to tissue surrounding the wound; and c. operably connecting said suction port with a vacuum system for producing said reduced pressure.

* * * * *

(12) EX PARTE REEXAMINATION CERTIFICATE (6572nd)
United States Patent
Argenta et al.

(10) Number: US 7,198,046 C1
(45) Certificate Issued: *Dec. 16, 2008

(54) WOUND TREATMENT EMPLOYING REDUCED PRESSURE

(75) Inventors: Louis C. Argenta, Winston-Salem, NC (US); Michael J. Morykwas, Pfafftown, NC (US)

(73) Assignee: Wake Forest University Health Sciences, Winston-Salem, NC (US)

Reexamination Request:
No. 90/008,711, Oct. 5, 2007

Reexamination Certificate for:
Patent No.: 7,198,046
Issued: Apr. 3, 2007
Appl. No.: 09/026,353
Filed: Feb. 19, 1998

( * ) Notice: This patent is subject to a terminal disclaimer.

Related U.S. Application Data

(63) Continuation of application No. 08/467,243, filed on Jun. 6, 1995, now abandoned, which is a continuation of application No. 08/028,677, filed on Mar. 9, 1993, now Pat. No. 5,636,643, which is a continuation-in-part of application No. 07/792,001, filed on Nov. 14, 1991, now Pat. No. 5,645,081.

(51) Int. Cl.
*A61B 19/00* (2006.01)

(52) U.S. Cl. .......................................... 128/897; 602/42
(58) Field of Classification Search .................. None
See application file for complete search history.

(56) References Cited

U.S. PATENT DOCUMENTS 1,000,001 A    8/1911  Holz

| 2,122,121 A | 6/1938 | Tillotson |
| 2,221,758 A | 11/1940 | Elmquist |
| 2,443,481 A | 6/1948 | Sene |
| 2,573,791 A | 11/1951 | Howells |

(Continued)

FOREIGN PATENT DOCUMENTS

| DE | 372727 | 3/1923 |
| DE | 847475 | 7/1949 |
| DE | 3102674 | 9/1982 |
| DE | 3539533 | 5/1987 |
| DE | 4111122 | 4/1993 |

(Continued)

OTHER PUBLICATIONS

P. Svedman et al., A Dressing System Providing Fluid Supply and Suction Drainage Used for Continuous or Intermittent Irrigation, Annals of Plastic Surgery, vol. 17, No. 2, Aug. 1986, pp. 125–133.

P. Svedman et al., A Dressing System Providing Fluid Supply and Suction Drainage Used for Continuous or Intermittent Irrigation, Annals of Plastic Surgery, vol. 17, No. 2, Aug. 1986, pp. 125–133.

(Continued)

*Primary Examiner*—Beverly M. Flanagan

(57) ABSTRACT

A method of treating tissue damage comprises applying a negative pressure to a wound sufficient in time and magnitude to promote tissue migration and thus facilitate closure of the wound. The method is applicable to wounds, burns, infected wounds, and live tissue attachments. A wound treatment apparatus is provided in which a fluid impermeable wound cover is sealed over a wound site. A screen in the form of an open-cell foam screen or a rigid porous screen is placed beneath the wound cover over the wound. A vacuum pump supplies suction within the wound cover over the treatment site.

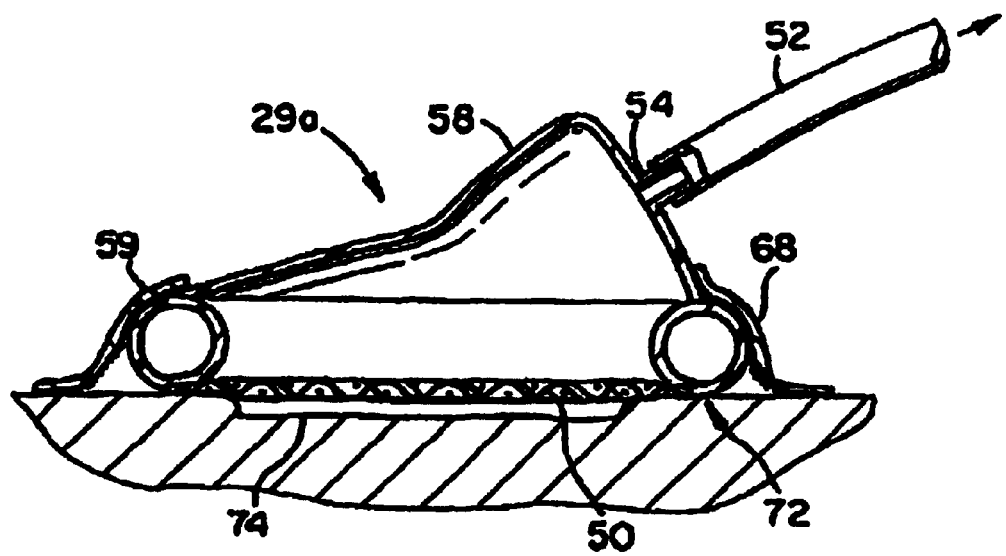

U.S. PATENT DOCUMENTS

| | | |
|---|---|---|
| 2,577,945 A | 12/1951 | Atherton |
| 2,632,443 A | 3/1953 | Lesher |
| 2,682,873 A | 7/1954 | Evans |
| 2,910,763 A | 11/1959 | Lauterbach |
| 3,315,665 A | 4/1967 | MacLeod |
| 3,528,416 A | 9/1970 | Chamberlain |
| 3,568,675 A | 3/1971 | Harvey |
| 3,648,692 A | 3/1972 | Wheeler |
| 3,782,377 A | 1/1974 | Rychlik |
| 3,812,972 A | 5/1974 | Rosenblum |
| 3,814,095 A | 6/1974 | Lubens |
| 3,903,882 A | 9/1975 | Augurt |
| 3,935,863 A | 2/1976 | Kliger |
| 3,976,060 A | 8/1976 | Hildebrandt |
| 3,998,227 A | 12/1976 | Holbrook et al. |
| 4,157,715 A | 6/1979 | Westerhoff |
| 4,184,510 A | 1/1980 | Murry et al. |
| 4,191,204 A | 3/1980 | Nehring |
| 4,256,109 A | 3/1981 | Nichols |
| 4,341,209 A | 7/1982 | Schaar |
| 4,382,441 A | 5/1983 | Svedman |
| 4,399,816 A | 8/1983 | Spangler |
| 4,457,755 A | 7/1984 | Wilson |
| 4,465,485 A | 8/1984 | Kashmer et al. |
| 4,533,352 A | 8/1985 | Van Beek |
| 4,553,967 A | 11/1985 | Ferguson |
| 4,576,158 A | 3/1986 | Boland |
| 4,579,555 A | 4/1986 | Russo |
| 4,615,338 A | 10/1986 | Ilizarov |
| 4,633,863 A | 1/1987 | Filips |
| 4,637,819 A | 1/1987 | Ouellette |
| 4,641,643 A | 2/1987 | Greer |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,710,165 A | 12/1987 | McNeil et al. |
| 4,733,659 A | 3/1988 | Edenbaum |
| 4,747,166 A | 5/1988 | Kuntz |
| 4,778,446 A | 10/1988 | Jensen |
| 4,822,278 A | 4/1989 | Oliva |
| 4,846,162 A | 7/1989 | Moehring |
| 4,872,450 A | 10/1989 | Austad |
| 4,877,019 A | 10/1989 | Vives |
| 4,890,608 A | 1/1990 | Steer |
| 4,897,081 A | 1/1990 | Poirier |
| 4,906,240 A | 3/1990 | Reed |
| 4,973,331 A | 11/1990 | Pursley |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya |
| 5,002,528 A | 3/1991 | Palestrant |
| 5,002,529 A | 3/1991 | Cunningham |
| 5,002,543 A | 3/1991 | Bradshaw |
| 5,003,971 A | 4/1991 | Buckley |
| 5,014,389 A | 5/1991 | Ogilvie |
| 5,019,086 A | 5/1991 | Neward |
| 5,034,003 A | 7/1991 | Denance |
| 5,034,006 A | 7/1991 | Hosoda |
| 5,034,012 A | 7/1991 | Frigg |
| 5,042,978 A | 8/1991 | Quenin et al. |
| 5,060,662 A | 10/1991 | Farnswoth, III |
| 5,073,172 A | 12/1991 | Fell |
| 5,086,763 A | 2/1992 | Hathman |
| 5,100,404 A | 3/1992 | Hayes |
| 5,101,808 A | 4/1992 | Kobayashi |
| 5,102,413 A | 4/1992 | Podder |
| 5,103,806 A | 4/1992 | McLeod |
| 5,106,629 A | 4/1992 | Cartmell |
| 5,135,518 A | 8/1992 | Vera |
| 5,147,338 A | 9/1992 | Lang |
| 5,152,757 A | 10/1992 | Eriksson |
| 5,152,794 A | 10/1992 | Davidson |
| 5,160,322 A | 11/1992 | Scheremet |
| 5,167,613 A | 12/1992 | Karami |
| 5,170,781 A | 12/1992 | Loomis |
| 5,176,663 A | 1/1993 | Svedman |
| 5,176,667 A | 1/1993 | DeBring |
| 5,178,137 A | 1/1993 | Goor |
| 5,191,880 A | 3/1993 | McLeod |
| 5,215,539 A | 6/1993 | Schoolman |
| 5,217,009 A | 6/1993 | Kronberg |
| 5,224,947 A | 7/1993 | Cooper |
| 5,230,350 A | 7/1993 | Fentress |
| 5,242,448 A | 9/1993 | Pettine |
| 5,263,922 A | 11/1993 | Sova |
| 5,263,955 A | 11/1993 | Baumgart |
| 5,298,015 A | 3/1994 | Komatsuzaki |
| 5,349,965 A | 9/1994 | McCarver |
| 5,356,411 A | 10/1994 | Spievack |
| 5,358,494 A | 10/1994 | Svedman |
| 5,376,065 A | 12/1994 | McLeod |
| 5,376,252 A | 12/1994 | Ekstrom |
| 5,395,315 A | 3/1995 | Griep |
| 5,419,768 A | 5/1995 | Kayser |
| 5,429,638 A | 7/1995 | Muschler |
| 5,431,662 A | 7/1995 | Nicholas |
| 5,445,604 A | 8/1995 | Lang |
| 5,451,215 A | 9/1995 | Wolter |
| 5,484,427 A | 1/1996 | Gibbons |
| 5,487,889 A | 1/1996 | Eckert |
| 5,520,652 A | 5/1996 | Peterson |
| 5,527,293 A | 6/1996 | Zamierowski |
| 5,626,579 A | 5/1997 | Muschler |
| 5,645,081 A | 7/1997 | Argenta |
| 5,678,564 A | 10/1997 | Lawrence |
| 5,697,920 A | 12/1997 | Gibbons |
| 5,911,222 A | 6/1999 | Lawrence |
| 5,954,680 A | 9/1999 | Augustine |
| 5,964,723 A | 10/1999 | Augustine |
| 5,986,163 A | 11/1999 | Augustine |
| 6,071,254 A | 6/2000 | Augustine |
| 6,110,197 A | 8/2000 | Augustine |
| 6,113,561 A | 9/2000 | Augustine |
| 6,143,945 A | 11/2000 | Augustine |
| 6,213,965 B1 | 4/2001 | Augustine |
| 6,213,966 B1 | 4/2001 | Augustine |
| 6,217,535 B1 | 4/2001 | Augustine |
| 6,235,047 B1 | 5/2001 | Augustine |
| 6,241,697 B1 | 6/2001 | Augustine |
| 6,241,698 B1 | 6/2001 | Augustine |
| 6,264,622 B1 | 7/2001 | Augustine |
| 6,264,979 B1 | 7/2001 | Svedman |

FOREIGN PATENT DOCUMENTS

| | | |
|---|---|---|
| DE | 19722075 | 10/1998 |
| DK | 64055 | 10/1945 |
| EP | 0117632 | 9/1984 |
| EP | 0424165 | 4/1991 |
| EP | 0485657 | 5/1992 |
| EP | 0547496 | 6/1993 |
| EP | 0620720 B2 | 10/1994 |
| EP | 0688189 | 12/1995 |
| FR | 500253 | 3/1920 |
| FR | 1303238 | 9/1962 |
| GB | 190203090 | 6/1902 |
| GB | 1549756 | 8/1979 |
| GB | 2 195 255 | 4/1988 |
| GB | 2195255 | 7/1988 |
| SE | 84485 | 10/1935 |

| SU | 587941 | 1/1978 |
| SU | 1268175 | 11/1986 |
| WO | WO 87/04626 | 8/1987 |
| WO | 87/04626 | 8/1987 |
| WO | WO 89/04158 | 5/1989 |
| WO | 90/10424 | 9/1990 |
| WO | WO 90/10424 | 9/1990 |
| WO | 94/00090 | 1/1994 |
| WO | 94/20041 | 9/1994 |

OTHER PUBLICATIONS

P. Svedman, Irrigation Treatment of Leg Ulcers, The Lancet, Sep. 3, 1983, pp. 532–534.

Egnell Minor, Instruction Book, First Edition, 300 7502, Feb. 1975.

U.S. Appl. No. 10/647,068—Official Action P02977US1–OA–10 (Jan. 17, 2008).

Meehan, P.A., "Open abdominal wounds: a creative approach to a challenging problem", Progressions, 4(2):3–8, 11 (1992). NPL–276.

EP 0 620 720 (DE 692 24 847) Nullity Action filed by Molnlycke Health Care AB at the German Federal Patent Court to nullify EP 0 620 720 (DE 692 24 847) (EP equivalent of US 5645081) and English translation, dated Mar. 10, 2008. MolnlyckeDEWH1–001.

Classification of features of Claim 1 of EP 0 620 720 B2 (EP equivalent of US 5645081) labeled as "Anlage MFP1" in German with English translation (attachment to Nullity Action filed by Molnlycke on Mar. 20, 2008). MolnlyckeDEWH1–002.

Thomas, S., "Wound management and dressings," cover sheet, preface, sheet labeled "Chapter 5" and pp. 36–39 (1990). MolnlyckeDEWH1–003.

EP 0 620 720 Revocation Proceeding filed by Molnlycke Health Care AB at the UK High Court of Justice Chancery Division, Patents Court, Royal Courts of Justice, to revoke EP 0 620 720 (EP equivalent of US 5645081), dated Mar. 14, 2008. MolnlyckeUKWH1–001.

*KCI et al.* v. *Blue Sky Medical Group et al.,* Case No. 2007–1340, –1341, –1342, Plaintiff–Cross Appellant's (Patent Owner's) Brief, with addendum chart, filed on Mar. 3, 2008. CAFC1340–002.

*KCI et al.* v. *Blue Sky Medical Group et al.,* Case No. 2007–1340, –1341, –1342, Reply brief of appellants, Medela AG and Medela, Inc., filed by Medela on May 15, 2008. CAFC1340–003.

*KCI et al.* v. *Blue Sky Medical Group et al.,* Case No. 2007–1340, –1341, –1342, Response and reply brief of defendant–appellant, Blue Sky Medical Group Inc., filed by Blue Sky on May 15, 2008. CAFC1340–004.

U.S. Appl. No. 10/161,076—Applicants' response P02915US0–OA–11 (Mar. 14, 2008).

U.S. Appl. No. 10/227,161—Applicants+ response P02977US0–OA–13 (Jan. 30, 2007).

U.S. Appl. No. 10/647,068—Applicants' response P02977US1–OA–11 (Jan. 30, 2007).

Svedman, P., et al., "A dressing system providing fluid supply and suction drainage used for continuous or intermittent irrigation", Ann. Plast. Surg., 17(2):125–33 (Aug. 1986). NPL–389__.

"Pressure equivalents," McGraw–Hill Encyclopedia of Science & Technology, 6th ed., New York, pp. 249, (1987). NPL–687bw.

*ITI* v. *KCI,* Case No. 07–589, Reply brief in support of defendants' motion to dismiss complaint, filed by KCI on Dec. 12, 2007. DED–005.

*ITI* v. *KCI,* Case No. 07–589, First amended complaint, filed by ITI on Jan. 25, 2008. DED–006.

*ITI* v. *KCI,* Case No. 07–589, Defendants' motion, Proposed order, and Opening brief in support of defendants' motion to dismiss first amended complaint, or, alternatively, to transfer the case to the Middle District of North Carolina, filed by KCI on Mar. 12, 2008. DED–007.

*ITI* v. *KCI,* Case No. 07–589, Plaintiff's opposition to defendants' motion to dismiss, with declarations, filed by ITI on Apr. 4, 2008. DED–008.

*ITI* v. *KCI,* Case No. 07–589, Reply brief in support of defendants' motion to dismiss first amended complaint, or, alternatively, to transfer the case to the Middle District of North Carolina, filed by KCI on Apr. 21, 2008. DED–009.

*KCI* v. *Medela,* Case No. 08–cv–00087, (formerly 2:07cv187), Plaintiff's memorandum in support of continuing to stay litigation pending reexamination of U.S. Patent No. 7,216,651 and conclusion of related appeal, filed by Medela on May 9, 2008. SA087–001.

*KCI* v. *Medela,* Case No. 08–cv–00087, (formerly 2:07cv187), Plaintiffs KCI's and Wake Forest's brief in opposition to Medela's motion to stay, Proposed order denying Medela's motion to stay, with Exhibits, filed by KCI on May 16, 2008. SA087–002.

*KCI* v. *Medela,* Case No. 08–cv–00087, (formerly 2:07cv187), Defendants' reply to KCI's and Wake Forest's Brief in opposition to continue to stay litigation pending reexamination of U.S. Patent No. 7,216,651 and conclusion of related appeal, with Proposed order, filed by Medela on May 21, 2008. SA087–003.

*KCI, et al.,* v. *Blue Sky Medical Group, Inc., et al.,* SA08–cv–102, (formerly 2:07cv188), Defendants Blue Sky Medical Group, Inc.'s and Smith & Nephew, Inc.'s motion to stay, with Proposed order and Exhibits, filed by Blue Sky on May 9, 2008. SA00102–001.

*KCI, et al.,* v. *Blue Sky Medical Group, Inc., et al.,* SA08–cv–102, (formerly 2:07cv188), Plaintiffs KCI's and Wake Forest's brief in opposition to defendants' motion to stay, with Proposed order and Exhibits, filed by KCI on May 16, 2008. SA00102–002.

*KCI, et al.,* v. *Blue Sky Medical Group, Inc., et al.,* SA08–cv–102, (formerly 2:07cv188), Defendants Blue Sky Medical Group, Inc.'s and Smith & Nephew, Inc.'s reply in support of their motion to stay, with exhibit, filed by Blue Sky on May 21, 2008. SA00102–003.

*Medela* v. *KCI,* Case No. 7cv449, Plaintiff's memorandum in support of continuing to stay litigation pending reexamination of U.S. Patent No. 7,216,651 and conclusion of related appeal, filed by Medela on May 9, 2008. SA449–007.

*Medela* v. *KCI,* Case No. 7cv449, Plaintiffs KCI's and Wake Forest's brief in opposition to Medela's motion to stay with Proposed order and exhibits, filed by KCI on May 16, 2008. SA449–008.

*Medela* v. *KCI,* Case No. 7cv449, Plaintiff's reply to KCI's and Wake Forest's Brief in opposition to continue to stay litigation pending reexamination of U.S. Patent No. 7,216,651 and conclusion of related appeal, with Proposed order and exhibit, filed by Medela on May 21, 2008. SA449–009.

*Blue Sky* v. *KCI,* Case No. 7cv454, Plaintiffs Blue Sky Medical Group, Inc.'s and Smith & Nephew, Inc.'s motion to stay, Proposed order, and exhibits, filed by Blue Sky on May 9, 2008. SA454–008.

*Blue Sky* v. *KCI,* Case No. 7cv454, Plaintiffs KCI's and Wake Forest's brief in opposition to defendants' motion to stay, with Proposed order and exhibits, filed by KCI on May 16, 2008. SA454–009.

*Blue Sky* v. *KCI,* Case No. 7cv454, Plaintiffs Blue Sky Medical Group, Inc.'s and Smith & Nephew, Inc.'s reply in support of their motion to stay, filed by Blue Sky on May 21, 2008. SA454–010.

*KCI et al.* v. *Blue Sky Medical Group et al.,* Case No. 2007–1340, –1341, –1342, Corrected reply brief of appellants, Medela AG and Medela, Inc., filed by Medela on May 21, 2008. CAFC1340–005.

*WFU* v. *ITI,* 1:08–cv–32. Answer to complaint with jury demand, filed by ITI on Mar. 4, 2008. MDNC32–002.

*WFU* v. *ITI,* 1:08–cv–32, Defendant ITI's motion to transfer venue, Proposed order, and Brief in support of defendant ITI's motion to transfer venue, or in the alternative, motion to stay, filed by ITI on Mar. 12, 2008. MDNC32–003.

*WFU* v. *ITI,* 1:08–cv–32, Plaintiffs' brief in opposition to defendant's motion to transfer venue, or in the alternative, motion to stay, filed by WFU on Apr. 18, 2008. MDNC32–004.

*WFU* v. *ITI,* 1:08–cv–32, Defendant ITI's reply brief in support of its motion to transfer venue, or in the alternative, motion to stay, with exhibits, filed by ITI on May 5, 2008. MDNC32–005.

*KCI* v. *BlueSky,* Trial Transcript for Orgill/Bridi/McGregor/Girolami/Taylor, dated Jul. 12, 2006. BS–116.

Request for Inter Partes Reexamination of U.S. Patent No. 7,216,651, requested May 30, 2008. IPRE–001.

Exhibits to Request for Inter Partes Reexamination of U.S. Patent No. 7,216,651, requested May 30, 2008. IPRE–002.

Bagautdinov, N.A., "Alternative method of external vacuum aspiration in the treatment of purulent soft tissue disease," Curr. Problems Contemporary Clin. Surg.: Interscholastic Collection, pp. 94–96, (6 sheets of English translation and certification dated May 30, 2008; four sheets of English translation, 6 sheets in Russian, and certification dated May 9, 2008; 1 sheet of English translation of alleged library index card, 1 sheet in Russian, and certification dated May 7, 2008); I.N. Ulianov Chuvash State University, Cheboksary, (1986). NPL–690.

Zivadinovic, G., et al., "Vacuum therapy in the treatment of peripheral blood vessels," Conference Papers of the 5th Timok Medical Days, Majdanpek, No. 3–4, pp. 161–164, (5 sheets English translation; 5 sheets in Serbian, certification dated May 9, 2008) (1986). NPL–691.

Johnson, F.E., "An improved technique for skin graft placement using a suction drain", Surg. Gynecol. Obstet., 159 (6):584–585 (Dec. 1984). NPL–226__.

Safronov, A.A., Dissertation Abstract, "Vacuum therapy of trophic ulcers of the lower leg with simultaneous autoplasty of the skin," (Central Scientific Research Institute of Traumotology and Orthopedics, Moscow, U.S.S.R.) (23 sheets English translation; 23 sheets in Russian; certification dated May 8, 2008; alleged index card(English translation; 1 sheet Russian; certification dated May 14, 2008), (1967), NPL–692.

Tribble, D.E., "An Improved sump drain–irrigation device of simple construction," Arch. Surg., 105:511–513, (Sep. 1972). NPL–693.

Tennant, C.E., "The use of hyperemia in the postoperative treatment of lesions of the extremities and thorax," Jour. A.M.A., 64(19):1548–1549, (May 8, 1915). NPL–694.

Orgill, D.P., et al., "Microdeformational wound therapy—a new era in wound healing," Business Briefing: Global Surgery—Future Directions, pp. 22, 24–25 (2005). NPL–695.

"V.A.C.® Therapy Clinical Guidelines: A reference source for clinicians," KCI, The Clinical Advantage® (Jul. 2007). NPL–696.

Request for Ex Parte Reexamination of U.S. Patent No. 5,636,643, requested Jun. 3, 2008. EPRE–003.

Exhibits to Request for Inter Partes Reexamination of U.S. Patent No. 5,636,643, requested Jun. 3, 2008. EPRE–002.

Westaby, S., et al., "A wound irrigation device," Lancet, pp. 503–504, (Sep. 2, 1978). NPL–701.

N.A. Bagautdinov, "Variant of External Vacuum Aspiration in the Treatment of Purulent Diseases of Soft Tissue," in Current Problems of Modern Clinical Surgery: Interdepartmental Collection, edited by V. Ye. Volkov et al. (Chuvashia State University, Cheboksary, U.S.S.R. 1986) pp. 94–96.

G. Živadinović, V. Dukić, 2. Maksimović, D. Radak, and P. Peška, "Vacuum Therapy in the Treatment of Peripheral Blood Vessels," *Timok Medical Journal* 11 (1986) 161–164.

F.E. Johnson, "An Improved Technique for Skin Graft Placement Using a Suction Drain," *Surgery, Gynecology, and Obstetrics* 159 (1984) 584–585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

C.E. Tennant, "The Use of Hyperemia in the Postoperative Treatment of Lesions of the Extremities and Thorax," *Journal of the American Medical Association* 64 (1915) 1548–1549.

Selections from W. Meyer and V. Schmieden, *Bier's Hyperemic Treatment in Surgery, Medicine, and the Specialties: A Manual of Its Practical Application* (W.B. Saunders Co., Philadelphia, PA 1909) pp. 17–25, 44–64, 90–96, 167–170, and 210–211.

S. Westaby and W.G. Everett, "A Wound Irrigation Device," *The Lancet* 312 (1978) 503–504.

D.E. Tribble, "An Improved Sump Drain–Irrigation Device of Simple Construction," *Archives of Surgery* 105 (1972) 511–513.

Declaration of Dr. Ian L. Gordon, M.D., Ph.D.

Declaration of Dr. Kenneth R. Diller, Sc.D.

U.S. Appl. No. 07/792,001, Amendment and Reply under 37 C.F.R. § 1.111, mailed Apr. 29, 1996.

In re U.S. Pat. No. 5,636,643, Control No. 90/008,697, Reply and Request for Reconsideration under 37 C.F.R. § 1.111, filed Apr. 28, 2008, in the U.S. Patent and Trademark Office.

*Kinetic Concepts, Inc.* v. *BlueSky Med. Corp.,* No. 5:03–CV–00832, Plaintiffs' Original Complaint (W.D. Tex. Aug. 28, 2003).

*Kinetic Concepts, Inc.* v. *BlueSky Med. Group, Inc.,* Nos. 2007–1340, –1341, –1342, Brief of Appellants, Medela AG and Medela, Inc. (Fed. Cir. May 23, 2007).

*Kinetic Concepts, Inc., v. BlueSky Med. Group, Inc.,* Nos. 2007–1340, –1341, –1342, Brief of Kinetic Concepts, Inc., KCI Licensing, Inc., KCI USA, Inc., and Wake Forest University Health Sciences (Fed. Cir. Mar. 3, 2008).

*Kinetic Concepts, Inc.* v. *BlueSky Med. Group, Inc.,* Nos. 2007–1340, –1341, –1342, Reply Brief of Appellants, Medela AG and Medela, Inc. (Fed. Cir. May 16, 2008).

Selections from *Kinetic Concepts, Inc.* v. *BlueSky Med. Corp.,* No. SA–03–CA–0832, in the U.S. District Court for the Western District of Texas.

D.P. Orgill, L.R. Bayer, J. Neuwalder, and R.C. Felter, "Microdeformational Wound Therapy—A New Era in Wound Healing," in *Global Surgery: Future Directions in Surgery* (Touch Briefings, London, U.K. 2005) pp. 22–25.

M.J. Morykwas, B.J. Faler, D.J. Pearce, and L.C. Argenta, "Effects of Varying Levels of Subatmospheric Pressure on the Rate of Granulation Tissue Formation in Experimental Wounds in Swine," *Annals of Plastic Surgery* 47 (2001) 457–551.

*V.A.C. Therapy Clinical Guidelines: A Reference Source for Clinicians* (KCI Licensing Inc., San Antonio, TX 2007).

R. Fujimori, M. Hiramoto, and S. Ofuji, "Sponge Fixation Method for Treatment of Early Scars," *Plastic & Reconstructive Surgery* 47 (1968) 322–327.

*KCI et al.* v. *Blue Sky Medical Group et al.,* Case No. 2007–1340, –1341, –1342, Reply brief of Plaintiffs–Cross Appellants, filed by KCI and Wake Forest on Jul. 2, 2008. CAFC1340–006.

Zivadinovic, G., et al., "Vacuum therapy in the treatment of peripheral blood vessels," Timok Medical Journal, Abstract book of the 5th Timok Medical Days, Majdanpek, 6 sheets of English translation, (1986). NPL–703.

Safronov, A.A., "Vacuum therapy for trophic ulcers of the tibia with concurrent skin autoplasty," Dissertation abstract, additional abstract, Moscow, 20 sheets of English translation, (1967). NPL–704.

Safronov, A.A., Abstract of Invention No. 240188, "Device for wound or ulcer treatment," (2 sheets English translation and 2 sheets in Russian) (1969). NPL–705.

Request for Ex Parte Reexamination of U.S. Patent No. 5,645,081, requested Jun. 3, 2008. EPRE–001.

Exhibits to Request for Ex Parte Reexamination of U.S. Patent No. 5,645,081, requested Jun. 3, 2008. EPRE–002.

Bagautdinov, N.A., "Variant of external vacuum aspiration in the treatment of purulent diseases of soft tissues," Current Problems in Modern Clinical Surgery, Interdepartmental Collection, Cheboksary, (4 pages of English translation, 6 sheets in Russian, certification dated May 22, 2008, English translation of index card, 1 sheet Russian, certification dated May 7, 2008) (1986). NPL–697.

Chardak, W.M., et al., "Experimental studies on synthetic substitutes for skin and their use in the treatment of burns," Ann. Surg., 155(1):127–139, (Jan. 1962). NPL–698.

Fujimori, R., et al., "Sponge fixation method for treatment of early scars," Plast. & Reconst. Surg., 42(4):322–326, (Oct. 1968). NPL–699.

Kirk–Othmer, Encyclopedia of Chemical Technology, 2nd completely revised edition, vol. 14, pp. 227, John Wiley & Sons, Inc., (1967). NPL–700.

Meyer, W., et al., excerpts from "Bier's Hyperemic Treatment", W.B. Saunders and Co., (47 sheets) (1908). NPL–702.

W.M. Chardak, D.A. Brueske, A.P. Santomaurio, and G. Fazekas, "Experimental Studies on Synthetic Substitutes for Skin and Their Use in the Treatment of Burns," *Annals of Surgery* 155 (1962) 127–139.

In re U.S. Pat. No. 5,645,081, Control No. 90/008,692, Reply and Request for Reconsideration under 37 C.F.R. § 1.111, filed Apr. 28, 2008, in the U.S. Patent and Trademark Office.

*Kinetic Concepts, Inc.* v. *BlueSky Med. Corp.,* No. SA–03–CA–0832, Plaintiffs' Fourth Amended Complaint (W.D. Tex. Jun. 30, 2005)("Amended Complaint").

*Kinetic Concepts, Inc.* v. *BlueSky Med. Group, Inc.,* Nos. 2007–1340, –1341, –1342, Brief of Kinetic Concepts, Inc., KCI Licensing, Inc., KCI USA, Inc., and Wake Forest University Health Sciences (Fed. Cir. Mar. 3, 2008).

*Kirk–Othmer Encyclopedia of Chemical Technology,* edited by A. Standen (John Wiley & Sons, Inc., $2^{nd}$ ed., vol. 14 1967). p. 227.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Reply Brief to Claim Construction dated Apr. 18, 2005 BS–147.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Responsive Claim Construction Brief dated Mar. 28, 2005 BS–148.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela AG and Medela, Inc.'s Response on Claim Construction dated Mar. 28, 2005 BS–154.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Bluesky Medical Group Incorporated's Opposition Markman Brief Regarding U.S. Patent Nos. 4,969,880 and 5,636,643 BS–155.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Markman Presentation of May 12, 2005 BS–156.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Blue Sky Medical Corp.'s Markman Presentation dated May 12, 2005 BS–157.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela Markman Presentation dated May 12, 2005 BS158.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Letter Brief from BlueSky Medical dated May 31, 2005 BS–159.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs First Letter Brief from Markman hearing dated May 26, 2005 BS–160.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Second Letter Brief from Markman hearing dated May 31, 2005 BS–161.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Transcription of Videotaped Deposition of Louis C. Argenta, M.D., Apr. 29, 2005 BS–68.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Transcription of Videotaped Deposition of Michael Allan Batalia, Ph.D., Jan. 12, 2005 BS–69.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Transcription of Videotaped Deposition of Michael John Morykwas, Ph.D., Jan. 13, 2005 BS–70.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendants Medela AG and Medela Inc.'s Motion for Leave to Amend Designation of Expert Witnesses dated May 18, 2005 BS–162.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Answer to Defendant Bluesky Medical Group Incorporate's Crossclaim dated Jun. 1, 2005 BS–163.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Answer to Defendant Richard Weston's Counterclaim dated Jun. 1, 2005 BS–164.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Answer to Defendant Medela Inc.'s Amended Counterclaims dated Jun. 1, 2005 BS–165.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Answer to Defendant Medela AG's Amended Counterclaims dated Jun. 1, 2005 BS–166.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Objections and Answers to Medela's Subpoena in a Civil Case for Production of Documents and Deposition on Written Questions to Wake Forest University Baptist Medical Center dated Jun. 1, 2005 BS–167.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela, Inc. and Medela AG's Reply in Support of Motion for Leave to File Amended Answers to Third Amended Complaint, Additional Defenses, Second Amended Counterclaims and Jury Demands dated Jun. 1, 2005 BS–168.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Opposition to Medela AG and Medela, Inc.'s Motion for Leave to Amend Designation of Expert Witnesses and Request for Hearing dated Jun. 1, 2005 BS–169.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Objections and Answers to Medela, Inc.'s Subpoena in a Civil Case and Deposition on Written Questions to Dr. Joseph Molnar and Dr. Lawrence Webb dated Feb. 24, 2005 BS–170.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Order Adopting Stipulations of Parties Regarding Claim Term Construction dated May 12, 2005 BS–171.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Order Construing Patent '643 Claim Terms dated Jun. 28, 2005 BS–172.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Fourth Amended Complaint dated Jun. 30, 2005 BS–173.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Shelly Taylor dated Nov. 23, 2004 BS–71.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Michael Miller, D.O. dated Mar. 8, 2005 BS–72.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela AG's First Supplemental Response to Plaintiff's First Interrogatories to Defendant Medela AG dated Jul. 13, 2005 BS–179.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela Inc.'s First Supplemental Response to Plaintiff's First Interrogatories to Defendant Medela, Inc. dated Aug. 16, 2005 BS–180.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Matthew C. Dairman, Feb. 3, 2005 BS–73.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Ronald C. Hamaker, May 26, 2005 BS–74.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Mordechai Twena, Jan. 25, 2005 BS–75.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Preliminary Proposed Constructions of Newly Asserted Claims from the '643 and '081 Patents dated Sep. 12, 2005 BS–181.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Opposition to Defendant Bluesky Medical Group Incorporated's and Richard Weston's Motion for Summary Judgment on the '643 Patent, including Declaration of Wilson C. Hayes in Support Thereof including Exhibits BS–182.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiff's Opposition to Defendant Bluesky Medical Group Incorporated's and Richard Weston's Motion for Summary Judgment on the '880 Patent, including Declaration of Wilson C. Hayes in Support Thereof including Exhibits BS–183.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Answer to Fourth Amended Complaint, Additional Defenses, Third Amended Counterclaims and Jury Demand of Defendant Medela AG, Jul. 18, 2005 BS–184.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Answer to Fourth Amended Complaint, Additional Defenses, Third Amended Counterclaims and Jury Demand of Defendant Medela, Inc., Jul. 18, 2005 BS–185.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of Mark Chariker dated May 6, 2006 BS–76.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition transcript with Exhibits of David S. Zamierowski dated Feb. 15, 2005 BS–77.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Harriet W. Hopf dated May 10, 2005, along with Supplemental Expert Report with Exhibits dated May 25, 2005 BS–17.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Susan Mendez–Eastman dated Jan. 7, 2004 BS–18.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Jose Diaz dated Nov. 26, 2004 BS–19.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Jeffrey Niezgoda dated Nov. 23, 2004 BS–20.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Kathleen Satterfield dated Nov. 29, 2004 BS–21.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Exhibits 281–288 of previously submitted Transcription of Deposition of Michael John Morykwas, Ph.D., dated Jan. 13, 2005 BS–78.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report with Exhibits of Valery Gilevich (Dec. 14, 2004). BS–49.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela, Inc., and Medela AG's Motion for Entry of Amended Protective Order with Exhibits dated Oct. 7, 2005. BS–186.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Videotaped Deposition transcript of Carr Lane Quackenbush dated Oct. 6, 2004. BS–79.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Medela AG's Answers to Plaintiffs' Second Interrogatories dated Oct. 7, 2005. BS–187.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela AG's Affidavit of Mitchell D. Lukin Pursuant to Local Rule CV–33(a) dated Oct. 7, 2005. BS–188.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Medela AG's Response to Plaintiffs' Second Request for Production of Documents dated Oct. 7, 2005. BS–189.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Medela AG's Response to Plaintiffs' Third Request for Production of Documents dated Oct. 7, 2005. BS–190.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Medela, Inc.'s Response to Plaintiffs' Second Request for Production of Documents dated Oct. 7, 2005. BS–191.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Plaintiffs' Opening Brief on Claim Construction of Disputed Claim Terms From the '643 and '081 Patents with Exhibits dated Oct. 6, 2005. BS–192.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Medela, Inc.'s Second Set of Interrogatories To Wake Forest University Health Sciences dated Oct. 7, 2005. BS–193.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Medela, Inc.'s Eighth Set of Requests For Production To Plaintiffs Kinetic Concepts, Inc., KCI Licensing, Inc., KCI USA, Inc., and Wake Forest University Health Sciences dated Oct. 7, 2005. BS–194.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Order Grating Joint Motion of Extend Deadlines dated Sep. 30, 2005. BS–195.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., BlueSky Medical Group Inc.'s Additional Supplemental Discovery Production with Bates Labels and Cover Letter dated Sep. 30, 2005. BS–224.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Joint Motion for Entry of Order Adopting the Parties' Stipulated Claim Term Constructions dated Oct. 6, 2005. BS–196.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Order Adopting the Parties' Stipulated Claim Term Constructions. BS–197.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Promotional Slide Presentation BlueSky Medical Negative Pressure Wound Care with Versatile 1 Presentation Presented by Penny Campbell and Shelly Burdette–Taylor 27 pages (dated Oct. 14, 2005). NPL–067.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Defendant Bluesky Medical Group Inc. and Richard Weston's Reply to Plaintiffs Opposition to Defendant Bluesky Medical Group Inc. and Richard Weston's Motions for Partial Summary Judgment dated Sep. 28. 2005. BS–198.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Order Granting Plaintiffs' Unopposed Motion to Supplement The Record for its repsonse to Bluesky's Motion for Partial Summary Judgment dated Oct. 13, 2005. BS–200.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Order Granting Medela, Inc. And Medela AG's Unopposed Motion to Extend Deadlines for Markman Briefing dated Oct. 13, 2005. BS–201.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Plaintiffs' Unopposed Motion to Supplement the Record in Support of Their Response to Bluesky's Motion For Partial Summary Judgment on Counts Twelve, Thirteen, and Fifteen dated Oct. 10, 2005. BS–202.

Wu, Lisa C., et al., "Vacuum–Assisted Closure for the Treatment of Sternal Wounds: The Bridge Between Debridement and Definitive Closure", printout from www.plasticsurgery.org., 3 pages (printout dated Apr. 20, 2005). NPL–448.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Joint Claim Construction and Prehearing Statement dated Sep. 16, 2005. BS–204.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Defendants' Opening Brief Regarding Claim Construction for The '081 Patent and Certain Claims of the '643 Patent dated Oct. 5, 2005. BS–203.

Bertone, A., "Management of Exuberant Granulation Tissue", Wound Management, pp. 550–562 (Dec. 1989). NPL–043.

Taber's Cyclopedic Medical Dictionary, Edition 18, pp. 937, 942 and 1375. NPL–394.

Harris, Ann, et al., "Hypergranulation Tissue: a Nontraumatic Method of Management", Ostomy/Would Management, vol. 40, No. 5, Jun. 1994. NPL–193.

Opposition EP to 0620720, Patentee Response to Grounds of Appeal Filed by Opponent, Paul Hartmann AG, with Exhibits dated Apr. 25, 2005. EPOPWH1–16.

Opposition EP to 0620720, Opponents Response to Grounds of Appeal Filed by Patentee, dated Apr. 25, 2005. EPOPWH1–17.

Opposition EP to 0620720, Patentees' Grounds of Appeal, dated Sep. 29, 2004. EPOPWH1–18.

Opposition EP to 0620720, Third–Party Communication dated Feb. 15, 2005 (R.G.D. Jenkins & Co.) EPOPWH1–19.

Opposition EP to 0620720, Interlocutory Decision dated May 19, 2004. EPOPWH1–13.

Opposition EP to 0620720, Communication of Patentee dated Nov. 25, 2003. EPOPWH1–12.

Opposition EP to 0620720, Third–Party Communication dated Nov. 12, 2003 (R.G.C. Jenkins & Co.) EPOPWH1–11.

Opposition EP to 0620720, Third–Party Communication dated Aug. 14, 2003. (R.G.C. Jenkins & Co.) EPOPWH1–09.

Opposition EP to 0620720, Communication of Patentee dated Nov. 9, 2003. EPOPWH1–10.

Webster's New Universal Unabridged Dictionary Deluxe Second Edition, p. 631. NPL–431.

Opposition EP to 0620720, Communication of Opponent Mondomed dated Aug. 8, 2001. (Margot Muller–Gerbes) EPOPWH1–07.

Opposition EP to 0620720, Communication of Opponent Mondomed dated May 3, 2001. (Margot Muller–Gerbes) EPOPWH1–06.

Opposition EP to 0620720, Communication of Patentee dated Sep. 22, 2000. EPOPWH1–05.

Kinetic Concepts, Inc., et al., v. Bluesky Medical Corporation, et al., Civil Action No. SA–03–CA–0832–RF, U.S. District Court, W. Dist. of Texas San Antonio Div., Defendant Bluesky Medical Group Incorporated's and Richard Weston's Motion for Summary Judgment on the '643 Patent with Exhibits dated Aug. 10, 2005. BS–205.

Kinetic Concepts, Inc., et al., v. Bluesky Medical Corporation, et al., Civil Action No. SA–03–CA–0832–RF, U.S. District Court, W. Dist. of Texas San Antonio Div., Defendant Bluesky Medical Group Incorporated's and Richard Weston's Motion for Summary Judgment on the '880 Patent with Exhibits dated Aug. 10, 2005 BS–206.

Meyer, W., et al., Bier's Hyperemic Treatment, "Hyperemia by suction apparatus", Hyperemia as a Therapeutic Agent, Chicago, IL, Roberts Publishing; 1908: 74–85. NPL–216.

Kinetic Concepts, Inc., et al., v. Bluesky Medical Corporation, et al., Civil Action No. SA–03–CA–0832–RF, U.S. District Court, W. Dist. of Texas San Antonio Div., Plaintiffs' Surreply Further Opposing Defendant Bluesky Medical Group Incorporated's and Richard Weston's Motions for Summary Judgement on the '643 and '880 Patents with Exhibits dated Oct. 14, 2005. BS–133.

Chariker–Jeter Technique Tutorial by Penny E. Campbell, Wound Care Solutions, 1 page tutorial chart. NPL–075.

Bluesky Medical, Negative Pressure Wound Therapy, Product Catalog Fall 2005, "Finally a choice . . . " 8 pages NPL–053.

Promotional Slide Presentation by Penny Campbell 27 pages (Oct. 14, 2005). NPL–067.

KCI v. BlueSky, Transcript of Deposition of Jeffrey A. Niezgoda, M.D., with Exhibits, dated May 1, 2006. parts 1–24 of 50. BS–94.

KCI v. BlueSky, Transcript of Deposition of Jeffrey A. Niezgoda, M.D., with Exhibits, dated May 1, 2006. parts 25–50 of 50. BS–94.

Spahn, J.G., "Soft tissue challenges in the head and neck region,"Clinical Seminar Handout, EHOB, (46 pages) NPL–621.

Stewart, A., et al., "Cleaning v. healing," Community Outlook, pp. 22, 24 & 26 (Aug. 14, 1985). NPL–601.

Svedman, "Irrigation Treatment of Leg Ulcers", The Lancet, Sep. 3, 1983, pp. 532–534. NPL–679.

Svedman, P., et al., "Staphylococcal wound infection in the pig: Part I. Course," Ann. Plast. Surg., 23(3):212–218, (Sep. 1989). NPL–684.

Trammell, T.R., et al., "Close–wound drainage systems: the Solcotrans Plus versus the Stryker–CBC ConstaVAC", Orthopaedic Review, 20(6):536–542 (Jun. 1991). NPL–608.

Woodley, D.T., et al., "A double–blind comparison of adhesive bandages with the use of uniform suction blister wounds", Arch. Dermatol., 128(10)):1354, 1357 (Oct. 1992). NPL–609.

Zelko, J.R., et al., "Primary closure of the contaminated wound; closed suction wound catheter", Am. J. Surgery, 142:704–706, (Dec. 1981). NPL–604.

KCI v. BlueSky, Amended answer to third amended complaint, additional defenses, second amended counterclaims and jury demand of Medela, Inc. dated Jul. 12, 2005. BS–223.

KCI v. BlueSky, Order denying defendant BlueSky's motion for new trial, dated Apr. 4, 2007. BS–238.

KCI v. BlueSky, Order denying plaintiff's motion for new trial or judgment as a matter of law, dated Apr. 4, 2007. BS–239.

KCI v. BlueSky, Order denying defendant Medela's renewed motion for judgment as a matter or law, or, alternatively, a new trial on patent invalidity and defendant BlueSky's motion for new trial, dated Apr. 4, 2007. BS–240.

KCI v. BlueSky, Order denying defendant Medela's motion for new trial on unenforceability and defendant BlueSky's motion for new trial, dated Apr. 4, 2007. BS–241.

KCI v. BlueSky, Order denying plaintiff's rule 60(b) motion for new trial, dated Apr. 4, 2007. BS–242.

KCI v. BlueSky, Final Judgment, dated Apr. 4, 2007. BS–243.

KCI v. BlueSky, Plaintiff's Argument, Markman Hearing, Nov. 14, 2005. BS–246.

U.S. Appl. No. 10/227,161—Official action P02977US0–OA–01 (Feb. 9, 2004).

U.S. Appl. No. 10/227,161—Applicants' response P02977US0–OA–02 (Jun. 8, 2004).

U.S. Appl. No. 10/227,161—Official action P02977US0–OA–03 (Sep. 20, 2004).

U.S. Appl. No. 10/227,161—Applicants' response P02977US0–OA–04 (Mar. 17, 2005).

U.S. Appl. No. 10/227,161—Official action P02977US0–OA–05 (Jun. 7, 2005).

U.S. Appl. No. 10/227,161—Applicants' response P02977US0–OA–06 (Sep. 28, 2005).

U.S. Appl. No. 10/227,161—Official action P02977US0–OA–07 (Dec. 5, 2005).

U.S. Appl. No. 10/227,161—Applicants' response P02977US0–OA–08 (May 2, 2006).

U.S. Appl. No. 10/227,161—Final Office action P02977US0–OA–09 (Aug. 2, 2006).

U.S. Appl. No. 10/227,161—Official action P02977US0–OA–10 (Apr. 13, 2007).

U.S. Appl. No. 10/647,068—Official action P02977US1–OA–01 (Sep. 20, 2004).

U.S. Appl. No. 10/647,068—Applicants' response P02977US1–OA–02 (Mar. 17, 2005).

U.S. Appl. No. 10/647,068—Official action P02977US1–OA–03 (Jun. 7, 2005).

U.S. Appl. No. 10/647,068—Applicants' response P02977US1–OA–04 (Sep. 28, 2005).

U.S. Appl. No. 10/647,068—Official action P02977US1–OA–05 (Dec. 21, 2005).

U.S. Appl. No. 10/647,068—Applicants' response P02977US1–OA–06 (May 2, 2006).

U.S. Appl. No. 10/647,068—Final official action P02977US1–OA–07 (Aug. 11, 2006).

US/647,068—Official action P02977US1–OA–08 (Apr. 13, 2007).

U.S. Appl. No. 10/161,076—Official action P02915US0–OA–01 (Dec. 3, 2003).

U.S. Appl. No. 10/161,076—Applicants' response P02915US0–OA–02 (Jun. 2, 2004).

U.S. Appl. No. 10/161,076—Final official action P0215US0–OA–03 (Sep. 13, 2004).

U.S. Appl. No. 10/161,076—Final official action P02915US0–OA–04 (Dec. 15, 2004).

U.S. Appl. No. 10/161,076—Applicants' response P02915US0–OA–05 (Jun. 15, 2005).

U.S. Appl. No. 10/161,076—Official action P02915US0–OA–06 (Sep. 7, 2005).
U.S. Appl. No. 10/161,076—Applicants' response P02915US0–OA–07 (Mar. 7, 2006).
U.S. Appl. No. 10/161,076—Final official action P02915US0–OA–08 (May 24, 2006).
U.S. Appl. No. 10/161,076—Applicants' response P02915US0–OA–09 (Nov. 21, 2006).
U.S. Appl. No. 10/161,076—Official action P02915US0–OA–10 (Sep. 14, 2007).
U.S. Appl. No. 10/227,161—Applicants' response P02977US0–OA–11 (Oct. 15, 2007).
U.S. Appl. No. 10/647,068—Applicants' response P02977US1–OA–09 (Oct. 15, 2007).
Davydov, Y.A., et al., "Bacteriological and cytological assessment of vacuum therapy of purulent wounds,"Vestnik Khirurgii imeni I.I. Grekova, (7 sheets of translation, pp. 48–52 of Russian text and English abstract on p. 52); 141(10):48–52 (Oct. 1988). DV4.
Davydov, Y.A., et al., "Vacuum therapy in the treatment of purulent lactation mastitis", Vestnik Khirurgii imeni I.I. Grekova, (8 sheets of English translation, pp. 66–70 of Russian text, and English abstract on p. 70); 137(11):66–70, (Nov. 1986). DV7.
Davydov, Y.A., et al., "Vacuum therapy in the treatment of acute purulent diseases of soft tissues and purulent wounds", Vestn. Khir. Im. I.I. Grek., (4 sheets of Translation, 4 sheets of Russian text and English abstract on p. 46); 141(9):43–46 (Sep. 1988). DV9.
Opposition to EP 0,620,720—Summons to attend oral proceedings pursuant to Rule 71(1) EPC, Annex to communication, (9 sheets) both dated (Feb. 13, 2002) and Communication from Opponent Mondomed N.V. (2 sheets) (dated Feb. 15, 2002). EPOPWH1–21.
Opposition to EP 0,620,720—Minutes of the Oral Proceedings, Documents for the Maintenance of the Patent as Amended, Annex to the Communication (30 sheets) (dated Dec. 30, 2003). EPOPWH1–22.
Opposition to EP 0,620–720—Communication of Notices of Opposition (Rule 57(1) EPC) dated (Feb. 8, 1999) (1 sheet), Notice of Opposition by Mondomed N.V., (4 sheets) and 8 sheets of Facts and Arguments presented in support of opposition (dated Jul. 1, 1998), EPOPWH1–23.
Opposition to EP 0,620,720—Notice of Opposition by Paul Hartmann A.G., (6 sheets) (dated Dec. 16, 1998). EPOPWH1–24.
Opposition to EP Patent 0,620,720—New European Patent Specification EP 0620720B2 (published Nov. 2, 2008). EPOPWH1–25.
Opposition to EP 0,620,720—Letter to European Patent Office regarding Paul Hartmann AG, (7 sheets) (dated Mar. 6, 2006). EPOPWH1–27.
"Analysis of Features of Claim 1 of EP 0 620 720 B2" (EP equivalent of US 5645081) labeled as "Anlage NK5" in German with English translation. DENA–WH1–004.
"Analysis of Features of Claim 1 of EP 0 688 189 B2," (EP equivalent of US 5636643) labeled "Anlage NK7" in German with English translation. DENA–WH2–003.
"Coldex," labeled as "Anlage NK12" in German with English translation. DENA–WH1–007.
"Re. The Patentability of Claim 1 of EP 0 688 189 B2 (Patent II)" (EP equivalent of US 5636643) labeled as "Anlage NK12" in German with English translation. DENA–WH2–004.

"Re. Patentability of Claim 1 of EP 0 620 720 B2 (Patent I)—Novelty," (EP equivalent of US 5645081) labeld "Anlage NK14," in German with English translation. DENA–WH1–003.
EP 0 620 720 (DE 692 24 847) Nullity Action filed at the German Federal Patent Court to nullify EP 0 620 720 (DE 692 24 847) (EP equivalent of US 5645081) and English translation, dated Jun. 28, 2007. DENA–WH1–001.
EP 0 620 720 (DE 692 24 847) Wake Forest University's Formal Response to the Jun. 28, 2007 Complaint and English translation, dated Jul. 20, 2007. DENA–WH1–002.
EP 0 688 189 (DE 694 25 881) Nullity Action filed at the German Federal Patent Court to nullify EP 0 688 189 (DE 694 25 881) (EP equivalent of US 5636643) with English translation, dated Jun. 28, 2007. DENA–WH2–001.
EP 0 688 189 (DE 694 25 881) Wake Forest University's Formal Response to the Jun. 28, 2007 Complaint and English translation, dated Jul. 20, 2007. DENA–WH2–002.
Fleischmann, W., et al., "Combination osteosynthesis in the treatment of pylon fractures with soft tissue damage," labeled "Anlage NK10," pp. 178–181 and showing "6. German–Austrian–Swiss Trauma Conference in Vienna May 21–25, 1991," published in "Der Unfallchirurg" [The Traumatologist] in 1993, in German with English translation. DENA–WH1–006.
Fleischmann, W., et al., "Combination osteosynthesis in treating pilon fractures involving soft tissues injuries," in "Translation of an excerpt from the brochure regarding the Sixth German–Austrian–Swiss Accident Congress" allegedly dated 1991, in German with English translation. DENA–WH1–009.
ISO–10079–1, "International Standard," "Medical suction equipment—Part 1: electrically powered suction equipment—Safety requirements," dated May 15, 1991. DENA–WH2–005.
Juchli, L., "Krankenpflege [Nursing] Practice and Theory of Promoting Health and Patient Care," George Thieme Verlag Stuttgart, labeled as "Anlage 6.1" 1991 (allegedly dated Feb. 1991), and email dated May 30, 2007 labeled as "Anlage 6.2," both in German with English translations. DENA–WH1–005.
Turner, T.D., et al., eds., Excerpts from "Advances in wound management," including "Recent advances in wound management products" by T.D. Turner and "The role of foam dressings in wound management" by S. Thomas, Proceedings of a symposium held at the Welsh School of Pharmacy, University of Wales Institute of Science and Technology, Cardiff, Mar. 20–21, 1985, labeled as "Anlage NK13," 1986. DENA–WH1–008.
Aeros, "Moblvac,""introducing the 'off the wall' vacuum system,"Aeros Instruments, Life Support Nursing, 3(1):34–37, Barlin Publishing Ltd. (Jan.–Feb. 1980). NPL–007.
Addition to the "Users Manual Concerning Overflow Protection–Concerns all Egnell Pumps", dated Feb. 3, 1983, 1 page Swedish, [1 page English]. NPL–680.
Addition to the "Users Manual Concerning Overflow Protection–Concerns all Egnell Pumps", dated Feb. 3, 1983, 2 pages of English translation. NPL–683.
Article in Russian, pp. 84–85; NPL–619.
Austad, E.D., et al., "Tissue expansion: dividend or loan-?"Plast. Reconstr. Surg.,78(1):63–67 (Jul. 1986). NPL–023.

BlueSky Medical, 2 sheets of advertisement, "Introducing the Chariker–Jeter wound drainage kit" and "Introducing the Kremlin® wound drainage kit" NPL–620.

Campbell, P., "Arthrodesis of the ankle with modified distraction–compression and bone-grafting", J. Bone Joint Surg. Am., (1 sheet printout from PubMed); 72(4):552–556 (Apr. 1990). NPL–666.

Cattaneo, R., et al., "Treatment of septic or non–septic diaphyseal pseudoarthroses by Ilizarov's monofocal compression method", Rev. Chir. Orthop. Reparatrica Appar. Mot., (1 sheet printout from PubMed); 71(4):223–229 (1985). NPL–674.

De Bastiani, G., et al., "Dynamic axial fixation. A rational alternative for the external fixation of fractures", Int. Orthop., (1 sheet printout from PubMed); 10(2):95–99 (1986). NPL–672.

De Bastiani, G., et al., "Limb lengthening by callus distraction (callotasis)", J. Pediatr. Orthop., (1 sheet printout from PubMed); 7(2):129–134 (Mar./Apr. 1987). NPL–671.

Defranzo, A.J., et al., "The use of V.A.C. therapy for treatment of lower extremity wounds with exposed bone", 68th Annual Meeting of the American Society of Plastic and Reconstructive Surgeons, New Orleans, LA, pp. 37–38; 2 sheets of abstract (Oct. 24–27, 1999). WFU–42.

Egnell Minor, Instruction Book, First Edition, allegedly dated Feb. 1987, 21 pages Swedish, 3 pages English. NPL–681.

Egnell Minor, Instruction Book, First Edition allegedly dated Feb. 1987, 34 pages of English translation. NPL–682.

Feierabend, T.C., et al., "Injuries causing major loss of scalp", Plast. Reconstr. Surg., [Abstract only—1 pp. printout from PubMed], 76(2):189–194 (Aug. 1985). NPL–623.

Geronemus, R.G., et al., "The effect of two new dressings on epidermal wound healing", J. Dermatol. Surg. Oncol., 8(10):850–852 (Oct. 1982). NPL–606.

Goodship, A.E., et al., "Functional adaptation of bone to increased stress", J. Bone Joint Surg., 61–A(4):539–546 (Jun. 1979). NPL–644.

Goodship, A.E., et al., "Strain rate and timing of stimulation in mechanical modulation of fracture healing", Clin. Orthop. Rel. Res., (and 1 sheet printout from PubMed); (355S):S105–S115, (Oct. 1998). NPL–646.

Goodship, A.E., et al., "The influence of induced microenvironment upon the healing of experimental tibial fractures", J. Bone Joint Surg., 67–B(4):650–655 (Aug. 1985). NPL–645.

Kenwright, J., et al., "Controlled mechanical stimulation in the treatment of tibial fractures", Clin. Orthop. Rel. Res., (241):36–47 (Apr. 1989). NPL–648.

Lanyon, L.E., et al., "Bone deformation recorded in vivo from strain gauges attached to the human tibial shaft", Acta Orthop. Scand., 46:256–268 (1975). NPL–650.

Lascombes, P., et al., "Ilizarov's method. Histological and radiological aspects," J. Radiol., (1 sheet printout from PubMed); 72(1):11–16 (Jan. 1991). NPL–677.

Miller, S.H., et al., "An inexpensive wound suction device", Surg. Gyencol. Obstet., 141(5):768 (Nov. 1975). NPL–607.

Miller, S.J., "Surgical wound drainage system using silicone tubing", J. Am. Podiatry Assn., 71(6): pp. 287–296, (Jun. 1981). NPL–605.

Monticelli, G., et al., "Leg lengthening by closed metaphyseal corticotomy", Ital. J. Orthop. Traumatol., (1 sheet printout from PubMed); 9(2):139–150 (Jun. 1983). NPL –687.

Nelson, R.P., et al., "Use of negative pressure suction in urology", Urology, 4(5):574–576, (Nov. 1974). NPL–494.

Paley, D., "Current techniques of limb lengthening", J. Pediatr. Orthop., 8(1):73–92 (1988). NPL–653.

Sanden, G., et al., "Staphylococcal wound infection in the pig: Part II. Inoculation, quantifcation of bacteria, and reproducibility," Ann. Plast. Surg., 23(3):219–223, (Sep. 1989), NPL–685.

*KCI* v. *BlueSky*, Expert Report of Michael Baniak, with Exhibits, dated Jan. 7, 2005. BS–10.

*KCI* v. *BlueSky*, Expert Report of Mark Chariker, with Exhibits, dated Jan. 7, 2005. BS–23.

*KCI* v. *BlueSky*, Supplemental Expert Report of Mark Chariker, M.D., with Exhibits, dated Dec. 19, 2005. BS–24.

*KCI* v. *BlueSky*, Supplemental Expert Report of Harriet Hopf, with Exhibits, dated Nov. 18, 2005. BS–25.

*KCI* v. *BlueSky*, Amended Expert Report of Harriet W. Hopf, M.D. on New Claims, with Exhibits, dated Feb. 10, 2006. BS–26.

*KCI* v. *BlueSky*, Expert Report of Harriet W. Hopf, M.D. Responsive to Plaintiff's Asserted Claims for Relief, with Exhibits, dated Feb. 10, 2006. BS–27.

*KCI* v. *BlueSky*, Supplemental Expert Report of Harriet W. Hopf, M.D. with Exhibits, dated Jun. 23, 2006. BS–28.

*KCI* v. *BlueSky*, Report of Professor Thomas K. Hunt, M.D., pp. 1–14, with Exhibits, Jan. 13, 2005. BS–29.

*KCI* v. *BlueSky*, Report of Katherine F. Jeter, with Exhibits, dated Nov. 28, 2004. BS–11.

*KCI* v. *BlueSky*, Supplemental Expert Report of Michael O'Neil, dated Feb. 22, 2006. BS–31.

*KCI* v. *BlueSky*, Rebuttal Expert Report of Harriet W. Hopf, M.D. with Exhibits, dated Mar. 11, 2006. BS–32.

*KCI* v. *BlueSky*, Rebuttal Report to Plaintiffs' Rebuttal Expert Report by Michael O'Neil, dated Mar. 21, 2006. BS–33.

*KCI* v. *BlueSky*, Attachments to Expert Report of Michael A. O'Neil. BS–34.

*KCI* v. *BlueSky*, Expert Report of Vincent Pizziconi, with Exhibits, dated Dec. 31, 2005. BS–35.

*KCI* v. *BlueSky*, Amended Expert Report of Vincent B. Pizziconi, Ph.D., with Exhibits, dated Feb. 6, 2006. BS–36.

*KCI* v. *BlueSky*, Expert report of Vincent B. Pizziconi, Ph.D. responsive to plaintiff's asserted claims for relief, with exhibits, dated Feb. 14, 2006. BS–37.

*KCI* v. *BlueSky*: Amended expert report of Vincent B. Pizziconi, Ph.D. responsive to plaintiff's asserted claims for relief, with exhibits, dated Feb. 16, 2006. BS–38.

*KCI* v. *BlueSky*, Rebuttal Expert Report of Vincent B. Pizziconi, Ph.D., with Exhibits, dated Mar. 12, 2006. BS–39.

*KCI* v. *BlueSky*, Supplemental Expert Report of Vincent B. Pizziconi, Ph.D. with Exhbits, dated Jun. 23, 2006. BS–40.

*KCI* v. *BlueSky*, Supplemental expert report of Lydia Razran Stone, Ph.D., with exhibits, dated mar. 8, 2006. BS–41.

*KCI* v. *BlueSky*, Expert Report of Lydia Razran Stone, Ph.D., with Exhibits, dated Dec. 29, 2005. BS–42.

*KCI* v. *BlueSky*, Expert Report of Louis C. Argenta in Response to Report of Katherine Jeter, with Exhibits, dated Jan. 5, 2005. BS–43.

*KCI* v. *BlueSky*, Responsive Expert Report of Louis C. Argenta to Reports of Hopf, O'Neil, Pizziconi & Chariker, dated Feb. 27, 2006. BS–44.

*KCI* v. *BlueSky*, Responsive Expert Report of Louis C. Argenta to Supplemental Expert Report of O'Neil, dated Mar. 13, 2006. BS–45.

*KCI v. BlueSky*, Rebuttal Report of Louis C. Argenta in Response to James Spahn, Mark Chariker & Thomas Hunt. BS–46.

*KCI v. BlueSky*, Responsive Expert Report of Louis C. Argenta, M.D. to Expert Supplemental Reports of Hopf and Pizziconi, with Exhibits, dated Jul. 8, 2006. BS–47.

*KCI v. BlueSky*, Responsive Expert Report of Valery Gilevich, M.D. to Expert Report of Lydia Razran Stone, Ph.D. BS–48.

*KCI v. BlueSky*, Expert Report of Valery Gilevich, dated Dec. 14, 2004, with Exhibits, (Exhibit P–47). BS–49.

*KCI v. BlueSky*: Rebuttal expert report of John T. Goolkasian, dated Feb. 22, 2006. BS–50.

*KCI v. BlueSky*, Supplemental Rebuttal Expert Report of John T. Goolkasian, with Exhibits, dated Mar. 10, 2006. BS–51.

*KCI v. BlueSky*, Report of Wilson C. Hayes, PhD, with Exhibits, dated Nov. 29, 2004. BS–12.

*KCI v. BlueSky*, Expert Report of Wilson Hayes in Response to Reports of James Spahn and Mark Chariker, with Exhibits, dated Jan. 31, 2005. BS–53.

*KCI v. BlueSky*, Expert Report of Wilson Hayes in Response to Report of Katherine Jeter, with Exhibits, dated Jan. 7, 2005. BS–54.

*KCI v. BlueSky*, Supplemental Expert Report of Wilson C. Hayes, Ph.D. Concerning Infringement of Newly Asserted Claims of U.S. Patent Nos. 5,636,643 and 5,645,081, with Exhibits, dated Dec. 19, 2005. BS–55.

*KCI v. BlueSky*, Responsive Expert Report of Wilson Hayes in Response to Hopf, Chariker, Pizziconi, and O'Neil Regarding Patent Validity, with Exhibits, dated Feb. 27, 2006. BS–56.

*KCI v. BlueSky*, Rebuttal Expert Report of Wilson C. Hayes, Ph.D. in Response to the Reports of Harriet Hopf and Vincent Pizziconi Regarding Plaintiffs' Asserted Claims for Relief, with Exhibits, (Mar. 7, 2006). BS–57.

*KCI v. BlueSky*, Expert Report of Jeffery Niezgoda in Response to Katherine Jeter, dated Jan. 7, 2005. BS–58.

*KCI v. BlueSky*, Expert Report of Jeffery Niezgoda in Response to James Spahn, Thomas Hunt & Mark Chariker, dated Jan. 31, 2005. BS–59.

*KCI v. BlueSky*, Supplement to Expert Report of Jeffery Niezgoda, with Exhibits, dated Jan. 4, 2006. BS–60.

*KCI v. BlueSky*, Expert Report of Dennis P. Orgill, M.D., Ph.D., with Exhibits, dated Feb. 20, 2006. BS–61.

*KCI v. BlueSky*, Rebuttal Expert Report of Dennis Orgill to Amended Expert Reports of Harriet Hopf and Vincent Pizziconi, with Exhibits, dated Mar. 13, 2006. BS–62.

*KCI v. BlueSky*, Supplemental Expert Report of Dennis P. Orgill, M.D., Ph.D., with Exhibits, dated Jul. 6, 2006. BS–63.

Besst, J.A., et al., "Wound healing—intraoperative factors", Nurs. Clin. N. Am., 14(4):701–712 (Dec. 1979). NPL–044.

Bruno, P., "The nature of wound healing", Nursing Clinics of North America, 14(4):667–682 (Dec. 1979). NPL–064.

Cesany, P., "Suction in the treatment of torpid ulcerations", Rozhl. Chir., (English abstract on p. 409 (5 sheets) and 1 sheet printout from PubMed) 48(9):406–409 (Sep. 1969). NPL–072.

Cooper, D.M., "Optimizing wound healing: a practice within nursing's domain", Nurs. Clin. N. Am., pp. 25(1):165–180 (Mar. 1990). NPL–095.

Cooper, D., et al., "Postsurgical nursing intervention as an adjunct to wound healing", Nurs. Clin. N. Am., 14(4):713–726 (Dec. 1979). NPL–097.

Dillon, R.S., "Treatment of resistant venous stasis ulcers and dermatitis with the end–diastolic pneumatic compression boot", Angiology, 37(1):47–56 (Jan. 1986). NPL–118.

Fay, M.F., "Drainage systems: their role in wound healing", AORN J., 46(3):442–455 (Sep. 1987). NPL–149.

Fleischmann, W., et al., "Vacuum sealing as treatment of soft tissue injury in open fractures", Unfallchirurg Springer–Verlag, (English abstract on first page, and 8 pages of English translation); 96:488–92, (1993). NPL–157.

Gogia, P.P. "The biology of wound healing", Ostomy/Wound Manage., 38(9):12, 14–16, 18–20, 22 (Nov.–Dec. 1992). NPL–172.

Harkiss, K., "Leg ulcers cheaper in the long run", Community Outlook, pp. 19, 21, 22 (Aug. 14, 1985). NPL–190.

Stewart, A., et al., "Cleaning v. healing," Community Outlook, pp. 22, 24 & 26 (Aug. 14, 1985). NPL–601.

Harle, A., "Weak points of conventional drains", Z. Orthop., (with 9 sheets of English translation); 127:513–517 (1989). NPL–192.

Hollis, H.W., et al., "A practical approach to wound care in patients with complex enterocutaneous fistulas", Surg. Gynecol. Obstet., 161(2);178–180 (Aug. 1985). NPL–210.

Mutschler, W. et al., "Temporary skin replacement. An important component in the treatment of skin defects of various etiologies", ZFA, (and 12 sheets of English translation); S. 714–720, pp. 3–15, (1989). NPL–305.

Nikolov. A., "Vacuum treatment method in postphlebitic and varicose trophic ulcers of the lower extremities", Khirurgiia (Sofiia), (English abstract on p. 371 and 1 sheet printout from PubMed); 34(4):368–371 (1981). NPL–314.

Olenius, M., et al., "Mitotic activity in expanded human skin", Plast. Reconstr. Surg., 91;213–216 (Feb. 1993). NPL–318.

Ramirez, O.M., et al., "Optimal wound healing under Op–Site dressing", Plast. Reconstr. Surg., 73(3):474–475 (Mar. 1984). NPL–341.

Teder, H., et al., "Continuous wound irrigation in the pig", J. Invest. Surg., 3:399–407 (1990). NPL–400.

Sheppard, M.D., "Sealed drainage of wounds", The Lancet, pp. 1174–1176 (Jun. 14, 1952). NPL–410.

McCulloch, J.M., et al., "Vacuum–compression therapy for the treatment of an ischemic ulcer", Phys. Ther., 73(3):165–9 (Mar. 1993). NPL–270.

Mulder, G. D. et al. (eds.), Clinicians' Pocket Guide to Chronic Wound Repair, (Spartanburg, SC: Wound Healing Publications), pp. 54–55 (1992 or earlier). NPL–317.

Morykwas, M.J., et al., "Techniques in Use of V.A.C.™ Treatment" (in English), Acta Chir. Austriaca Supplement 150: pp. 2–28, article on pp. p. 3–4 (1998). WFU–02.

Fey, M.D., et al. "Silicone release coatings" in Handbook of pressure–sensitive adhesive technology, Satas, D., ed., Van Nostand Reinhold Company, pp. 384–403 (1982). NPL–355.

Svedman, P., "A dressing allowing continuous treatment of a biosurface,"IRCS Medical Science: Biomedical Technology; Clinical Medicine; Surgery and Transplantation, 7:221 (1979), with annotations. NPL–388.

Viljanto, J., "A new method for treatment of open wounds", Ann. Chir. Gynaecol. Fenn., (English abstract on first page, and 1 sheet printout from PubMed); 60:94–100 (1972). NPL–421.

Yusupov, Y.N., et al., "Active drainage of wounds", Vestn. Khir. Im. I.I. Grek., (with English abstract on last page, 5 sheets of English translation, 3 pp. of English translation by BlueSky publishing and 1 sheet printout from PubMed); 138(4):42–46 (Apr. 1987). NPL–452.

Zhivotaev, V.M., "Vacuum therapy of postoperative infected wounds of the urinary bladder", Klin. Khir., (and 1 sheet printout from PubMed); 5:36–39 (May 1970). NPL–453.

Chariker/Jeter/Tintle Slides "Closed Wound Suction" by Dr. Mark Chariker et al., 41 sheets, pp. 1–10, 19, 55–84 (D–041) NPL–079.

Jeter, K., list of publications, 4 sheets, no date provided (D–161) NPL–225.

*KCI v. BlueSky*, Final Jury Instructions, 84 pages, delivered to jury Jul. 14, 2006. BS–207.

Murray, J., et al., "On the Local and General Influence on the Body if Increased and Diminished Atmospheric Pressure", The Lancet, V. 1, 1834–1835, pp. 909–917. NPL–303.

Herrmann, L., et al., "The Conservative Treatment of Arteriosclerotic Peripheral Vascular Diseases", pp. 750–760. NPL–199.

Versatile I Wound Vacuum System™ for The Promotion of Wound Healing, Wound Application instructions, 1 page advertisement. NPL–418.

Bluesky Medical "The Versatile One!™", Wound Drainage and More, 1 page advertisement (labeled Spring 2003). NPL–050.

Chariker–Jeter® Wound Sealing Kit, Would Application Instructions, 1 page advertisement. NPL–078.

*Kinetic Concepts, Inc., et al., v. Bluesky Medical Corporation, et al.*, Civil Action No. SA–03–CA–0832–RF, U.S. Dist. Count, W. Dist. of TX San Antonio Div., Report of Katherine F. Jeter, Nov. 28, 2004, BS–11.

Opposition to EP 0,620,720, Appeal of Opponent Paul Harmann AG, dated Sep. 20, 2004 (with English translation), EPOPWH1–15.

Opposition EP to 0,620,720, Patentee's Grounds of Appeal dated Sep. 29, 2004, 31 pages. EPOPWH1–18.

3M™, Tegaderm Family of Transparent Dressings for Chronic Wounds, pp. 1–8 (2002). NPL–002.

ConstaVac™ Closed Wound Drainage System, Stryker Instruments, 2 pages. NPL–092.

Lower Extremity Ulcers, Chapter 9, pp. 47–57. NPL–259.

Microtek Medica, Inc. "The Microtek Complete Closed Wound Drainage System", 6 pages. NPL–285.

Rovee, David T., et al., "Effect of Local Wound Environment on Epidermal Healing", Dept. of Skin Biology, Johnson & Johnson Research, New Brunswick, NJ, pp. 159–181 (1972). NPL–348.

Turner, T.D., "Recent Advances in Wound Management Products", pp. 3–6 NPL–406.

Turner, T.D., "Semipermeable Films as Wound Dressings", Welsh School of Pharmacy, University of Wales, Great Britain, 3 pages (Jul. 31, 1984). NPL–407.

Turner, T.D., "The Development of Wound Management Products", Chronic Wound Care, pp. 31–46. NPL–408.

Winter, G.D., "Healing of Skin Wounds and the Influence of Dressings on the Repair Process", pp. 46–60 of "Surgical dressings and wound healing: proceedings of a symposium held on Jul. 7–8, 1970 at the University of Bradford," Crosby Lockwood for Bradford University Press, (1971). NPL–439.

Greer, Steven E., "Whither Subatmospheric Pressure Dressing?" the Institute of Reconstructive Plastic Surgery, The New York University Medical Center, New York, NY April Issue of Annals of Plastic Surgery 2000. NPL–180.

Mirazimov, B.M.: Free Skin Grafting of Wounds and Ulcers using the "Vacuum Treatment" Method. [Orthop. Travmatol. Protez., 28(1):54–58.] with English Trans. 1967 NPL–293.

Notice of Opposition to European Patent No. 0688189 dated Jun. 12, 2001 EPOPWH2–02.

Letter Supplemental to Notice of Opposition to European Patent No. 0688189 dated Nov. 12, 2002 EPOPWH2–05.

Interlocutory decision in Opposition proceedings in favor of patentee (Wake Forest—Argenta, et al.) Dated: Feb. 17, 2003 EPOPWH2–06.

Opposer's Appeal from Interlocutory Decision—dated Jun. 27, 2003. EPOPWH2–08.

*Kinetic Concepts, Inc., et al., v. Bluesky Medical Corporation, et al.*, Civil Action No. SA–03–CA–0832–RF, U.S. District Court, W. Dist. of Texas San Antonio Div., Plaintiffs' Responsive Claim Construction Brief dated Mar. 28, 2005. BS–148.

*Kinetic Concepts, Inc., et al., v. Bluesky Medical Corporation, et al.*, Civil Action No. SA–03–CA–0832–RF, U.S. District Court, W. Dist. of Texas San Antonio Div., Declaration of Michael J. Morykwas in Support on Plaintiffs' Responsive Claim Construction Brief dated Mar. 24, 2005. BS–149.

*Kinetic Concepts, Inc., et al., v. Bluesky Medical Corporation, et al.*, Civil Action No. SA–03–CA–0832–RF, U.S. District Court, W. Dist. of Texas San Antonio Div., Declaration of Wilson C. Hayes in Support on Plaintiffs' Responsive Claim Construction Brief dated Mar. 25, 2005. BS–150.

*Kinetic Concept, Inc., et al., v. Bluesky Medical Corporation, et al.*, Civil Action No. SA–03–CA–0832–RF, U.S. District Court, W. Dist. of Texas San Antonio Div., Plaintiffs' Brief on Claim Construction dated Mar. 7, 2005. BS–151.

*Kinetic Concepts, Inc., et al., v. Bluesky Medical Corporation, et al.*, Civil Action No. SA–03–CA–0832–RF, U.S. District Court, W. Dist. of Texas San Antonio Div., Medela AG and Medela, Inc's Opening Memorandum Regarding Construction of the Patent Claims dated Mar. 7, 2005. BS–152.

*Kinetic Concepts, Inc., et al., v. Bluesky Medical Corporation, et al.*, Civil Action No. SA–03–CA–0832–RF, U.S. District Court, W. Dist. of Texas San Antonio Div., BlueSky Medical Group Incorporated Opening Markman Brief Regarding U.S. Patent Nos. 4,969,880 and 5,636,643. BS–153.

*Kinetics Concepts, Inc., et al., v. Bluesky Medical Corporation, et al.*, Civil Action No. SA–03–CA–0832–RF, U.S. District Court, W. Dist. of Texas San Antonio Div., Plaintiffs' Reply Brief on Claim Construction dated Apr. 18, 2005. BS–147.

*Kinetic Concepts, Inc., et al., v. Bluesky Medical Corporation, et al.*, Civil Action No. SA–03–CA–0832–RF, U.S. District Court, W. Dist. of Texas San Antonio Div., Medela AG and Medela Inc.'s Response on Claim Construction dated Mar. 28, 2005. BS–154.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Bluesky Medical Group Incorporated's Opposition Markman Brief Regarding U.S. Patent Nos. 4,969,880 and 5,636,643. BS–155.

Opposition EP to 0,620,720. Third Party Observations dated Feb. 16, 2005. EPOPWH1–19.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Markman Presentation of May 12, 2005. BS–156.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Blue Sky Medical Corp.'s Markman Presentation dated May 12, 2005. BS–157.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Medela Markman Presentation dated May 12, 2005. BS–158.

Opposition EP to 0,620,720, Response of Opponent Paul Hartmann AG dated Apr. 25, 2005 (with English translation). EPOPWH1–17.

Email dated Jan. 14, 2002 with attachments, including "Report of Meeting with DG Consulting" dated Jan. 10, 2002, 5 sheets, (Exhibit D–157). NPL–137.

Letter dated Jan. 25, 2002 from Charles C. Valauskas to Mr. Richard Weston Regarding: Argenta "Wound Treatment" Patent Evaluation, 15 pages, (Exhibit D–388). NPL–254.

Letter to European Patent Office regarding Observations by a third party pursuant to Art. 115 EPC, 3 sheets, dated Mar. 6, 2006. EPOPWH1–26.

Letter to Mr. Urs Tanner from Michael Baniak dated Aug. 23, 2004 re: Updated Opinion of Non–infringement and Invalidity of Zamierowski U.S. Patent 4,969,880 (Exhibit D–140). NPL–255.

Morykwas, Laboratory Notebook pages and charts; 38 pages (Exhibit D–46) dated prior to Mar. 1993 WFU–45.

Morykwas, Laboratory notebook pages and charts, 16 sheets. (Exhibit D–286) dated prior to Mar. 1993 WFU–46.

Morykwas, Laboratory notebook pages and charts, 17 sheets. (Exhibit D–233) dated prior to Nov. 1991 WFU–47.

Morykwas, Laboratory notebook pages of charts, Aug. 29 and Dec. 19, 3 sheets, (Exhibit P–664) dated prior to Nov. 1991 WFU–48.

Opposition EP to 0620720, Communication of Opponent Hartman (Brief in Reply to Patentee's Brief Oct. 15, 1999) dated Mar. 8, 2000 (and English translation). EPOPWH1–04.

Opposition EP to 0620720, Communication of Opponent Hartman (Opening Brief) dated Dec. 16, 1998). EPOPWH1–01.

Opposition EP to 0620720, Communication of Opponent Hartman dated Jul. 19, 2004. EPOPWH1–14.

Opposition EP to 0620720, Communication of Opponent Hartman dated Sep. 20, 2004 with Eng. Translation. EPOPWH1–15.

Opposition EP to 0620720, Communication of Opponent Mondomed dated Dec. 17, 1998. EPOPWH1–02.

Opposition EP to 0620720, Communication of Patentee (Response Brief) dated Oct. 15, 1999. EPOPWH1–03.

Opposition EP to 0620720, Opponents Grounds of Appeal, dated Sep. 29, 2004, with English translation. EPOPWH1–18.

Opposition EP to 0620720, Preliminary Opinion of Opposition Division dated Aug. 11, 2003 (5 pages), Summons to Oral Proceedings Pursuant to Rule 71(1) EPC Dated Aug. 12, 2003, (6 pages). EPOPWH1–08.

Photographs of wound coverings, 16 sheets, (Exhibit D–240) NPL–331.

Slides and photographs, 19 sheets, (Exhibit D–152) (allegedly dated 1987). NPL–376.

Slides, drawings, photographs and presentation slides, 20 sheets, (Exhibit D–151) (allegedly dated 1987). NPL–377.

Morykwas, Laboratory Notebook pages and charts; (D–46) dated prior to Nov. 1991 WFU–49.

Morykwas, Laboratory Notebook pages and charts; (D–286) dated prior to Nov. 1991 WFF–50.

Reid, D., "Information on Cupping or Using Suction Cups on Wounds and for Healing Purposes", from Chines Herbal Medicine (2 pages). NPL–345.

"Wound Suction; Better Drainage With Fewer Problems", Nursing 75, October, pp. 52–55. NPL–447.

Grams Aspirator, et al., Grams Medical, catalog pages (3 pages) (prices as of Aug. 1991 and Sep. 1992). NPL–175.

Medela Dominant promotional literature (2 pages of photos) (labeled circa 1984–1985). NPL–274.

Usage Manual Pleurasug TDR (2 pages of diagrams with descriptions). NPL–412.

Moloney, G., "Apposition and Drainage of Large Skin Flaps", Oxford, England, pp. 173–179 (Feb. 1957). NPL–296.

Miles, W., "Technique of the Radical Operation for Cancer of the Rectum", The British Journal of Surgery, 1914–1915, pp. 292–305. NPL–286.

Hilsabeck, J., "The Presacral Space as a Collector of Fluid Accumulations Following Rectal Anastomosis", American Society of Colon and Rectal Surgeons, (Oct. 1982), pp. 680–684, vol. 25, No. 7. NPL–206.

Eisenbud, D., "Modern Wound Management", Adadem Publishing, pp. 109–116 (Jan. 1999). NPL–134.

Hunt, T.K., et al., eds., "Dead Space" and "Drainage", Fundamentals of Wound Management, pp. 416–447 (1979). NPL–186.

McFarlane, R., "The use of Continuous Suction Under Skin Flaps", British Journal of Plastic Surgery, pp. 77–86 (1958–1959). NPL–271.

Taylor, V., "Meeting the Challenge of Fistulas & Draining Wounds", Nursing80, June pp. 45–51. NPL–398.

Part III. Resolving Selected Clinical Dilemmas, pp. 17–20. NPL–328.

Manualectric Breastpump, Catalog pages (4 pages), diagrams and descriptions. NPL–266.

OpSite Wound Dressings, "Do Your Pressure Sore Dressings Shape Up to the OpSite Standard", 2 pages of advertisements. NPL–319.

Dow Corning Silastic® Foam Dressing: A New Concept in the Management of Open Granulating Wounds, 2 pages of advertisements. NPL–121.

Pleur$_x$ Pleural Catheter, Denver Biomedical, 4 pages of brochure. NPL–334.

Moserova, J., "The Healing and Treatment of Skin Defects", pp. 103–151 (1989) NPL–299.

Rabkin, J., et al., "Infection and Oxygen", Problem Wounds: The Role of Oxygen, pp. 1–15 (1987). NPL–338.

Paradise Valley Hospital, The Center for Wound Healing and Hyperbaric Medicine, 3 pages of brochure. NPL–326.

DuoDERM Hydroactive™ Dressing, "In wound management—Now, a proven environment for fast healing", 1 page advertisement. NPL–126.

Howmedica porto–vac®, "Gentle, Steady Wound Drainage", 1 page advertisement. NPL–212.

Silicone from CUI (Cox–Uphoff International), "Flexability", 1 page advertisement. NPL–371.

Grabowski, S., "Leczenie ran z zastosowaniem podcisnienia", article, pp. 19–21, English abstract on p. 21 and 1 sheet printout from PubMed, (Jan. 1, 1964). NPL–174.

Cooper, D., "Wound Healing", Nursing Clinics of North America, pp. 163–164 (Mar. 1990). NPL–096.

Cook Pneumothorax Catheter Set, Wayne Pneumothorax Catheter Set, Emergency Medicine, Videotape advertisement. NPL–094.

Schaffer, D., "Closed Suction", Nursing97, Nov., http://www.springnet.com, pp. 62–64. NPL–357.

Carroll, P., "The Principles of Vacuum and Its Use in the Hospital Environment", Ohmeda, pp. 1–30 and cover sheet. NPL–070.

Healing of Full Thickness Defects in Swine NPL–197.

Opposition EP to 0,620,720, Summons to Oral Proceedings Appeal dated Dec. 21, 2005. EPOPWH1–20.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs Letter to Honorable Royal Furgeson dated Jan. 3, 2006. BS–130.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendants Letter to Honorable Royal Furgeson dated Jan. 3, 2006. BS–131.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Reply Claim Construction Brief with Exhibits dated Nov. 11, 2005. BS–132.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Surreply Further Opposing Defendant Bluesky Medical Group Incorporated's and Richard Weston's Motions for Summary Judgment on the '643 and '880 Patents with Exhibits dated Oct. 14, 2005. BS–133.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Opposition to Defendant Bluesky Medical Group Incorporated's and Richard Weston's Motion for Summary Judgment on the '880 Patent with Exhibits dated Sep. 12, 2005. BS–134.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Bluesky and Richard Weston's First Amended Crossclaims and Answer to Plaintiffs' Fourth Amended Complaint, Counterlclaims, and Joinder of Wake Forest University dated Nov. 15, 2005. BS–135.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Bluesky and Richard Weston's Objections and Responses to Plaintiffs' Fifth Request for Production dated Dec. 9, 2005. BS–136.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendants' Response Brief Regarding Second Claim Construction Hearing ('081 Patent and Certain Claims of the '643 Patent) with Exhibits dated Oct. 25, 2005. BS–137.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Medela, Inc.'s Objections and Responses to Plaintiffs' Sixth Request for Production of Documents dated Dec. 9, 2005. BS–138.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendant Bluesky and Richard Weston's First Amended Crossclaim and Answer to Plaintiffs' Fourth Amended Complaint, Counterclaims, and Joinder of Wake Forest University dated Nov. 15, 2005. BS–139.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs' Responsive Claim Construction Brief on the Disputed Claim Terms from the '6443 and '081 Patents with Exhibits dated Oct. 25, 2005. BS–140.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Markman Hearing Medela Presentation, pp. 1–78. BS–245.

Opposition EP to 0,618,189 New European Patent Specification EP 0688189B2. EPOPWH2–01.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Supplemental Expert Report of Wilson C. Hayes, Ph.D. Concerning Infringement of Newly Asserted Claims of U.S. Patent Nos. 5,636,643 and 5,645,081 dated Dec. 19, 2005. BS–55.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Dennis P. Orgill, M.D., Ph.D. with Exhibits dated Dec. 29, 2005. BS–1.

Opposition EP to 0,618,189 Decision to Maintain the European Patent in Amended Form (Article 102(3) EPC) dated Apr. 22, 2005, 1 page. EPOPWH2–10.

Opposition EP to 0,618,189 Letter relating to Appeal Procedure dated Mar. 5, 2004, 10 pages. EPOPWH2–09.

Opposition EP to 0,618,189 Letter relating to Appeal Procedure dated Jun. 27, 2003. EPOPWH2–08.

Opposition EP to 0,618,189 Interlocutory Decision in Opposition Proceedings with Grounds for the Decision dated Feb. 17, 2003. EPOPWH2–06.

Opposition EP to 0,618,189 Minutes of the Oral Proceedings, Documents for the Maintenance of the Patent as Amended, Annex to the Communication dated Feb. 17, 2003. EPOPWH2–07.

Opposition EP to 0,618,189 Letter Pursuant to Rule 71a EPC and all Other Letter during Oral Proceedings dated Nov. 11, 2002. EPOPWH2–04.

Opposition EP to 0,618,189 Reply of the Patent Proprietor to the Notice(s) of Opposition dated Mar. 15, 2002. EPOPWH2–03.

Opposition EP to 0,618,189 Notice of Opposition dated Jun. 12, 2001. EPOPWH2–02.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs Response to Claim Construction Reply Letter dated Jan. 6, 2006. BS–142.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Defendants Medela Claim Construction Letter dated Jan. 5, 2006. BS–143.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Harriet W. Hopf, M.D. on New Claims dated Jan. 4, 2006. BS–2.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Lydia Razran Stone, Ph.D. dated Dec. 29, 2005 with CV. BS–3.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Plaintiffs Fourth Amended Complaint with Declaration of Trang Tran with Exhibits dated Jun. 30, 2005. BS–144.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Transcript Deposition of Michael John Morykwas dated Dec. 6, 2005 with Exhibits. BS–64.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Deposition Transcript of Doris Ritter–Wiegand with Exhibits dated Dec. 15, 2005. BS–65.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Transcript of Videotaped Deposition of Katherine Jeter with Exhibits dated Nov. 29, 2005. BS–66.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Supplemental Expert Report of Mark Chariker, M.D. dated Dec. 19, 2005. BS–24.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Vincent B. Pizziconi, Ph.D., with Exhjbits dated Dec. 23, 2005. BS–5.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Amended Order Construing Patent '643 Claims Terms dated Jan. 25, 2006. BS–145.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Order Construing Patents '643 and '081 Claim Terms dated Jan. 24, 2006. BS–146.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Expert Report of Michael A. O'Neil dated Jan. 4, 2006. BS–6.

*Kinetic Concepts, Inc., et al.,* v. *Bluesky Medical Corporation, et al.,* Civil Action No. SA–03–CA–0832–RF, U.S. District Court, W. Dist. of Texas San Antonio Div., Partial Transcript of Videotaped Deposition James Spahn dated May 4, 2005. BS–67.

Townsend, P.L.G., "The Quest For A Cheap and Painless Donor–Site Dressing", Burns, 2, pp. 82–85 (Jan. 1976). NPL–404.

Langworthy, M., et al., "Treatment of the Mangled Lower Extremity After a Terrorist Blast Injury", Clinical Orthopaedics and Related Research, No. 422, pp. 88–96 (May 2004). NPL–251.

Park, G.B., et al., "The Design and Evaluation of a Burn Wound Covering", Supplied by The British Library—"The Word's Knowledge", pp. 11–15 (1978). NPL–327.

ACU–derm® Transparent Moisture Vapor Permeable Polyurethane Dressing, pp. 1–14. NPL–003.

3M Ioban 2, Breathability, Conformability and Strength, Breathability—Moisture Vapor Transmission Rate and Conformability and Strength—Tensile Strength, Elongation and Fn Modulus Test (1 page). NPL–001.

Smith&nephew website printout, Would Management, FAQs. NPL–380.

"Moist Wound Dressings" from Physicians Instruction Book for Moist Wound Healing. NPL–295.

*Kinetic Concepts, Inc., et al.* vs. *Bluesky Medical Corporation, et al.;* Civil Action No. SA 03 CA 0832: Plaintiff's Original Complaint dated Aug. 28, 2003. BS–120.

*Kinetic Concepts, Inc., et al.* vs. *Bluesky Medical Corporation, et al.;* Civil Action No. SA 03 CA 0832: Plaintiffs' First Amended Complaint dated Sep. 8, 2003. BS–121.

*Kinetic Concepts, Inc., et al.* vs. *Bluesky Medical Corporation, et al.;* Civil Action No. SA 03 CA 0832: Defendant BlueSky Medical Corporation's Original Answer to Plaintiff's First Amended Complaint dated Sep. 30, 2003. BS–122.

*Kinetic Concepts, Inc., et al.* vs. *Bluesky Medical Corporation, et al.;* Civil Action No. SA 03 CA 0832: Answer, Additional Defenses, Counterclaims and Jury Demand of Medela, Inc. (Reponse due: Oct. 27, 2003—20 days after service) dated Oct. 6, 2003. BS–123.

*Kinetic Concepts, Inc., et al.* vs. *Bluesky Medical Corporation, et al.;* Civil Action No. SA 03 CA 0832: Plaintiff's Reply to Defendant BlueSky Medical Corporation's Counterclaim dated Oct. 23, 2003. BS–124.

*Kinetic Concepts, Inc., et al.* vs. *Bluesky Medical Corporation, et al.;* Civil Action No. SA 03 CA 0832: Summary of Appendix in Support of Medela AG's Motion to Dismiss for Lack of Personal Jurisdiction or, Alternatively, to Dismiss for Failure to State a Claim and for Partial Summary Judgment dated Oct. 24, 2003. BS–125.

*Kinetic Concepts, Inc., et al.* vs. *Bluesky Medical Corporation, et al.;* Civil Action No. SA 03 CA 0832: Original Answer of Defendant Patient Care Systems, Inc., dated Oct. 7, 2003. BS–126.

*Kinetic Concepts, Inc., et al.* vs. *Bluesky Medical Corporation, et al.;* Civil Action No. SA 03 CA 0832: Medela AG's Motion to Dismiss for Lack of Peronsal Jurisdiction or Alternatively, to Dismiss for Failure to State a Claim and For Partial Summary Judgment dated Oct. 24, 2003. BS–127.

*Kinetic Concepts, Inc., et al.* vs. *Bluesky Medical Corporation, et al.;* Civil Action No. SA 03 CA 0832: Plaintiff's Reply to Defendant Medela, Inc.'s Counterclaim dated Oct. 27, 2003. BS–128.

*Kinetic Concepts, Inc., et al.* vs. *Bluesky Medical Corporation, et al.;* Civil Action No. SA 03 CA 0832: Plaintiff's Response to Medela AG's Motion to Dismiss for Lack of Personal Jurisdiction, Motion to Dismiss for Failure to State a Claim, and Motion for Partial Summary Judgment, dated Nov. 10, 2003. BS–129.

*Kinetic Concepts, Inc., et al., v. Bluesky Medical Corporation, et al.,* Civil Action No. SA–03–CA–0832–RF, U.S. District Court, W. Dist. of Texas San Antonio Div., Deposition transcript with Exhibits of Mark Chariker dated May 6, 2005. BS–76.

*Kinetic Concepts, Inc., et al., v. Bluesky Medical Corporation, et al.,* Civil Action No. SA–03–CA–0832–RF, U.S. District Court, W. Dist. of Texas San Antonio Div., Deposition transcript with Exhibits of David S. Zamierowski dated Feb. 15, 2005. BS–77.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report with Exhibits of Harriet W. Hopf dated May 10, 2005, along with Supplemental Expert Report with Exhibits dated May 25, 2005. BS–17.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report with Exhibits of Susan Mendez–Eastman dated Jan. 7, 2004. BS–18.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report with Exhibits of Jose Diaz dated Nov. 26, 2004. BS–19.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report with Exhibits of Jeffrey Niezgoda dated Nov. 23, 2004. BS–20.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report with Exhibits of Kathleen Satterfield dated Nov. 29, 2004. BS–21.

*Kinetic Concepts, Inc., et al., v. Bluesky Medical Corporation, et al.,* Civil Action No. SA–03–CA–0832–RF, U.S. District Court, W. Dist. of Texas San Antonio Div., Exhibits 281–288 of previously submitted Transcription of Deposition of Michael John Morykwas, PhD. dated Jan. 13, 2005. BS–78.

*Kinetic Concepts, Inc., et al., v. Bluesky Medical Corporation, et al.,* Civil Action No. SA–03–CA–0832–RF, U.S. District Court, W. Dist. of Texas San Antonio Div., Report of Professor Thomas K. Hunt, M.D., pp. 1–14 Jan. 13, 2005. BS–29.

*Kinetic Concepts, Inc., et al., v. Bluesky Medical Corporation, et al.,* Civil Action No. SA–03–CA–0832–RF, U.S. District Court, W. Dist. of Texas San Antonio Div., Report of Mark Chariker, M.D., pp. 1–8, Jan. 13, 2005. BS–8.

*Kinetic Concepts, Inc., et al., v. Bluesky Medical Corporation, et al.,* Civil Action No. SA–03–CA–0832–RF, U.S. District Court, W. Dist. of Texas San Antonio Div., Report of James Spahn, M.D., pp. 1–6 and Exhibit C pp. 9–10, Jan. 6, 2005. BS–9.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report of Michael H. Baniak, pp. 1–79 and Exhibit D pp. 1–3 including un–published materials listed therein and Exhibit E pp. 1–5, Jan. 7, 2005. BS–10.

*Kinetic Concepts, Inc., et al., v. Bluesky Medical Corporation, et al.,* Civil Action No. SA–03–CA–0832–RF, U.S. Dist. Count, W. Dist. of TX San Antonio Div., Report of Katherine F. Jeter, Nov. 28, 2004. BS–11.

*Kinetic Concepts, Inc., et al., v. Bluesky Medical Corporation, et al.,* Civil Action No. SA–03–CA–0832–RF, U.S. Dist. Count, W. Dist. of TX San Antonio Div., Report of Wilson C. Hayes, Ph.D, Nov. 29, 2004, pp. 1–15 and Exhibit C (2 pages). BS–12.

Erdmann, D., et al., "Abdominal Wall Defect and Enterocutaneous Fistula Treatment with the Vacuum–Assisted Closure (V.A.C.) System", Plastic and Reconstructive Surgery, vol. 108, No. 7, pp. 2066–2068 (Dec. 2001). NPL–141.

Chariker–Jeter® Wound Drainage Kit, BlueSky Medical, 2 page advertisement with copy of business card from Quality Medical Supply. NPL–077.

Chariker–Jeter® Wound Drainage Kit Instructions, Item #500.7777, BlueSky Medical, 2 pages. NPL–076.

Wooding–Scott® Wound Drainage Kit Contents, Item #500.8888, 1 page. NPL–445.

Coyle, M., et al., "A Case Study: Positive Outcomes to Negative Pressure Wound Therapy—A collaborative assessment", Hospital of Saint Raphael, 1 page chart. NPL–102.

Nemoto, H., et al., "Stories From the Bedside: Purple Urine Bage Syndrome Development in Ileal Conduit" WCET, Journal 23(2), pp. 31–34. NPL–310.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report of Dennis P. Orgill, M.D., Ph.D., Feb. 18, 2005. BS–13.

*Kinetic Concepts, Inc., et al., v. Bluesky Medical Corporation, et al.,* Civil Action No. SA–03–CA–0832–RF, U.S. District Court, W. Dist. of Texas San Antonio Div., Rebuttal Expert Report of Wilson C. Hayes, Ph.D. In Reponse to the Report of Michael H. Baniak, Feb. 18, 2005. BS–14.

*Kinetic Concepts, Inc., et al., v. Bluesky Medical Corporation, et al.,* Civil Action No. SA–03–CA–0832–RF, U.S. District Court, W. Dist. of Texas San Antonio Div., Expert Report of John T. Goolkasian in Rebuttal to Report of Michael H. Baniak, Feb. 18, 2005. BS–15.

*Kinetic Concepts, Inc., et al., v. Bluesky Medical Corporation, et al.,* Civil Action No. SA–03–CA–0832–RF, U.S. District Court, W. Dist. of Texas San Antonio Div., Rebuttal Expert Report of Louis C. Argenta, M.D. to Expert Report of Michael H. Baniak, Feb. 18, 2005. BS–16.

*Kinetic Concepts, Inc., et al., v. Bluesky Medical Corporation, et al.,* Civil Action No. SA–03–CA–0832–RF, U.S. District Court, W. Dist. of Texas San Antonio Div., Letter Brief from BlueSky Medical dated May 31, 2005. BS–159.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs First Letter Brief from Markman hearing dated May 26, 2005. BS–160.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs Second Letter Brief from Markman hearing dated May 31, 2005. BS–161.

*Kinetic Concepts, Inc., et al., v. Bluesky Medical Corporation, et al.,* Civil Action No. SA–03–CA–0832–RF, U.S. District Court, W. Dist. of Texas San Antonio Div., Transcription of Videotaped Deposition of Louis C. Argenta, M.D., Apr. 29, 2005. BS–68.

*Kinetic Concepts, Inc., et al., v. Bluesky Medical Corporation, et al.,* Civil Action No. SA–03–CA–0832–RF, U.S. District Court, W. Dist. of Texas San Antonio Div., Transcription of Videotaped Deposition of Michael Allan Batalia, PhD. Jan. 12, 2005. BS–69.

*Kinetic Concepts, Inc., et al., v. Bluesky Medical Corporation, et al.,* Civil Action No. SA–03–CA–0832–RF, U.S. District Court, W. Dist. of Texas San Antonio Div., Transcription of Videotaped Deposition of Michael John Morykwas, PhD. Jan. 13, 2005. BS–70.

*Kinetic Concepts, Inc., et al., v. Bluesky Medical Corporation, et al.,* Civil Action No. SA–03–CA–0832–RF, U.S. District Court, W. Dist. of Texas San Antonio Div., Defendents Medela AG and Medela, Inc.'s Motion for Leave to Amend Designation of Expert Witnesses dated May 18, 2005. BS–162.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Answer to Defendant Bluesky Medical Group Incorporated's Crossclaim dated Jun. 1, 2005. BS–163.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Answer to Defendant Richard Weston's Counterclaim dated Jun. 1, 20051. BS–164.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Answer to Defendant Medela Inc.'s Amended Counterclaims dated Jun. 1, 2005. BS–165.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Answer to Defendant Medela AG's Amended Counterclaims dated Jun. 1, 2005. BS–166.

*Kinetic Concepts, Inc., et al., v. Bluesky Medical Corporation, et al.,* Civil Action No. SA–03–CA–0832–RF, U.S. District Court, W. Dist. of Texas San Antonio Div., Objections and Answers to Medela's Supoena in a Civil Case for Production of Documents and Deposition on Written Questions to Wake Forest University Baptist Medical Center dated Jun. 1, 2005. BS–167.

*Kinetic Concepts, Inc., et al., v. Bluesky Medical Corporation, et al.,* Civil Action No. SA–03–CA–0832–RF, U.S. District Court, W. Dist. of Texas San Antonio Div., Medela, Inc. and Medela AG's Reply in Support of Motion for Leave to File Amended Answers to Third Amended Complaint, Additional Defenses, Second Amended Counterclaims and Jury Demands dated Jun. 1, 2005. BS–168.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Opposition to Medela AG and Medela Inc.'s Motion for Leave to Amend Designation of Expert Witnesses and Request for Hearing dated Jun. 1, 2005. BS–169.

*Kinetic Concepts, Inc., et al., v. Bluesky Medical Corporation, et al.,* Civil Action No. SA–03–CA–0832–RF, U.S. District Court, W. Dist. of Texas San Antonio Div., Objections and Answers to Medela, Inc.'s Supoena in a Civil Case and Deposition on Written Questions to Dr. Joseph Molnar and Dr. Lawrence Webb dated Feb. 24, 2005. BS–170.

*Kinetic Concepts, Inc., et al., v. Bluesky Medical Corporation, et al.,* Civil Action No. SA–03–CA–0832–RF, U.S. District Court, W. Dist. of Texas San Antonio Div., Ordering Adopting Stipulations of Parties Regarding Claim Term Construction dated May 12, 2005. BS–171.

*Kinetic Concepts, Inc., et al., v. Bluesky Medical Corporation, et al.,* Civil Action No. SA–03–CA–0832–RF, U.S. District Court, W. Dist. of Texas San Antonio Div., Order Construing Patent '643 Claim Terms dated Jun. 28, 2005. BS–172.

Opposition EP to 0,620,720. Patentee's Response to Grounds of Appeal Filed By Opponent, Paul Hartmann AG dated Apr. 25, 2005. EPOPWH1–16.

*Kinetic Concepts, Inc., et al., v. Bluesky Medical Corporation, et al.,* Civil Action No. SA–03–CA–0832–RF, U.S. District Court, W. Dist. of Texas San Antonio Div., Plaintiffs' Fourth Amended Complaint dated Jun. 30, 2005. BS–173.

*Kinetic Concepts, Inc., et al., v. Bluesky Medical Corporation, et al.,* Civil Action No. SA–03–CA–0832–RF, U.S. District Court, W. Dist. of Texas San Antonio Div., Kinetic Concepts, Inc.'s Supplemental Answers to Bluesky Medical Corporation's First Set of Interrogatories dated Jul. 6, 2005. BS–174.

*Kinetic Concepts, Inc., et al., v. Bluesky Medical Corporation, et al.,* Civil Action No. SA–03–CA–0832–RF, U.S. District Court, W. Dist. of Texas San Antonio Div., KCI Licensing, Inc.'s Supplemental Answers to Medela, Inc.'s First Set of Interrogatories dated Jul. 6, 2005. BS–175.

*Kinetic Concepts, Inc., et al., v. Bluesky Medical Corporation, et al.,* Civil Action No. SA–03–CA–0832–RF, U.S. District Court, W. Dist. of Texas San Antonio Div., Wake Forest University Health Sciences' Supplemental Answers to Medela Inc.'s First Set of Interrogatories dated Jul. 6, 2005. BS–176.

*Kinetic Concepts, Inc., et al., v. Bluesky Medical Corporation, et al.,* Civil Action No. SA–03–CA–0832–RF, U.S. District Court, W. Dist. of Texas San Antonio Div.,Amended Answer to Third Amended Complaint, Additional Defenses, Second Amended Counterclaims and Jury Demand of Medela, Inc. dated Apr. 29, 2005. BS–177.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Answer to Third Amended Complaint, Additonal Defenses, Amended Counterclaims and Jury Demand of Defendant Medela AG dated Feb. 11, 2005. BS–178.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Deposition transcript with Exhibits of Shelly Taylor dated Nov. 23, 2004. BS–71.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Deposition transcript with Exhibits of Michael Miller, D.O. dated Mar. 8, 2005. BS–72.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Medela AG's First Supplemental Response to Plaintiffs' First Interrogatories To Defendant Medela AG dated Jul. 13, 2005. BS–179.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Medela Inc.'s First Supplemental Response to Plaintiffs' First Interrogatories To Defendant Medela, Inc. dated Aug. 16, 2005. BS–180.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Deposition transcript with Exhibits of Matthew C. Dairman, Feb. 3, 2005. BS–73.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Deposition transcript with Exhibits of Ronald C. Hamaker, May 26, 2005. BS–74.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Deposition transcript with Exhibits of Mordechai Twena, Jan. 25, 2005. BS–75.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Plaintiffs' Preliminary Proposed Constructions of Newly Asserted Claims From the '643 and '081 Patents dated Sep. 12, 2005. BS–181.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Plaintiffs' Opposition to Defendant Bluesky Medical Group Incorporated's and Richard Weston's Motion for Summary Judgment on the '643 Patent, including Declaration of Wilson C. Hayes in Support Thereof including Exhibits. BS–182.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Plaintiffs' Opposition to Defendant Bluesky Medical Group Incorporated's and Richard Weston's Motion for Summary Judgment on the '880 Patent, including Declaration of Wilson C. Hayes in Support Thereof including Exhibits. BS–183.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Answer To Fourth Amended Complaint, Additional Defenses, Third Amended Counterclaims and Jury Demand of Defendant Medela AG, Jul. 18, 2005. BS–184.

*Kinetic Concepts, Inc., et al.*, v. *Bluesky Medical Corporation, et al.*, Civil Action No. SA–03–CA–0832–RF, U.S. District Court, W. Dist. of Texas San Antonio Div., Answer To Fourth Amended Complaint, Additional Defenses, Third Amended Counterclaims and Jury Demand of Defendant Medela, Inc., Jul. 18, 2005. BS–185.

*KCI* v. *BlueSky*: BlueSky Medical Group Inc. and Richard Weston's motion to exclude certain expert testimony dated Apr. 21, 2006. BS–208.

*KCI* v. *BlueSky*: Medela's Motion to exclude proposed trial testimony of plaintiff's experts Louis C. Argenta, Dennis P. Orgill and Wilson C. Hayes, dated Apr. 21, 2006. BS–209.

*KCI* v. *BlueSky*: Plaintiff's motion to exclude opinions of Vincent Pizziconi dated Apr. 21, 2006. BS–210.

*KCI* v. *BlueSky*: Plaintiff's motion to exclude certain opinions of Michael O'Neil dated Apr. 21, 2006. BS–211.

*KCI* v. *BlueSky*: Medela's response to plaintiff's motion to exclude opinions of Harriet Hopf with Exhibits dated Apr. 28, 2006. BS–212.

*KCI* v. *BlueSky*: Medela's response to plaintiff's motion to exclude opinions of Michael O'Neil and motion to exclude opinions of John T. Goolkasian with Exhibits dated Apr. 28, 2006. BS–213.

*KCI* v. *BlueSky*: Medela's response to plaintiff's motion to exclude opinions of James Spahn dated Apr. 28, 2006. BS–214.

*KCI* v. *BlueSky*: Plaintiff's response to Medela's motion to exclude proposed trial testimony of Louis C. Argenta, Dennis P. Orgill, and Wilson C. Hayes, dated May 1, 2006. BS–215.

*KCI* v. *BlueSky*: Medela's Renewed Motion for Judgment as a Matter of Law, or, in the alternative, a New Trial, on Patent Invalidity, dated Sep. 13, 2006. BS–216.

*KCI* v. *BlueSky*: Medela's Motion for a New Trial on Unenforceability, dated Sep. 13, 2006. BS–217.

Claim Chart of Asserted Claims of U.S. Patent 5,636,643 to Argenta, 3 pages. BS–218.

Claim Invalidity Analysis of U.S. Patent 5,636,643 to Argenta, et al., 34 pages, Mar. 2004. BS–219.

*KCI* v. *BlueSky*: Letter dated Dec. 9, 2005 from the Honorable Royal Ferguson to attorneys in *KCI* v. *BlueSky* regarding claim construction. BS–220.

*KCI* v. *BlueSky*, Letter from Valery Gilevich, M.D. to Kirt S. O'Neill, dated May 28, 2006 concerning review of English translation of Russian article. BS–221.

*KCI* v. *BlueSky*, Second Amended Order Construing Patent '643 and '081 Claim Terms dated Jun. 29, 2006. BS–222.

*KCI* v. *BlueSky*, Trial Transcript, dated Jun. 1, 2006 BS–99.

*KCI* v. *BlueSky*, Trial Transcript of Argenta, dated Jun. 2, 2006 BS–100.

*KCI* v. *BlueSky*, Trial Transcript of Argenta/Morykwas, dated Jun. 5, 2006 BS–101.
*KCI* v. *BlueSky*, Trial Transcript of Morykwas/Leininger/Weston, dated Jun. 6, 2006 BS–102.
*KCI* v. *BlueSky*, Trial Transcript of Weston, dated Jun. 7, 2006 BS–103.
*KCI* v. *BlueSky*, Trial Transcript of Weston, dated Jun. 8, 2006 BS–104.
*KCI* v. *BlueSky*, Trial Transcript of Niezgoda, dated Jun. 9, 2006 BS–105.
*KCI* v. *BlueSky*, Trial Transcript of Miller/Anderson/Ware, dated Jun. 19, 2006 BS–106.
*KCI* v. *BlueSky*, Trial Transcript of Ware/Resietter/Condor/Malackowski, dated Jun. 20, 2006 Bs–107.
*KCI* v. *BlueSky*, Trial Transcript of Malackowski/Dairman/Leszkiewicz/Banes/John, dated Jun. 21, 2006 BS–108.
*KCI* v. *BlueSky*, Trial Transcript of Johnson/Quackenbush, dated Jun. 29, 2006 BS–109.
*KCI* v. *BlueSky*, Trial Transcript of Quackenbush/Laurel, dated Jun. 30, 2006 BS–110.
*KCI* v. *BlueSky*, Trial Transcript for Escobedo/Satterfield/Chariker, dated Jul. 5, 2006 BS–111.
*KCI* v. *BlueSky*, Trial Transcript for Chariker/Hamaker/Spahn/Jeter/Hopf, dated Jul. 6, 2006 BS–112.
*KCI* v. *BlueSky*, Trial Transcript for Hopf/Lockhart, dated Jul. 7, 2006 BS–113.
*KCI* v. *BlueSky*, Trial Transcript for Hopf, dated Jul. 10, 2006 BS–114.
*KCI* v. *BlueSky*, Trial Transcript for Pizziconi/Orgill, dated Jul. 11, 2006 BS–115.
*KCI* v. *BlueSky*, Trial Transcript for Orgill/Bridi/McGregor/Girolami/Taylor, dated Jul. 12, 2006 BS–116.
*KCI* v. *BlueSky*, Trial Transcript for Campbell, dated Jul. 13, 2006 BS–117.
*KCI* v. *BlueSky*, Trial Transcript dated Jul. 14, 2006 BS–118.
*KCI* v. *BlueSky*, Trial Transcript dated Jul. 17, 2006 BS–119.
*KCI* v. *BlueSky*, Deposition of Penny Campbell with Exhibits dated Jan. 17, 2005. BS–80.
*KCI* v. *BlueSky*, Transcript of Deposition of Mark Chariker, M.D., with Exhibits, dated Apr. 5, 2006. BS–81.
*KCI* v. *BlueSky*, Transcript of Deposition of Harriet W. Hopf, M.D., with Exhibits, dated Jul. 4, 2006. BS–82.
*KCI* v. *BlueSky*, Deposition transcript with Exhibits of Thomas K. Hunt dated Apr. 21, 2005. BS–83.
*KCI* v. *BlueSky*, Transcript of Deposition of Donna Goudberg Lockhart, with Exhibits, dated Jul. 7, 2006. BS–84.
*KCI* v. *BlueSky*, Transcript of Deposition of Marie Louise Lachute McGregor, dated Jul. 11, 2006. BS–85.
*KCI* v. *BlueSky*, Transcript of Deposition of Michael A. O'Neil, with Exhibits, dated Apr. 6, 2006. BS–86.
*KCI* v. *BlueSky*, Transcript of Deposition of Vincent B. Pizziconi, Ph.D., with Exhibits, dated Apr. 7, 2006. BS–87.
*KCI* v. *BlueSky*, Transcript of Deposition of David Tumey, with Exhibits, dated Jun. 15, 2006. BS–88.
*KCI* v. *BlueSky*, Transcript of Deposition of Tianning Xu, with Exhibits, dated Apr. 27, 2006. BS–89.
*KCI* v. *BlueSky*, Videotaped Deposition of Louis C. Argenta, M.D., with Exhibits, Winston–Salem, North Carolina, Friday, Mar. 17, 2006. BS–90.
*KCI* v. *BlueSky*, Transcript of Deposition of John T. Goolkasian, Esq., with Exhibits, dated Apr. 19, 2006. BS–91.
*KCI* v. *BlueSky*, Transcript of Deposition of Wilson C. Hayes, Ph.D., with Exhibits, dated Mar. 29, 2006. BS–92.
*KCI* v. *BlueSky*, Transcript of Deposition of Cynthia Ann Miller, with Exhibits, dated May 24, 2006. BS–93.
*KCI* v. *BlueSky*, Transcript of Deposition of Jeffrey A. Niezgoda, M.D., dated Jun. 8, 2006. BS–95.
*KCI* v. *BlueSky*, Deposition of Orgill with Exhibits dated Mar. 22, 2006. BS–96.
*KCI* v. *BlueSky*, Deposition of Donald R. Piper, Jr., dated Dec. 1, 2005. BS–97.
*KCI* v. *BlueSky*, Transcript of Deposition of Kathleen Satterfield, D.P.M., with Exhibits, dated Apr. 3, 2006. BS–98.
Slides, drawings and photographs of patient treatment, 21 sheets, (Jeter deposition Exhibit 644) (allegedly dated 1985–1987). BS–225.
Photographs of slides showing patient treatment, 20 sheets, (Jeter deposition Exhibit 645) (allegedly dated 1985–1987). BS–226.
Photographs showing patient treatment, "sheet 1", 11 sheets, (Jeter deposition Exhibit 740) (allegedly dated 1986). BS–227.
Photographs showing patient treatment, "sheet 2", (Jeter deposition Exhibit 741) (allegedly dated 1985). BS–228.
Photographs showing patient treatment, "sheet 3", 18 sheets, (Jeter deposition Exhibit 742) (allegedly dated 1986). BS–229.
Photographs showing patient treatment, "sheet 4", 8 sheets, (Jeter deposition Exhibit 743) (allegedly dated 1985). BS–230.
Photographs showing patient treatment, "sheet 5", 21 sheets, (Jeter deposition Exhibit 744) (allegedly dated 1986). BS–231.
Pictures showing patient treatment, "sheet 1", 12 sheets, (Jeter deposition Exhibit 848) (allegedly dated 1986). BS–232.
Pictures showing patient treatment, "sheet 2", 21 sheets, (Jeter deposition Exhibit 849) (allegedly dated 1985). BS–233.
Pictures showing patient treatment, "sheet 3", 19 sheets, (Jeter deposition Exhibit 850) (allegedly dated 1986). BS–234.
Pictures showing patient treatment, "sheet 4", 8 sheets, (Jeter deposition Exhibit 851) (allegedly dated 1985). BS–235.
Pictures showing patient treatment, "sheet 5", 21 sheets, (Jeter deposition Exhibit 852) (allegedly dated 1986). BS–236.
Documents included as Jeter deposition Exhibit 854, BS–237.
Document "Ex. 5" from deposition of D. Tumey, (dated Mar. 1990). BS–244.
*Innovative Therapies, Inc.*, v. *Kinetic Concepts, Inc., et al.*, Case No. 07–cv–00589 in the United States District Court for the District of Delaware, Complaint filed with jury demand, cover sheet and acknowledgement of consent form, filed by ITI on Sep. 25, 2007. DED–001.
*ITI* v. *KCI*, Case No. 07–589, Motion to dismiss for lack of jurisdiction over the subject matter, proposed order, opening brief in support of motion, and declarations, filed by KCI on Oct. 15, 2007. DED–002.
*ITI* v. *KCI*, Case No. 07–589, Stipulation to extend time regarding briefing schedule on defendant's motion to dismiss and certificate of service, filed by ITI on Oct. 23, 2007, Order Entered Oct. 26, 2007. DED–003.

*ITI* v. *KCI*, Case No. 07–589, Plaintiff's answering brief in opposition to defendants' motion to dismiss, with exhibits, filed by ITI on Nov. 14, 2007. DED–004.

*Kinetic Concepts, Inc., et al.* v. *Medela AG et al.*, Case No. 2:07cv187 in the United States District Court Eastern District of Texas Marshall Division, Complaint with request for jury trial with cover sheet, filed by KCI on May 15, 2007. MDIV187–001.

*KCI* v. *Medela*, Case No. 2:07cv187, Answer to complaint and counterclaim, filed by Medela Inc. on Jul. 10, 2007. MDIV187–002.

*KCI* v. *Medela*, Case No. 2:07cv187, Motion to change venue, with proposed order and exhibits, filed by Medela, Inc. on Jul. 10, 2007. MDIV187–003.

*KCI* v. *Medela*, Case No. 2:07cv187, Motion to dismiss for lack of personal jurisdiction, with proposed order and exhibits A–C, filed by Medela AG on Jul. 11, 2007. MDIV187–004.

*KCI* v. *Medela*, Case No. 2:07cv187, Response to motion to change venue, with proposed order and exhibits, filed by KCI on Aug. 1, 2007. MDIV187–005.

*KCI* v. *Medela*, Case No. 2:07cv187, Answer to Counterclaim, filed by KCI on Aug. 2, 2007. MDIV187–006.

*KCI* v. *Medela*, Case No. 2:07cv187, Response in opposition to motion to dismiss for lack for personal jurisdiction, with proposed order, index, and exhibits, filed by KCI on Aug. 2, 2007. MDIV187–007.

*KCI* v. *Medela*, Case No. 2:07cv187, Reply to response to motion to change venue, with exhibit, filed by Medela, Inc. on Aug. 13, 2007. MDIV187–008.

*KCI* v. *Medela*, Case No. 2:07cv187, Reply to motion to dismiss for lack of personal jurisdiction, with exhibits, filed by Medela AG on Aug. 13, 2007. MDIV187–009.

*KCI* v. *Medela*, Case No. 2:07cv187, Surreply to reply to response to motion to change venue, filed by KCI on Aug. 23, 2007. MDIV187–010.

*KCI* v. *Medela*, Case No. 2:07cv187, Surreply to reply to response to motion to dismiss for lack of pesonal jurisdiction, with exhibits, filed by KCI on Aug. 23, 2007. MDIV187–011.

*Kinetic Concepts, Inc., et al.* v. *Blue Sky Medical Corporation, et al.*, Case No. 2:07cv187 in the United States District Court Eastern District of Texas Marshall Division, Complaint with request for jury trial, with cover sheet, filed by KCI on May 15, 2007. MDIV188–001.

*KCI* v. *Blue Sky*, Case No. 2:07cv188, Amended Complaint with request for jury trial and Request for Declaratory Judgment, with exhibit A, filed by KCI on May 15, 2007. MDIV188–002.

*KCI* v. *Blue Sky*, Case No. 2:07cv188, Answer to Amended Complaint, with Counterclaim, filed by Blue Sky on Jul. 10, 2007. MDIV188–003.

*KCI* v. *Blue Sky*, Case No. 2:07cv188, Motion to dismiss for lack of jurisdiction, with proposed order, corrected proposed order and exhibits A–E, filed by Smith & Nephew Holdings, Inc., Smith & Nephew, PLC on Jul. 13, 2007. MDIV188–004.

*KCI* v. *Blue Sky*, Case No. 2:07cv188, Motion to change venue, with proposed order, corrected proposed order and exhibits 1, 4–9, 11, 12, filed by Blue Sky on Jul. 23, 2007. MDIV188–005.

*KCI* v. *Blue Sky*, Case No. 2:07cv188, Answer to counterclaim filed by KCI on Aug. 2, 2007. MDIV188–006.

*KCI* v. *Blue Sky*, Case No. 2:07cv188, Response in opposition to motion to dismiss for lack of jurisdiction, with proposed order and exhibits 1–7, filed by KCI on Aug. 6, 2007. MDIV188–007.

*KCI* v. *Blue Sky*, Case No. 2:07cv188, Response in opposition to motion to change venue, filed by KCI on Aug. 7, 2007. MDIV188–008.

*KCI* v. *Blue Sky*, Case No. 2:07cv188, Reply in support of motion to dismiss for lack of perosnal jurisdiction, filed by Smith & Nephew Holdings, Inc., Smith & Nephew, PLC on Aug. 16, 2007. MDIV188–009.

*KCI* v. *Blue Sky*, Case No. 2:07cv188, Response to motion to change venue, with exhibits 13–15, filed by Blue Sky on Aug. 16, 2007. MDIV188–010.

*KCI* v. *Blue Sky*, Case No. 2:07cv188, Surreply to reply to response to motion to dismiss for lack of jurisdiction, filed by KCI on Aug. 28, 2007. MDIV188–011.

*KCI* v. *Blue Sky*, Case No. 2:07cv188, Surreply to reply to response to motion to change venue, filed by KCI on Aug. 28, 2007. MDIV188–012.

*Medela, Inc.* v. *Kinetic Concepts, Inc., et al.*, Case No. 7cv449 in the United States District Court Western District of Texas San Antonio Division, Complaint for Declaratory Judgment, filed by Medela Inc. on May 22, 2007. SA449–001.

*Medela* v. *KCI*, Case No. 7cv449, Opposed motion to dismiss, or in the alternative, motion to transfer case, with exhibits 2–4 and proposed order, filed by KCI on Jul. 13, 2007. SA449–002.

*Medela* v. *KCI*, Case No. 7cv449, Answer to Complaint for Declaratory Judgment, filed by KCI on Jul. 13. 2007. SA449–003.

*Medela* v. *KCI*, Case No. 7cv449, Response to motion to dismiss, with Declaration and Exhibits B–G, filed by Medela, Inc. on Aug. 3, 2007. SA449–004.

*Medela* v. *KCI*, Case No. 7cv449, Reply to response to motion to transfer, filed by KCI on Aug. 17, 2007. SA449–005.

*Medela* v. *KCI*, Case No. 7cv449, Order staying defendants' motion entered Oct. 11, 2007. SA449–006.

*Blue Sky Medical Group, Inc., et al.* v. *Kinetic Concepts, Inc. et al.*, Case No. 7cv454 in the United States District Court Western District of Texas San Antonio Division, Complaint for Declaratory Judgment and cover sheet, filed by Blue Sky on May 23, 2007. SA454–001.

*Blue Sky* v. *KCI*, Case No. 7cv454, First Amended and Supplemental Complaint for Declaratory Judgment, filed by Blue Sky on Jul. 12, 2007. SA454–002.

*Blue Sky* v. *KCI*, Case No. 7cv454, Motion to dismiss, or in the alternative, motion to transfer case, with proposed order and exhibits 2–4, filed by KCI on Aug. 1, 2007. SA454–003.

*Blue Sky* v. *KCI*, Case No. 7cv454, Answer to first amended complaint with jury demand, filed by KCI on Aug. 1, 2007. SA454–004.

*Blue Sky v. KCI*, Case No. 7cv454, Response in opposition to motion to dismiss, or in the alternative motion to transfer case, with exhibits A–G and proposed order, filed by Blue Sky on Aug. 16, 2007. SA454–005.

*Blue Sky v. KCI*, Case No. 7cv454, Reply to response to motion, filed by KCI on Aug. 30, 2007. SA454–006.

*Blue Sky v. KCI*, Case No. 7cv454, Order staying defendant's motion pending the outcome of Blue Sky's motion regarding opposed motion to dismiss or in the alternative, motion to tranfer case, entered Oct. 11, 2007. SA454–007.

*KCI et al. v. Blue Sky Medical Group et al.*, 2007–1340, 2007–1341, 2007–1342, Federal Circuit Court of Appeals. Case No. 2007–1340, Appellants Brief, with addendum, filed by Blue Sky on Oct. 19, 2007. CAFC1340–001.

*Wake Forest University Health Sciences, et al. v. Innovative Therapies, Inc.*, Case No. 1:08–cv–32 in the Middle District of North Carolina, Plaintiffs' Original Complaint and Request for Preliminary and Permanent Injunctive Relief, with Patent Form AO120, filed by Wake Forest University on Jan. 10, 2008. MDNC32–001.

Letter to Mr. Urs Tanner from Michael Baniak regarding: Updated Opinion of Non–infringement and Invalidity of Zamierowski U.S. Patent 4,969,880 and Argenta U.S. Patent 5,636,643, 30 pp., (Exhibit D–140) (dated Aug. 23, 2004). NPL–255.

Bier, A., "Hyperemia by Suction Apparatus"Chapter VIII, pp. 74–85 in "Hyperemia as a therapeutic agent", Chicago, Ill.: Roberts Publishing, (1905). NPL–216.

Bucalo, B., et al., "Inhibition of cell proliferation by chronic wound fluid", Wound Repair and Regen, 1(3):181–186 (Jul. 1993). NPL–065.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 10, 18, 19, 24, 25, 29 and 30 is confirmed.

Claims 1–9, 11–17, 20–23, 26–28 and 31–45 were not reexamined.

\* \* \* \* \*